US007078190B2

(12) United States Patent
Belfield et al.

(10) Patent No.: US 7,078,190 B2
(45) Date of Patent: Jul. 18, 2006

(54) COMPOSITIONS AND METHODS UTILIZING THE YEAST ZE01 PROMOTER

(76) Inventors: Graham P Belfield, AstraZeneca R&D Charnwood, Bakewell Road, Loughborough, Leics. (GB) LE11 5RH; Caroline Oakley, AstraZeneca R&D Charnwood, Bakewell Road, Loughborough, Leics. (GB) LE11 5RH ( * ) Notice: Subject to any disclaimer, the term of this patent is extended or adjusted under 35 U.S.C. 154(b) by 104 days.

(21) Appl. No.: 10/776,213

(22) Filed: Feb. 12, 2004

(65) Prior Publication Data

US 2004/0142478 A1 Jul. 22, 2004

Related U.S. Application Data

(63) Continuation of application No. 09/743,194, filed as application No. PCT/SE00/02277 on Nov. 17, 2000, now Pat. No. 6,716,601.

(30) Foreign Application Priority Data

Nov. 23, 1999 (SE) .................................... 9904247

(51) Int. Cl.

| | |
|---|---|
| ***C12N 15/00*** | (2006.01) |
| ***C12N 15/09*** | (2006.01) |
| ***C12N 1/20*** | (2006.01) |
| ***C07H 21/04*** | (2006.01) |
| ***C12P 21/06*** | (2006.01) |

(52) U.S. Cl. ........................... 435/69.1; 435/6; 435/29; 435/91.4; 435/91.41; 435/252.3; 435/254.2; 435/320.1; 435/471; 536/24.1; 536/23.1

(58) Field of Classification Search ............... 435/69.1, 435/91.1, 6, 471, 252.3; 536/23.1
See application file for complete search history.

(56) References Cited

OTHER PUBLICATIONS

Goffeau, et al. Science, 1996, vol. 274, pp. 546-567.*
The Nucleotide Sequence of . . . ; M. Johnson et al., Nature, vol. 387, Supp. pp. 87-90 (1997).
Yeast Sequencing Reports, Sequence Analysis of a 44kb DNA . . . , M. Vandenbol et al., Yeast, vol. 11, pp. 1069-1075 (1995).
Yeast Sequencing Reports, Sequence Analysis of a 37 6 kbp Cosmid . . . , P. Verhasselt et al. Yeast, vol. 13, pp. 241-250 (1997).
Johnston, M., et al.; "*Saccharomyces cervisiae* chromosome XII cosmid 9354"; *Medline; 97313267*; B-Door-External, Terminal 4247-1-2.Log.pp. 5-8; Jul. 24, 2000; Aug. 13, 1997 (Rel. 52, Last Updated, Ver. 3).
Vandenbol, M., et al; "*S. cerevisiae* chromosome XV DNA (44 Kb fragment)"; *Medline; 96076631*; B-Door-External Terminal 4247-4.Log, pp. 5-6; Jul. 24, 2000; Mar. 24, 1997 (Rel. 51, Last Updated, Ver. 7).
Hunt, S., et al; "*S. cerevisiae* chromosome XIII cosmid 9920"; Unpublished; B-Door-External Terminal 4247-2. Log, pp. 3-5; Jul. 24, 2000; Submitted Mar. 10, 1995 to the EMBL/GenBank/DDBJ databases.
Hunt, S., et al; "*S. cervisiae* chromosome XIII cosmid 9718"; Unpublished; B-Door-External Terminal 4247-3. Log; pp. 3-5; Jul. 24, 2000; Submitted May 19, 1995 to the EMBL/GenBank/DDBJ databases.

* cited by examiner

*Primary Examiner*—Nancy Vogel

(57) ABSTRACT

The invention provides novel yeast promoters useful for controlling the expression of homologous and heterologous nucleic acid molecules in yeast cells. The yeast promoters are induced by a fermentable carbon source, such as glucose, or a non-fermentable carbon source, such as ethanol, or both. Therefore, expression of nucleic acid molecules encoding a polypeptide under the control of the novel yeast promoters may be regulated by varying the level of a fermentable carbon source, or a non-fermentable carbon source, or both.

15 Claims, 16 Drawing Sheets

Figure 13 YLR110C promoter region (SEQ ID NO:29)
Sequence shown: Chr XII 370650 to 370051 (reverse orientation)

```
1      AGAACCAAAT GGGAAAATCG GAATGGGTCC AGAACTGCTT TGAGTGCTGG
       TCTTGGTTTA CCCTTTTAGC CTTACCCAGG TCTTGACGAA ACTCACGACC
ATGCAAGCTTCGCGGCCGC          YLR-F
51     CTATTGGCGT CTGATTTCCG TTTTGGGAAT CCTTTGCCGC GCGCCCCTCT
       GATAACCGCA GACTAAAGGC AAAACCCTTA GGAAACGGCG CGCGGGGAGA

101    CAAAACTCCG CACAAGTCCC AGAAAGCGGG AAAGAAATAA AACGCCACCA
       GTTTTGAGGC GTGTTCAGGG TCTTTCGCCC TTTCTTTATT TTGCGGTGGT

151    AAAAAAAAAA AATAAAAGCC AATCCTCGAA GCGTGGGTGG TAGGCCCTGG
       TTTTTTTTTT TTATTTTCGG TTAGGAGCTT CGCACCCACC ATCCGGGACC

201    ATTATCCCGT ACAAGTATTT CTCAGGAGTA AAAAAACCGT TTGTTTTGGA
       TAATAGGGCA TGTTCATAAA GAGTCCTCAT TTTTTTGGCA AACAAAACCT

251    ATTCCCCATT TCGCGGCCAC CTACGCCGCT ATCTTTGCAA CAACTATCTG
       TAAGGGGTAA AGCGCCGGTG GATGCGGCGA TAGAAACGTT GTTGATAGAC

301    CGATAACTCA GCAAATTTTG CATATTCGTG TTGCAGTATT GCGATAATGG
       GCTATTGAGT CGTTTAAAAC GTATAAGCAC AACGTCATAA CGCTATTACC

351    GAGTCTTACT TCCAACATAA CGGCAGAAAG AAATGTGAGA AAATTTTGCA
       CTCAGAATGA AGGTTGTATT GCCGTCTTTC TTTACACTCT TTTAAAACGT

401    TCCTTTGCCT CCGTTCAAGT ATATAAAGTC GGCATGCTTG ATAATCTTTC
       AGGAAACGGA GGCAAGTTCA TATATTTCAG CCGTACGAAC TATTAGAAAG

451    TTTCCATCCT ACATTGTTCT AATTATTCTT ATTCTCCTTT ATTCTTTCCT
       AAAGGTAGGA TGTAACAAGA TTAATAAGAA TAAGAGGAAA TAAGAAAGGA

501    AACATACCAA GAAATTAATC TTCTGTCATT CGCTTAAACA CTATATCAAT
       TTGTATGGTT CTTTAATTAG AAGACAGTAA GCGAATTTGT GATATACTTA
                                        YLR-R            GT
551    AATGCAATTT TCTACTGTCG CTTCTATCGC CGCTGTCGCC GCTGTCGCTT
       TTACGTTAAA AGATGACAGC GAAGATAGCG GCGACAGCGG CGACAGCGAA
       A    CCGGACC
```

YLR111W ORF = Underline

YLR110C ORF = Bold

YLR-F = SEQ ID NO:5

YLR-R = SEQ ID NO:6

Figure 14 YMR251WA promoter region (SEQ ID NO:30)

```
Sequence shown: CHR XIII 773951 TO 774800

1    GCCACGGGTC AACCCGATTG GGATCACCCC ACTGGGGCCC AAGCCTGATA
     CGGTGCCCAG TTGGGCTAAC CCTAGTGGGG TGACCCCGGG TTCGGACTAT
                AGCTAAGCTTCGCGGCCGC              YMR-F
51   TCCGACCTCC ATGAAATTTT TTTTTTTCTT TCGATTAGCA CGCACACACA
     AGGCTGGAGG TACTTTAAAA AAAAAAAGAA AGCTAATCGT GCGTGTGTGT

101  TCACATAGAC TGCGTCATAA AAATACACTA CGGAAAAACC ATAAAGAGCA
     AGTGTATCTG ACGCAGTATT TTTATGTGAT GCCTTTTTGG TATTTCTCGT

151  AAGCGATACC TACTTGGAAG GAAAAGGAGC ACGCTTGTAA GGGGGATGGG
     TTCGCTATGG ATGAACCTTC CTTTTCCTCG TGCGAACATT CCCCCTACCC

201  GGCTAAGAAG TCATTCACTT TCTTTTCCCT TCGCGGTCCG GACCCGGGAC
     CCGATTCTTC AGTAAGTGAA AGAAAAGGGA AGCGCCAGGC CTGGGCCCTG

251  CCCTCCTCTC CCCGCACGAT TTCTTCCTTT CATATCTTCC TTTTATTCCT
     GGGAGGAGAG GGGCGTGCTA AAGAAGGAAA GTATAGAAGG AAAATAAGGA

301  ATCCCGTTGA AGCAACCGCA CTATGACTAA ATGGTGCTGG ACATCTCCAT
     TAGGGCAACT TCGTTGGCGT GATACTGATT TACCACGACC TGTAGAGGTA

351  GGCTGTGACT TGTGTGTATC TCACAGTGGT AACGGCACCG TGGCTCGGAA
     CCGACACTGA ACACACATAG AGTGTCACCA TTGCCGTGGC ACCGAGCCTT

401  ACGGTTCCTT CGTGACAATT CTAGAACAGG GGCTACAGTC TCGATAATAG
     TGCCAAGGAA GCACTGTTAA GATCTTGTCC CCGATGTCAG AGCTATTATC

451  AATAATAAGC GCATTTTTGC TAGCGCCGCC GCGGCGCCCG TTTCCCAATA
     TTATTATTCG CGTAAAAACG ATCGCGGCGG CGCCGCGGGC AAAGGGTTAT

501  GGGAGGCGCA GTTTATCGGC GGAGCTCTAC TTCTTCCTAT TTGGGTAAGC
     CCCTCCGCGT CAAATAGCCG CCTCGAGATG AAGAAGGATA AACCCATTCG

551  CCCTTTCTGT TTTCGGCCAG TGGTTGCTGC AGGCTGCGCC GGAGAACATA
     GGGAAAGACA AAAGCCGGTC ACCAACGACG TCCGACGCGG CCTCTTGTAT

601  GTGATAAGGG ATGTAACTTT CGATGAGAGA ATTAGCAAGC GGAAAAAAAC
     CACTATTCCC TACATTGAAA GCTACTCTCT TAATCGTTCG CCTTTTTTTG

651  TATGGCTAGC TGGGAGTTGT TTTTCAATCA TATAAAAGGG AGAAATTGTT
     ATACCGATCG ACCCTCAACA AAAAGTTAGT ATATTTTCCC TCTTTAACAA

701  GCTCACTATG TGACAGTTTC TGGGACGTCT TAACTTTTAT TGCAGAGGAC
     CGAGTGATAC ACTGTCAAAG ACCCTGCAGA ATTGAAAATA ACGTCTCCTG

751  TATCAAATCA TACAGATATT GTCAAAAAAA AAAAAGACTA ATAATAAAAA
     ATAGTTTAGT ATGTCTATAA CAGTTTTTTT TTTTTCTGAT TATTATTTTT
                                      YMR-R          G A
801  ATGAAGTTAT CTCAAGTTGT TGTTTCCGCC GTCGCCTTCA CTGGTTTAGT
     TACTTCAATA GAGTTCAACA ACAAAGGCGG CAGCGGAAGT GACCAAATCA
          C
```

YMR251W ORF = Underline
YMR251WA ORF = Bold
YMR-F = SEQ ID NO:7
YMR-R = SEQ ID NO:8

Figure 15 YMR107W PROMOTER REGION (SEQ ID NO:31)

Sequence shown: CHR XIII 482463 TO 483063

```
              1  AAAGAATCCA TCACTATTTG AAAAAAAGTC ATCTGGCACG TTTAATTATC
YMR107-F
AGCTAAGCTTCGCGGCCGC
             51  AGAGCAGAAA TGATGAAGGG TGTTAGCGCC GTCCACTGAT GTGCCTGGTA

            101  GTCATGATTT ACGTATAACT AACACATCAT GAGGACGGCG GCGTCACCCC

            151  AACGCAAAAG AGTGACTTCC CTGCGCTTTG CCAAAACCCC ATACATCGCC

            201  ATCTGGCTCC TGGCAGGGCG GTTGATGGAC ATCAGCCGCC TCCCTTAATT

            251  GCTAAAGCCT CCACAAGGCA CAATTAAGCA ATATTTCGGG AAAGTACACC

            301  AGTCAGTTTG CGCTTTTATG ACTGGGTTCT AAGGTACTAG ATGTGAAGTA

            351  GTGGTGACAG AATCAGGGAG ATAAGAGGGA GCAGGGTGGG GTAATGATGT

            401  GCGATAACAA TCTTGCTTGG CTAATCACCC CCATATCTTG TAGTGAGTAT

            451  ATAAATAGGA GCCTCCCTTC CTATTGCAAC TCCATAAAAT TTTTTTTTGT

                                                          MODIFICATION  AT
            501  AGCCACTTCT GTAACAAGAT AAATAAAACC AACTAATCGA GATATCAAAT
                                                       GATTAGCT CTATAGTGTA

            551  ATGGGTAGTT TTTGGGACGC ATTCGCAGTA TACGACAAGA AAAGCACGC
                 TACCCTACCTA YMR107-R
```

YMR107W ORF = Bold
YMR107-F = SEQ ID NO:9
YMR107-R = SEQ ID NO:10

Figure 16 ZEO1 PROMOTER REGION (SEQ ID NO:32)

Sequence shown: CHR XV 109746 TO 110346

```
                       1  TTCAGGAGTC TCTCGCGTTA GAGCAGTACG TGGCGCAGCT AAACTCGCCG
ZEO1-F →
AGCTAAGCTTCGCGGCCGC
                      51  GGAGGTCTGCTTCACGAGCG CGGTGTGCGC CTAGTATTGC CCCGACGGTC

                     101  CGGGTGCCTA TCCCTAGATT TCGTCGTGCC CCGACCCAAA TAGTTAAACG

                     151  TGTGGTTTAT GGGTGCACCA GGGCTTTATC GTGTTTTATA TCGATGGCGA

                     201  TTTGTGCCTC CAGTGTATTT TTGTATATCC AATTAAGGTT TCTTACCTAA

                     251  TTTTATTTTT ATCATCTTTA GTTAATGCTG GTTTGCTCTG TTTCTGCTGC

                     301  TTTCTGTGCG GTTCTCCTCT TCTCTTGTTT CTTCGTGTTG TCCCCCATCG

                     351  CCGATGGGCT TATATGGCGT ATATATATAG AGCGAGTTTT TACGTCGAAG

                     401  ATCATCTCAG TTTGCTTGAT AGCCTTTCTA CTTTATTACT TTCGTTTTTA

                     451  ACCTCATTAT ACTTTAGTTT TCTTTGATCG GTTTTTTTCT CTGTATACTT

                     501  AAAAGTTCAA ATCAAAGAAA CATACAAAAC TACGTTTATA TCAATTAATA
                                                           GCAAATAT AGTTAATGTA

                     551  ATGTCTGAAA TTCAAAACAA AGCTGAAACT GCCGCCCAAG ATGTCCAACA
                          TACGCTAGCAT ZEO1-R
```

YOL110W ORF = Underline
ZEO1 (YOL109W) ORF = Bold
ZEO1-F = SEQ ID NO:11
ZEO1-R = SEQ ID NO:12

COMPOSITIONS AND METHODS UTILIZING THE YEAST ZE01 PROMOTER

This application is a continuation of application Ser. No. 09/743,194, filed Jan. 8, 2001, now U.S. Pat. No. 6,716,601, which is a 371 of PCT/SE00/02277, filed Nov. 17, 2000, the entire content of which is hereby incorporated by reference in this application.

BACKGROUND OF THE INVENTION

The controlled production in yeast of an enormous variety of useful proteins or polypeptides can be achieved using recombinant DNA technology. Yeast cells can be transformed with yeast expression vectors, which contain homologous or heterologous nucleic acid molecules encoding polypeptides (coding sequences). The yeast cells can then produce large quantities of the useful proteins or polypeptides in yeast cell culture.

Expression of the nucleic acid molecule encoding a polypeptide by the yeast expression vector is initiated at a region known as the promoter, which is recognized by and bound by RNA polymerase. The RNA polymerase travels along the DNA, transcribing the information contained in the coding strand from its 5' to 3' end into messenger RNA, which is in turn translated into a polypeptide having the amino acid sequence for which the DNA codes. The present invention provides novel yeast promoters useful for, inter alia, controlling the expression of homologous and heterologous nucleic acid sequences encoding proteins and polypeptides in yeast cells.

SUMMARY OF THE INVENTION

It is an object of the invention to provide novel yeast promoters, yeast expression vectors, and transformed yeast cells. It is a further object of the invention to provide a method for producing proteins and polypeptides in yeast cell culture.

In one embodiment of the invention a yeast promoter which comprises at least 17 contiguous nucleotides of an isolated and purified polynucleotide is provided. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

As used herein, the term “promoter” refers to a nucleic acid sequence which is cable of initiating transcription of a nucleic acid molecule encoding a polypeptide (coding sequence); a “yeast promoter” is capable of initiating transcript of a coding sequence in yeast cells; and “promoter activity” refers to the level or amount of transcription initiation of a coding sequence, and encompasses any level above background (i.e., the level or amount that occurs in the absence of a promoter; a background level, which is normally zero).

Another embodiment of the invention provides a yeast promoter which comprises an isolated and purified polynucleotide. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

Yet another embodiment of the invention provides a yeast promoter fragment which comprises at least 17 contiguous nucleotides of a polynucleotide. The polynucleotides are shown in SEQ ID NO:1, SEQ ID NO:2, SEQ ID NO:3, and SEQ ID NO:4. The fragment has promoter activity as determined by cloning the fragment into a yeast expression vector, wherein the fragment is operably linked to a reporter gene, transforming yeast cells with the yeast expression vector, growing the yeast cells in yeast cell culture under conditions favorable for expression of the reporter gene, and assaying the yeast culture for a reporter protein expressed by the reporter gene. The expression of the reporter gene indicates the fragment has promoter activity.

Still another embodiment of the invention provides a yeast expression vector comprising a yeast promoter. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

A further embodiment of the invention provides a yeast expression vector where activity of the promoter is controlled by varying the level of a non-fermentable carbon source, such as ethanol, in a medium of yeast cells in culture. The yeast cells are transformed with said yeast expression vector.

In yet another embodiment of the invention, a yeast expression vector comprising a yeast promoter which comprises at least 17 contiguous nucleotides of an isolated and purified polynucleotide is provided. The promoter sequences are shown in SEQ ID NO:1, SEQ ID NO:2, and SEQ ID NO:4. Promoter activity is controlled by varying the level of a fermentable carbon source in a medium of yeast cells in culture, where the yeast cells are transformed with the yeast expression vector. The fermentable carbon source can be glucose.

Another embodiment of the invention provides a yeast expression vector comprising a yeast promoter. The yeast promoter comprises at least 17 contiguous nucleotides of an isolated and purified polynucleotide. The promoter sequences are shown in SEQ ID NO:1, SEQ ID NO:2, and SEQ ID NO:4. Promoter activity is controlled by varying the level of a fermentable carbon source and a non-fermentable carbon source, such as ethanol, in a medium of yeast cells in culture, where the yeast cells are transformed with the yeast expression vector. The fermentable carbon source can be glucose. The non-fermentable carbon source can be ethanol.

Still another embodiment of the invention provides a yeast cell transformed with a yeast expression vector. The yeast expression vector comprises a yeast promoter. The promoter sequences are shown in SEQ ID NO:1, SEQ ID NO:2, SEQ ID NO:3, and SEQ ID NO:4. The promoter is operative when operably linked to a nucleic acid molecule encoding a polypeptide.

Yet another embodiment of the invention provides a method for producing a polypeptide. A yeast expression vector is constructed where a polynucleotide encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, SEQ ID NO:3, and SEQ ID NO:4. The promoter is operative when operably linked to a nucleic acid molecule encoding a polypeptide. A culture of yeast cells is transformed with the yeast expression vector. The yeast cells are maintained in culture so that the polypeptide is expressed. The polypeptide is then recovered.

Still another embodiment of the invention provides a method for producing a polypeptide. A nucleic acid molecule encoding the polypeptide is cloned into an expression vector selected from the group consisting of pYLR110P+luc, pYMR251AP+luc, pYMR107P+luc, pZEO1P+luc, pYLR110P, pYMR251AP, pYMR107P, and pZEO1P. The nucleotide acid molecule is operably linked to a promoter of the expression vector. A culture of yeast cells is transformed with the yeast expression vector. The yeast cells are maintained in culture so that the polypeptide is expressed and the polypeptide is then recovered.

Another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, and SEQ ID NO:4. Yeast cells are transformed with the yeast expression vector and are maintained in culture medium. The expression of the nucleic acid molecule encoding the polypeptide is controlled by varying the level of a fermentable carbon source, such as glucose, in the culture medium. The polypeptide is then recovered.

Still another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, SEQ ID NO:3, and SEQ ID NO:4. The promoter is operative when operably linked to a nucleic acid molecule. A culture of yeast cells is transformed with the yeast expression vector. The yeast cells are maintained in culture medium and the expression of the nucleic acid molecule encoding the polypeptide is controlled by varying the level of a non-fermentable carbons source, such as ethanol, in the culture medium. The polypeptide is then recovered.

Another embodiment of the invention provides a method for producing a polypeptide. A yeast expression vector is constructed where a nucleic acid molecule encoding the polypeptide is controlled by a yeast promoter. The yeast promoter comprises at least 17 contiguous nucleotides of an isolated and purified polynucleotide. The promoter sequences are shown in SEQ ID NO:1, SEQ ID NO:2, and SEQ ID NO:4. A culture of yeast cells is transformed with the yeast expression. The yeast cells are maintained in culture medium and the expression of the nucleic acid encoding the polypeptide is controlled by varying the level of a fermentable carbon source, such as glucose, and a non-fermentable carbon source, such as ethanol, in the culture medium. The polypeptide is then recovered.

Yet another embodiment of the invention provides a method of identifying a promoter fragment with promoter activity by generating a fragment comprising at least 17 contiguous nucleotides of an isolated and purified polynucleotide. The polynucleotides are shown in SEQ ID NO:1, SEQ ID NO:2, SEQ ID NO:3, and SEQ ID NO:4. The fragment is cloned into a yeast expression vector, so that the fragment is operably linked to a reporter gene. Yeast cells are transformed with the yeast expression vector and grown in yeast cell culture under conditions favorable for expression of the reporter gene. The yeast culture is assayed for a reporter protein expressed by the reporter gene. Expression of the reporter gene indicates the fragment has promoter activity.

BRIEF DESCRIPTION OF THE DRAWINGS

FIG. 13 schematically illustrates the YLR110C promoter region.

FIG. 14 schematically illustrates the YMR251WA promoter region.

FIG. 15 schematically illustrates the YMR107W promoter region.

FIG. 16 schematically illustrates the ZEO1 promoter region.

DETAILED DESCRIPTION OF THE INVENTION

Figure 1:
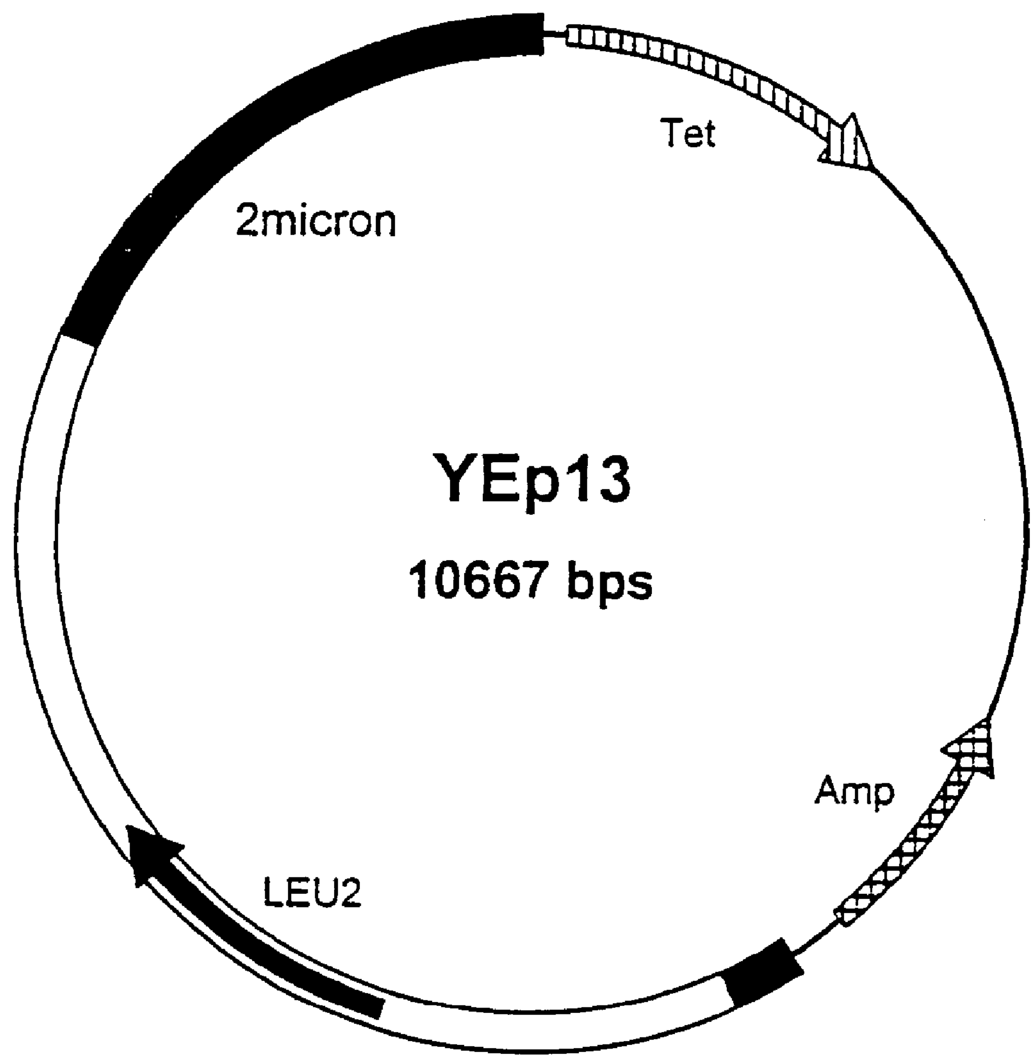
FIG. 1 is a map of YEp13 expression vector.

Novel yeast promoters whose activity can be controlled by a fermentation carbon source, such as glucose, or a non-fermentable carbon source, such as ethanol, or both have been identified. The yeast promoters are useful for, inter alia, the high level production of proteins or polypeptides in yeast cell culture.

Yeast Promoters

The isolated and purified promoter polynucleotides of the invention are shown in SEQ ID NO:1 (the YLR110C promoter), SEQ ID NO:2 (the YMR251WA promoter), SEQ ID NO:3 (the YMR107W promoter), and SEQ ID NO:4 (the ZEO1 promoter). Yeast promoters comprising as little as 17 nucleic acids have been determined to function as promoters. The yeast promoters of the invention comprise at least 17, 25, 50, 75, 100, 150, 200, 250, 300, 350, 400, 450, 500, 600 or 700 contiguous nucleic acids of an isolated and purified polynucleotide up to the maximum length provided in any one of the sequences presented herein, that is, SEQ ID NO:1, SEQ ID NO:2, SEQ ID NO:3, and SEQ ID NO:4.

Preferably, the promoter polynucleotides are isolated free of other components, such as proteins and lipids. The polynucleotides can be made by a cell and isolated or can be synthesized in the laboratory, for example, using an automatic synthesizer or an amplification method such as PCR.

Naturally occurring variants and artificial sequence variants (that is, those which do not occur in nature) of the promoters are included in the invention. Variants of the promoters and/or fragments thereof have, along their entire length, sequence identity of at least 90%, and preferably greater than 95% as determined by the Smith-Waterman homology search algorithm as implemented in MPsrch™ program (University of Edinburgh) using an affine gap search with the following search parameters: gap open penalty: 12, gap extension penalty: 1.

Fragments of the full-length promoters are also functional as promoters. A promoter fragment of at least 17 contiguous nucleotides may occur at any position along the full-length promoter as shown in SEQ ID NO:1, SEQ ID NO:2, SEQ ID NO:3 or SEQ ID NO:4. Accordingly, promoter activity of 17 or more contiguous nucleotides occurring anywhere along the full-length promoter can be analyzed. Fragments of 17, 25, 50, 75, 100, 150, 200, 250, 300, 350, 400, 450, 500, 550, 600, 650 or 700, nucleotides of the promoters may be constructed by, for example, subjecting an isolated promoter to restriction endonucleases, to 5'- or 3'-deletion mutagenesis, to PCR, or to site specific deletion. A combination of these methods can also be used to generate fragments of a promoter.

The invention further embodies a hybrid promoter, i.e., a promoter that comprises more than one promoter or more than one fragment of a promoter from which it was derived. The promoter fragments can be derived from more than one of the promoter sequences shown in SEQ ID NO:1, SEQ ID NO:2, SEQ ID NO:3 and SEQ ID NO:4. The promoters and fragments can be constructed as described above, ligated together, and cloned into a yeast expression vector. Where a promoter comprises nucleotides from at least two polynucleotides selected from the group consisting of SEQ ID NO:1, SEQ ID NO:2, SEQ ID NO:3 and SEQ ID NO:4, at least 5, 6, 7, 8, 9, 10, 25, 50, 75, 100, 150, 200, 250, 300, 350, 400, 450, 500, 550, 600, or 650 contiguous nucleotides are derived from each of the polynucleotides to form a promoter of at least 17 nucleotides. Alternatively, each of the full-length promoters can be combined with another full-length promoter or with fragments of another promoter.

The yeast promoters, fragments of the promoters, and hybrid promoters are useful for controlling expression of a protein or polypeptide when the yeast promoter is operably linked to a nucleic acid molecule encoding the protein or polypeptide.

Determination of Promoter Activity

Promoters and fragments of promoters can be assayed for promoter activity by cloning a fragment of a promoter, or a full-length promoter, or a hybrid promoter into a yeast expression vector so that is operably linked to a reporter gene, i.e., a coding sequence for a reporter protein. The yeast expression vector is transformed in yeast cells, which are grown in yeast cell culture under conditions favorable for expression of the reporter gene, for example, under conditions providing a fermentable and/or non-fermentable carbon source. Expression of the reporter gene, as determined by an assay for the amount of a reporter protein expressed by the reporter gene, indicates that the promoter has activity.

For example, to determine if a promoter has activity, i.e. is operative, expression of a reporter gene by a promoter of the invention may be compared to expression of the reporter gene by a reference promoter such as PBR1 (Cottingham et al. (1991) Eur J Biochem 196(2):431–8, Sleep et al. (1991) Biotechnology 9(2):183–7; Finnis et al. (1992) Yeast 8(1): 57–60; Meldgaard et al. (1995) Glycoconj J 12(3):380–90; Bach et al. (1996) Receptors and Channels 4(2):129–39. A promoter, a fragment of a promoter, or a hybrid promoter of the invention is operative if it expresses at least 25% of the amount of a reporter protein as the full-length PBR1 promoter in a medium containing a non-fermentable carbon source, or a fermentable carbon source, or both. Preferably, an operative promoter expresses at least 50%, 75%, 100%, 200%, 300%, 400%, or more of the amount of a reporter protein as the full-length PBR1 reference promoter.

Assays for promoter activity are useful for identifying yeast promoters with high activity and the specific nucleotide sequences of the promoters that are necessary for promoter activity.

Yeast Expression Vectors

The yeast promoters of the invention, which comprise isolated and purified polynucleotides selected from the group consisting of SEQ ID NO:1, SEQ ID NO:2, SEQ ID NO:3, and SEQ ID NO:4 or fragments thereof, can be used to construct yeast expression vectors.

Yeast expression vectors are any vectors capable of autonomous replication within a yeast host organism or capable of integrating into the yeast genome. Yeast expression vectors are useful for introducing foreign DNA into yeast cells. Typical yeast expression vectors include yeast integrative plasmids (YIp), yeast replicating plasmids (YRp), yeast expression plasmids (YXp), yeast centromere-containing plasmids (YCp), and yeast episomal plasmids (YEp). Preferably, a yeast expression vector can be selected and maintained in both yeast and *E. coli.*

Yeast expression vectors, typically plasmids, incorporate the yeast promoters of the invention to control expression of nucleic acid molecules encoding heterologous or homologous proteins or polypeptides. The nucleic acid molecules are operably linked to a promoter in the yeast expression vector. A wide range of heterologous eukaryotic and prokaryotic proteins of peptides may be expressed by the vectors of the invention.

Expression vectors incorporating the promoters can be constructed by inserting into a vector a nucleic acid molecule encoding a protein or polypeptide (coding sequence) which is to be expressed. The coding sequence can be inserted at a restriction site which is provided downstream of a translation start codon controlled by the promoter. The coding sequence must be inserted in the correct translational reading frame.

Alternatively, the polynucleotide can itself be provided with a translational start codon followed directly by a coding sequence. Where the promoter does not contain a translational start codon, a restriction site is provided so that the coding sequence can be inserted in the correct reading fame and so that its translational start codon is correctly positioned in relation to the promoter. The coding sequence can encode heterologous or homologous or eukaryotic or prokaryotic polypeptide or proteins. In a preferred embodiment the coding sequence encodes a fusion protein. The coding sequence may further comprise a signal sequence.

In addition to the promoters of the invention, other components can be added to the expression vectors of the invention. For example, yeast selective markers, such as LEU2 or TRP1, which allow for selection of yeast cells that have been effectively transformed by the vector can be added. A yeast replication origin, such as the replication origin of the 2-micron plasmid or the autonomous ARS replication segment can be added. Upstream activating sequences and transcription terminator sequences may be added. Further, at least a portion of a bacterial plasmid, such as found in YEp13, can be added to enable the yeast expression vector to be manipulated in an intermediate bacterial host system, such as *Escherichia coli.*

The expression vector may also comprise a reporter gene which encodes, for example, β-galactosidase or luciferase. The reporter gene can be under the control of a promoter of the invention. Where the reporter gene, i.e. coding sequence, is linked to a gene encoding a desired protein, assaying the level of expression of the reporter protein can quickly and easily determine the level of expression of the desired protein.

The expression vectors of the invention can be used to direct the fermentable carbon source- and/or non-fermentable carbon source-induced high level expression of proteins or polypeptides in yeast. The promoters of the invention can be induced by the presence of a fermentable carbon source, such as glucose, or a non-fermentable carbon source, such as ethanol, or both. That is, the promoters have greater promoter activity in the presence of a fermentable carbon source, or a non-fermentable carbon source, or both than in the absence of a fermentable carbon source, or a non-fermentable carbon source, or both. Promoters YLR110C, as shown in SEQ ID NO:1; YMR251WA, as shown in SEQ ID NO:2; and ZEO1, as shown in SEQ ID NO:4, can be induced by a fermentable carbon source, such as glucose, or by a non-fermentable carbon source, such as ethanol, or by both. Promoter YMR107W, as shown in SEQ ID NO:3, can be induced by a non-fermentable carbon source, such as ethanol. Thus, the amount of expression of a homologous or heterologous nucleic acid molecule encoding a protein operably linked to the promoters of the invention can be controlled by varying the amount of an available fermentable carbon source, such as glucose, or a non-fermentable carbon source, such as ethanol, or both.

Transformed Yeast Cells

Yeast cells can be transformed with the yeast expression vectors of the invention. Transformation can be accomplished by well known methods, including, but not limited to electroporation, calcium phosphate precipitation, and microinjection. The yeast expression vectors of the invention can be used to transform yeast cells, including, but not limited to *Saccharomyces cerevisiae, S. uvarum, S. carlsbergensis, Saccharomycopsis lipolytica, Schizosaccharomyces pombe,* and *Kluyveromyces lactis.*

Transformed yeast cells containing a yeast expression vector can be grown in an appropriate medium for the yeast. A fermentable or non-fermentable carbon source can be added to the yeast culture medium in order to control the activity of the promoter.

Methods of Production of Proteins

Yeast cells transformed with expression vectors comprising a promoter of the invention can be used to produce proteins and polypeptides. Under proper cell culture conditions, preferably in the presence of a fermentable or non-fermentable carbon source, or both, the promoters of the invention will control expression of a nucleic acid molecule encoding a polypeptide operably linked to the promoter.

The protein or polypeptide can be retained within the yeast cell. The yeast cells can be then harvested, lysed, and the protein obtained and substantially purified in accordance with conventional techniques. Such techniques include, but are not limited to chromatography, electrophoresis, extraction, and density gradient centrifugation.

In a preferred embodiment of the invention, the protein or polypeptide to be recovered will further comprise a signal peptide capable of transporting the protein or polypeptide through the membrane of a transformed yeast cell. The protein or polypeptide can be recovered from the culture medium by, for example, adsorption or precipitation.

Further, the proteins and polypeptides may be produced as a fusion protein, which includes not only the amino acid sequence of the desired protein, but also one or more additional proteins. Affinity purification protocols can be used to facilitate the isolation of fusion proteins. Typically, a ligand capable of binding with high specificity to an affinity matrix is chosen as the fusion partner for the desired protein. For example, fusion proteins made with glutathione-S-transferase can be selectively recovered on glutathione-agarose and IgG-Sepharose can be used to affinity purify fusion proteins containing staphylococcal protein A.

Preferably, the protein or polypeptide of interest can be separated from the remainder of the fusion protein. The fusion protein can be constructed so that a site for proteolytic or chemical cleavage is inserted between the protein of interest and the fusion partner. For example, sites for cleavage by collagenase, Factor Xa proteins, thrombin, and enterokinase, have been inserted between the fusion partner and the protein of interest. The protein of interest can be also cleaved from the remainder of the fusion protein by chemical cleavage by, for example, hydroxylamine, cyanogen bromide (CNBr), or N-chlorosuccinamide.

The following are provided for exemplification purposes only and are not intended to limit the scope of the invention described in broad terms above. All references cited in this disclosure are incorporated by reference.

EXAMPLE 1

Preparation of Yeast Samples

*S. cerevisiae* Strain 11C

This example describes the growth of haploid *Saccharomyces cerevisiae* strain 11C. It has the genotype: ade2-161, trp1-Δ63, ura3-52, lys2-801, leu2Δ1 &/or leu2-3 &/or leu2-112, his3Δ200 &/or his4-519. 11C was generated by crossing the strains YPH500 (Mat a ura3-52 lys2-801 ade2-161 trp1-Δ63 his3Δ200 leu2Δ1) (Sikorski and Hieter. (1989) A system of shuttle vectors and yeast host strains designed for efficient manipulation of DNA in *Saccharomyces cerevisiae. Genetics* 122: 19–27) and AH22 (MATa leu2-3 leu2-112 his4-519) (Hinnen et al. (1978) Transformation of yeast. *Proc. Natl. Acad. Sci. USA* 75: 1929–1933).

Three sterile 500 ml conical flasks, each containing 100 ml sterile YPD broth (Sigma, Cat No. Y-1375) were inoculated with sterile 10 μl loops of differing quantities of the *S. cerevisiae* strain 11C from a freshly streaked YPD plate (Sigma, Cat No. Y-1500), and grown in an orbital shaker at 30° C., 200 rpm, overnight. The growth of 11C in the three flasks was measured by absorbance at 600 nm. One flask was deemed to be at the late exponential growth phase (1.98 ODU ml at 600 nm), and this culture was used to inoculate (50 ml o/n culture per flask) 2 identical 5L sterile conical flasks (labeled E and L), each containing 1L sterile YPD broth to a final concentration of ~0.1 ODU ml. Flasks E and L were grown in an orbital shaker at 30° C., 200 rpm. 10 ml samples were collected at times indicated below (Table 1). The samples were treated as follows: their growth was determined (A600 nm), the possibility of contamination was checked (using a light microscope), cells were harvested in a benchtop centrifuge (~2000×g for 5 minutes), and the supernatant removed and frozen at −20° C. (samples labeled E0–E3, and L0–L5).

TABLE 1

Growth of cultures E and L as measure by absorbance at 600 nm.

| Time Point | Time after inoculation (min) | Growth of flask E (ODU) | Growth of flask L (ODU) |
|---|---|---|---|
| T0 | 0 | 0.099 | 0.099 |
| T1 | 310 | 0.37 | 0.36 |
| T2 | 410 | 0.71 | 0.72 |
| T3 | 455 | 0.97 | 0.92 |
| T4 | 775 | — | 3.64 |
| T5 | 1420 | — | 6.05 |

After 455 minutes, a time deemed to be late exponential growth phase in glucose, flask E (i.e. early) was harvested (~2000×g for 5 minutes), split into 50 ml aliquots, and frozen at −80° C. After 1420 minutes, a time deemed to be growth on ethanol, flash L (i.e. late) was harvested (~2000×g for 5 minutes), split into 50 ml aliquots, and frozen at −80° C.

Determination of Glucose and Ethanol Concentration

Supernatant samples (E0–E3, and L0–L5) were defrosted, and their ethanol and glucose contents were measured using ethanol (Boehringer, Cat. No. 176290) and glucose (Boehringer, Cat. No. 176251) detection kits according to manufacturers instructions. The concentrations determined are shown below in Table 2.

TABLE 2

Glucose and Ethanol concentrations in supernatants of cultures E and L at different time points.

| Sample | Time after inoculation (min) | Glucose level in media (g $L^{-1}$) | Ethanol level in media (g $L^{-1}$) |
|---|---|---|---|
| E0 | 0 | 20.0 | 0.0 |
| E1 | 310 | 21.8 | 0.3 |
| E2 | 410 | 21.8 | 0.8 |
| E3 | 455 | 21.2 | 0.87 |
| L0 | 0 | 20.0 | 0.0 |
| L1 | 310 | 22.2 | 0.36 |
| L2 | 410 | 22.0 | 0.62 |
| L3 | 455 | 20.0 | 0.87 |
| L4 | 775 | 11.8 | 5.2 |
| L5 | 1420 | 0.0 | 11.8 |

It can seen in Table 2 that at the point of culture harvest for E (E3, 455 minutes), the cells were still utilizing glucose as a carbon source, while at the point of culture harvest for L (L5, 1420 minutes), glucose was exhausted, and the cells were utilizing ethanol as a carbon source. Calibration values used to calculate glucose concentrations are shown in Table 3. Calibration values used to calculate ethanol concentrations are shown in Table 4.

TABLE 3

Glucose standards

| GLUCOSE STANDARDS g/l | OD A340 |
|---|---|
| 0 | 0 |
| 0.2 | 0.246 |
| 0.4 | 0.461 |
| 0.6 | 0.726 |
| 0.8 | 0.967 |
| 1 | 1.227 |

TABLE 4

Ethanol standards

| ETHANOL STANDARDS g/L | OD A340 |
|---|---|
| 4.72 | 0.041 |
| 9.44 | 0.083 |
| 18.88 | 0.166 |
| 37.76 | 0.322 |
| 56.6 | 0.534 |
| 75.5 | 0.664 |
| 94.4 | 0.846 |

EXAMPLE 2

Analysis of RNA Levels from Yeast Dimorphic Growth Samples

Total RNA Isolation

Total RNA was isolated from 300 ml of culture using the hot phenol protocol. The frozen yeast pellets were resuspended in lysis buffer (4 ml) (0.5 ml Tris-CL (1M, pH 7.5), 1.0 ml EDTA (0.5 M), 2.5 ml 10% SDS, and 46.0 ml ddH$_2$O) and an equal volume of acid phenol was added and vortexed. Following incubation at 65° C. for one hour (with occasional vigorous vortexing) the mixture was placed on ice for 10 minutes then centrifuged (10 minutes). The aqueous layer was transferred to a fresh centrifuge tube and mixed with an equal volume of phenol at room temperature. The mixture was centrifuged and an equal volume of chloroform was mixed with the aqueous layer in a fresh centrifuge tube. Following centrifugation the aqueous layer was transferred to a fresh centrifuge tube and sodium acetate (to a final concentration of 0.3M) and two volumes of 100% ethanol was added to precipitate the RNA. The mixture was placed at −20° C. for 30 minutes then centrifuged for 10 minutes to pellet the RNA. The RNA pellet was washed 2–3 times with 70% ethanol then allowed to dry at room temperature. The pellet was resuspended in ddH2O (200–500 μL). The RNA was quantitated by measuring OD 260–280. Yield of total RNA was ~4.5 mg from each culture.

Poly A+ RNA Purification

Poly A+ RNA was purified from total RNA using Qiagen Oligotex mRNA Midi Kit (Qiagen, Cat. No. 70042). 2 mg of total RNA was used as starting material and made up to a volume of 500 μl with DEPC treated $H_2O$. To this 500 μl buffer OBB (2× binding buffer) and 55 μl oligotex suspension was added. The "Ologotex mRNA Spin Column Protocol" from the kit protocol booklet was followed. The pelleted mRNA was washed in 200 μl 75% ethanol, dried and resuspended in 10 μl DEPC treated $H_2O$. Yield of Poly A+ RNA was ~8 μg for each sample.

cDNA Synthesis cDNA was synthesized using the protocol for GeneChip Expression Analysis Manual using reagents from Gibco BRL Life Technologies Superscript Choice System cat. No. 18090-019. For each sample 5 μg Poly A+ RNA was added to 100 pmol of T7-$(dT)_{24}$ primer (sequence: GGCCAGTGAATTGTAATACGACTCACTATAGGGAGGCGG-(T) 24, HPLC purified) (SEQ ID NO:15) in a total of 8 μl (made up to volume with DEPC treated $H_2O$). The reaction mixture was incubated for 10 minutes at 70° C. in a Perkin Elmer PE9600 thermalcycler then put on ice. The following reagents were added to the reaction mixture: 4 μl 5× first strand cDNA buffer; 2 μl 0.1M DTT; and 1 μl 10 mM dNTP mix. The reaction mixture was mixed and incubated at 37° C. for 2 minutes in a Perkin Elmer PE9600 thermocycler. 5 μl SuperScript II reverse transcriptase was then added. The mixture was incubated at 37° C. for 1 hour in a Perkin Elmer PE9600 thermocycler.

The first strand cDNA reaction was placed on ice and the following reagents added: 91 μl DEPC treated $H_2O$; 30 μl 5× second strand reaction buffer; 3 μl 10 mM dNTP mix; 1 μl 10 units/μl *E. coli* DNA ligase; 4 μl 10 units/μl *E. coli* DNA Polymerase I; and 1 μl 2 units/μl RNase H. The mixture was incubated at 16° C. for 2 hours in a Perkin Elmer PE9600 thermalcycler. 2 μl 5 units/μl T4 DNA Polymerase was then added. The mixture was incubated for a further 5 minutes at 16° C. in a Perkin Elmer PE9600 thermalcycler. 10 μl 0.5M EDTA was then added.

The double stranded DNA was cleaned up by phenol extraction. The reaction product transferred to a 1.5 ml eppendorf tube and 162 μl Tris pH 8.0 saturated phenol was added. The tube was mixed by vortexing, the tube was then centrifuged in a microfuge at 13,000 rpm for 5 minutes. The top fraction was recovered and cDNA precipitated by addition of 60 μl 7.5M ammonium acetate plus 400 μl absolute ethanol. This was immediately centrifuged in a microfuge at 13,000 rpm for 20 minutes. The supernatant fraction was discarded, the pellet was washed in 75% ethanol and then air-dried. The pellet was resuspended in 20 μl DEPC treated $H_2O$.

Synthesis of Biotin-Labeled cRNA by In Vitro Transcription (IVT)

Reagents from Ambion MEGAscript T7 kit, cat. No. 1334, were used for the synthesis of biotin-labeled cRNA by in vitro transcription (IVT). The NTP Labeling mix comprised 7.5 mM ATP; 7.5 mM GTP; 5.625 mM UTP; 1.875 mM Biotin-16-UTP (Enzo cat No. 42814); 5.625 mM CTP; and 1.875 mM Biotin-11-CTP (Enzo cat No. 42818). The IVT Labeling reaction comprised: 14.5 μl NTP Labeling mix; 2 μl 10× Ambion Transcription Buffer; 1.5 μl Double strand cDNA (from above); and 2 μl Ambion T7 Enzyme Mix.

The reaction mixture was incubated for 6 hours at 37° C. in a Perkin Elmer PE9600 thermalcycler. The biotinylated cRNA was cleaned up using Qiagen RNeasy kit, cat No. 74103. The RNeasy kit protocol was followed exactly. RNA was eluted in 2 aliquots of 30 μl DEPC treated $H_2O$. The RNA was precipitated by addition of 6 μl 3M sodium acetate pH 5.5 plus 7.5 μl absolute ethanol. The RNA was allowed to precipitate overnight at −20° C. Samples were centrifuged in a microfuge at 13,000 rpm for 20 minutes to pellet the RNA. The supernatant fraction was discarded and the pellet was washed in 1 ml of 75% ethanol and then allowed to air dry. The pellet was then resuspended in 20 μl DEPC treated $H_2O$. The yield of cRNA was ~40 μg for each sample.

cRNA Fragmentation

11 μg of cRNA was fragmented. 8 μl of 5× Fragmentation buffer (200 mM Tris-Acetate pH 8.1, 500 mM potassium acetate, 150 mM magnesium acetate) plus 11 μg cRNA made up to 20 μl with DEPC treated $H_2O$ was used. The reaction mixture was incubated 94° C. for 35 minutes in a Perkin Elmer PE9600 thermal cycler.

Hybridization to GeneChip Microarray

The hybridization mix comprised: 20 μl (11 μg) of fragmented cRNA; 2.2 μl of control oligo B2 (50 pmol/μl) (seq: 5'Biotin-GTCAAGATGCTACCGTTCAG 3'HPLC purified) (SEQ ID NO:16); 2.2 μl Herring Sperm DNA (10 mg/ml); 110 μl 2× Buffer (2M NaCl, 20 mM Tris pH 7.6, 0.01% Triton X-100); and 85.6 μl DEPC treated $H_2O$. The hybridization mix heated to 95° C. in a Techne hot block for 5 minutes, followed by incubation at 40° C. for 5 minutes. The hybridization mix was clarified by centrifugation in microfuge at 13,000 rpm for 5 minutes.

200 μl of supernatant to added to the GeneChip cartridge (GeneChip cartridge was previously pre-wetted with 200 μl 1× Buffer and incubated for 10 minutes at 40° C. in the rotisserie box of a GeneChip hybridization oven 320 (cat No. 800127) at maximum rpm. The sample was hybridized to the microarray overnight at 40° C. in a GeneChip hybridization oven in the rotisserie at maximum rpm.

Washing and Staining of Probe Arrays

The hybridization mix was recovered from the GeneChip cartridge and put back in the tube containing the remainder of the sample. 200 μl 6×SSPE-T (6×SSPE plus 0.005% Triton X-100) was applied to the chip and pipetted in and out twice. This process was repeated twice more. Another 200 μl 6×SSPE-T was applied to the cartridge and the cartridge was then incubated for 1 hour at 50° C. at maximum rpm in the GeneChip hybridization oven. The 6×SSPE-T was removed and 200 μl 0.5×SSPE-T was added to cartridge. The cartridge was incubated for 15 minutes at 50° C. at maximum rpm in the GeneChip hybridization oven. The 0.5×SSPE-T was removed and the cartridge was re-filled with 200 μl 6×SSPE-T.

The stain solution comprised: 190 μl 6×SSPE-T; 10 μl of 20 mg/ml acetylated BSA; and 2 μl 1 mg/ml conjugated streptavidin:phycoerythrin (Molecular Probes cat. No. S-866). 200 μl 6×SSPE-T was removed from the GeneChip cartridge and 200 μl of stain solution added. The cartridge was incubated at ambient temperature in a GeneChip hybridization oven at maximum rpm in the rotisserie for 10 minutes. The stain solution was removed and the cartridge was washed by adding 200 μl 6×SSPE-T and pipetting this in and out of the cartridge twice. This process was repeated six times. The cartridges were then completely filled with 6×SSPE-T and any bubbles removed. Hybridization, washing and staining was repeated using the same hybridization mixes until both samples had been hybridized to each of the four yeast chip sub-set arrays.

Data Collection

Data was collected by scanning the hybridized chips on a Hewlett-Packard GeneArray scanner. A "halo" effect (appearance of stain non-specifically across the array image) was seen on one of the scanned images: yeast growing in glucose rich media, sub-set C array. Scanning of this array was aborted after one scan and the chip was washed twice with 200 μl 6× SSPE-T and then re-filled as before. This array was then re-scanned three times and the data collected was the average of these three scans. All other arrays were scanned four times without problems and the data collected was the average of the four scans.

EXAMPLE 3

Isolation of promoters and construction of expression vectors.

PCR Amplification of Promoter Regions from Genomic DNA

Based on the *Saccharomyces cerevisiae* genomic sequence in the GenEMBL nucleotide database oligonucleotide primers were designed to amplify the genomic sequence 5' to the following ORFs: YLR110C (Johnston et al. (1997) Nature 1997 May 29; 387(6632 Suppl):87–90), YMR251WA (common name HOR7) (Bowman et al. (1997) Nature May 29; 387(6632 Suppl):90–3), YMR107W (Bowman et al. (1997) Nature May 29; 387(6632 Suppl:90–3), and YOL109W (common name ZEO1) (Dujon et al. (1997) Nature May 29; 387(6632 Suppl):98–102). The region amplified was the non-coding region separating the selected ORF and the next predicted *Saccharomyces cerevisiae* ORF in the 5' direction, with a minimum length of 500 bp.

Sequence of Oligonucleotide Primers Used to Amplify Promoter DNA

HindIII, NheI and NdeI cloning sites underlined.

| | | |
|---|---|---|
| YLR110C-F | ATGCAAGCTTCGCGGCCGCCGTCTGATTTCCGTTT | SEQ ID NO:5 |
| YLR110C-R | CCAGGCCGCATATGTCATATAGTGTTTAAG | SEQ ID NO:6 |
| YMR251WA-F | AGCTAAGCTTCGCGGCCGCCTTTCGATTAGCACGCAC | SEQ ID NO:7 |
| YMR251WA-R | AGATACCTTCATATGTTATTATTAGTC | SEQ ID NO:8 |

-continued

| | | |
|---|---|---|
| YMR107W-F | AGCTAAGCTTCGCGGCCGCGCAGAAATGATGAAGG | SEQ ID NO:9 |
| YMR107W-R | ATCCATCCCATATGTGATATCTCGATTAG | SEQ ID NO:10 |
| ZEO1-F | AGCTAAGCTTCGCGGCCGCGGAGGTCTGCTTCACG | SEQ ID NO:11 |
| ZEO1-R | TACGATCGCATATGTAATTGATATAAACG | SEQ ID NO:12 |

PCR reactions were set up for each primer pair as follows: For YMR251WA and ZEO1 90 μl of Reddy-Load PCR (1.1×) mix, 3.5 mM $MgCl_2$ (Advanced Biotechnologies, cat. no. AB-0628); 2 μl of forward primer (100 μM); 2 μl of reverse primer (100 μM); 1 μl of *S. cerevisiae* genomic DNA (Promega G310A, lot 8347702, 276 μg/ml); and 5 μl of $H_2O$ were combined.

For YLR110C and YMR107W 90 μl of Reddy-Load PCR (1.1×) mix, 1.5 mM $MgCl_2$ (Advanced Biotechnologies, cat. no. AB-0575); 2 μl of forward primer (100 μM); 2 μl of reverse primer (100 μM); 1 μl of *S. cerevisiae* genomic DNA (Promega G310A, lot 8347702, 276 μg/ml); and 5 μl of $H_2O$ were combined.

The thermocycling was carried out as follows: For the YMR251WA promoter: 94° C. for 5 minutes followed by 30 cycles of: 94° C. for 30 seconds, 60° C. for 30 seconds, 72° C. for 1 minute; followed by 72° C. for 5 minutes. The reaction mixtures were then held at 4° C. For the YMR107W and ZEO1 promoters: 94° C. for 5 minutes followed by 30 cycles of: 94° C. for 30 seconds, 45° C. for 30 seconds, 72° C. for 1 minute; followed by 72° C. for 5 minutes. The reaction mixtures were then held at 4° C. For the YLR110C promoter: 94° C. for 5 minutes followed by 30 cycles of: 94° C. for 30 seconds, 50° C. for 30 seconds, 72° C. for 1 minute; followed by 72° C. for 5 minutes. The reaction mixtures were then held at 4° C.

The PCR solutions were loaded onto an LMP gel and the bands were purified using Wizard PCR Preps (Promega, cat. no. A7170) according to protocol, eluted in 50 μl, ethanol precipitated, and resuspended in 20 μl. A map of the YLR110C promoter region is shown in FIG. 13 and SEQ ID NO:29. A map of the YMR251WA promoter region is shown in FIG. 14 and SEQ ID NO:30. A map of the YMR107W promoter region is shown in FIG. 15 and SEQ ID NO:31. A map of the ZEO1 promoter region is shown in FIG. 16 and SEQ ID NO:32.

Cloning Promoter Regions into a Yeast Vector Containing the Luciferase Gene

Figure 2:
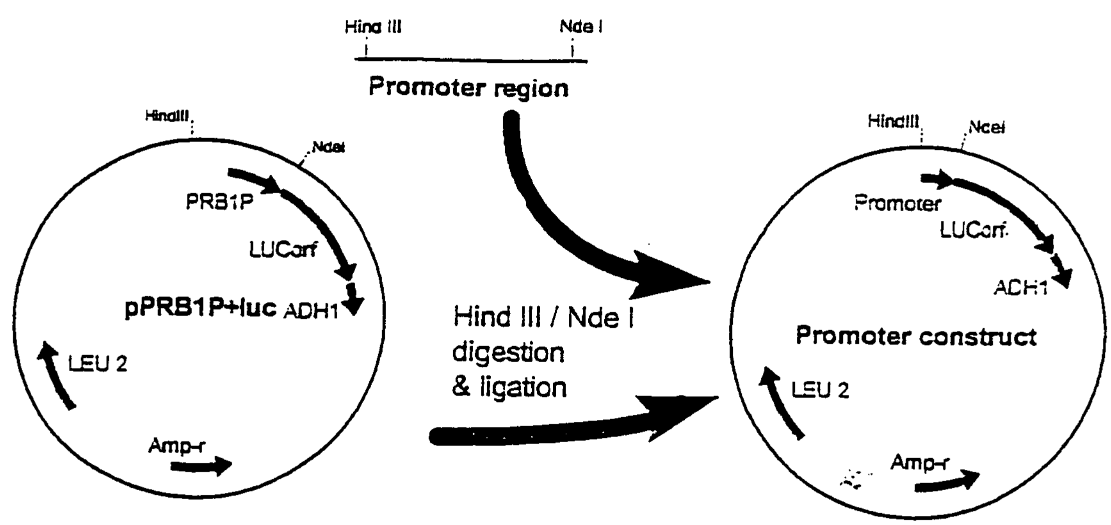
FIG. 2 schematically illustrates construction of YLR110C and YMR251WA promoter constructs.
Figure 3:
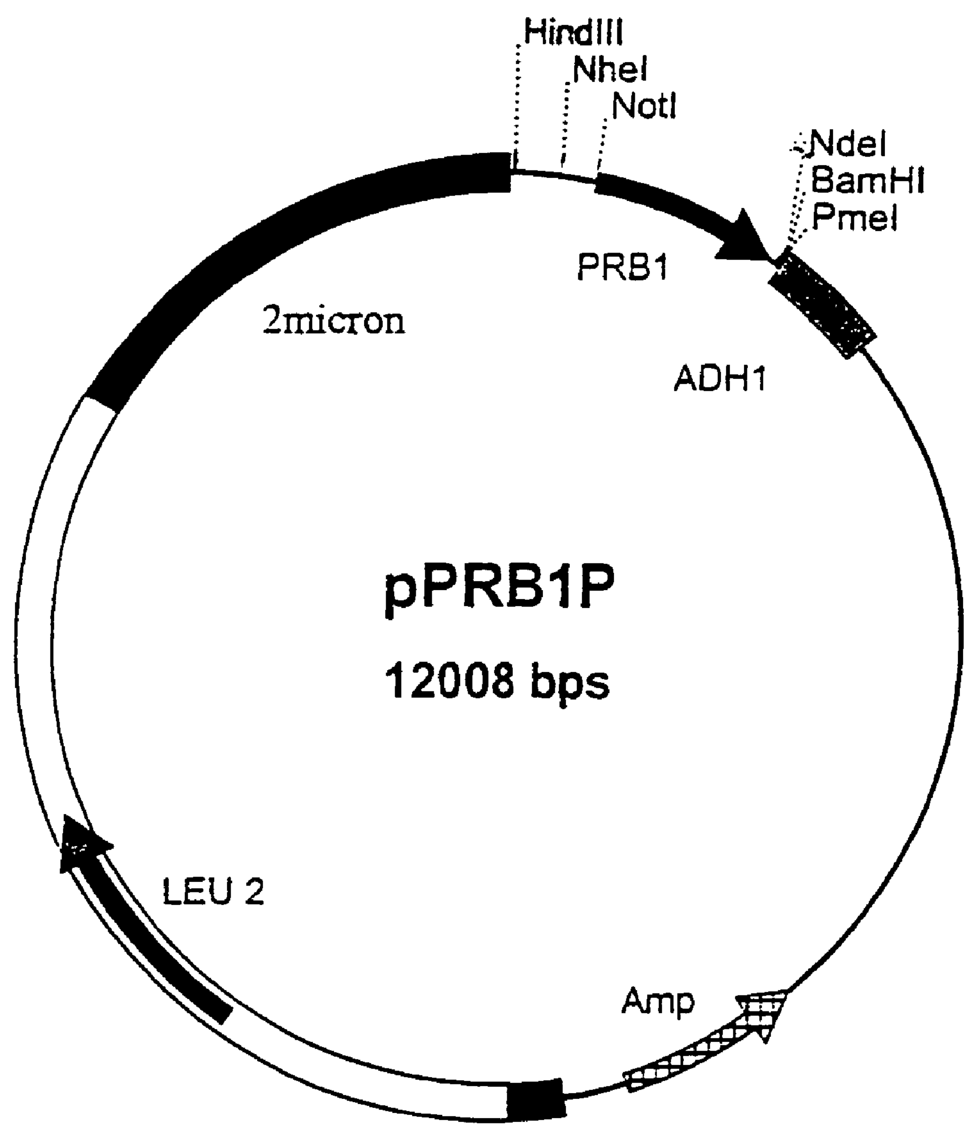
FIG. 3 is a map of pPRB1P.
Figure 4:
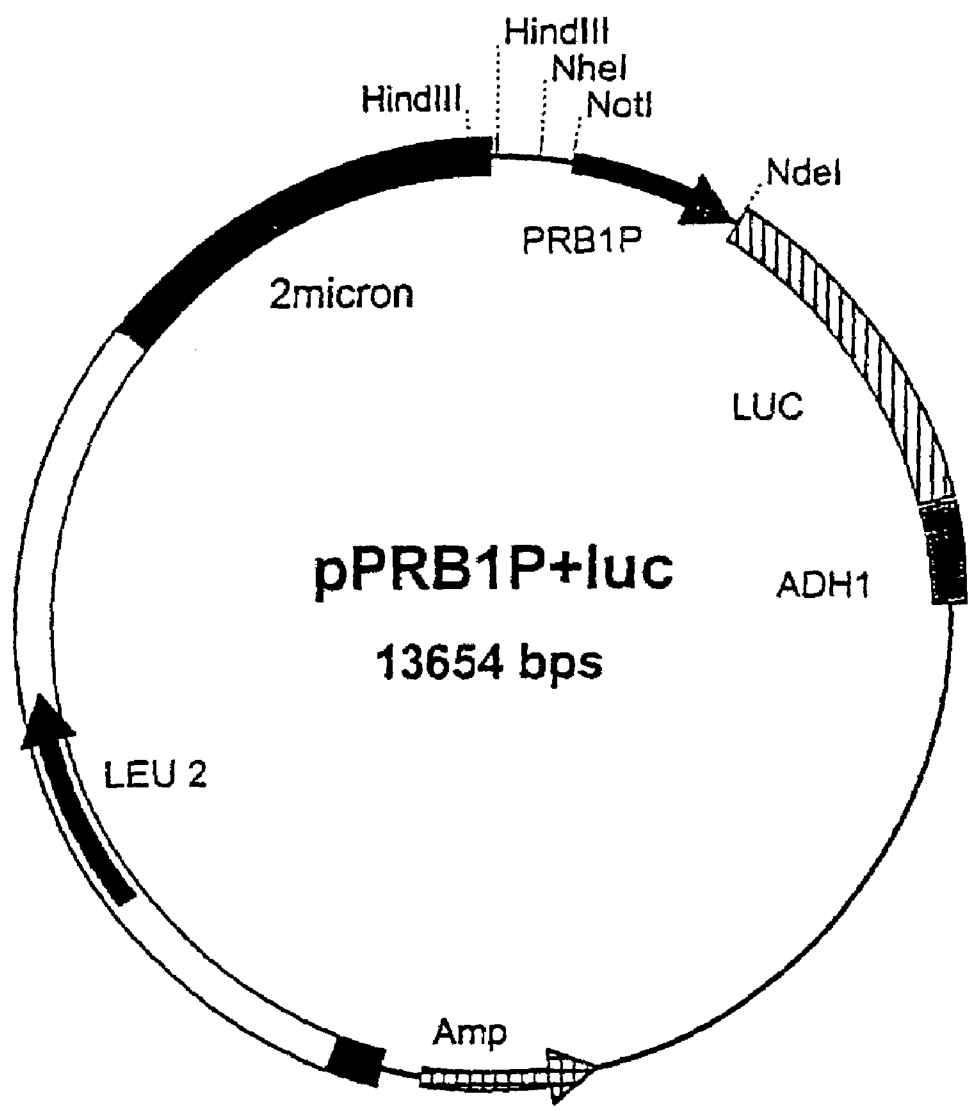
FIG. 4 is a map of pPRB1P+luc.
Figure 5:
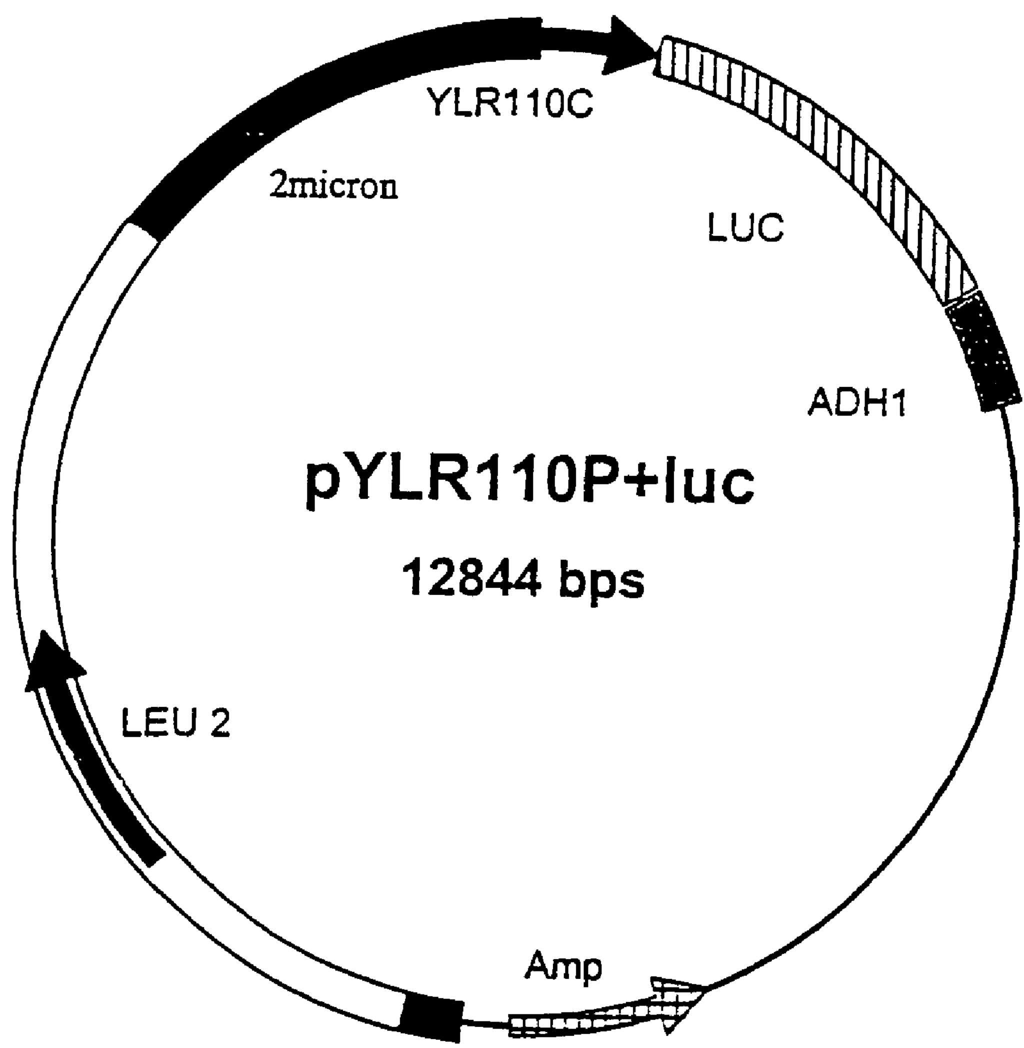
FIG. 5 is a map of pYLR110P+luc.
Figure 6:
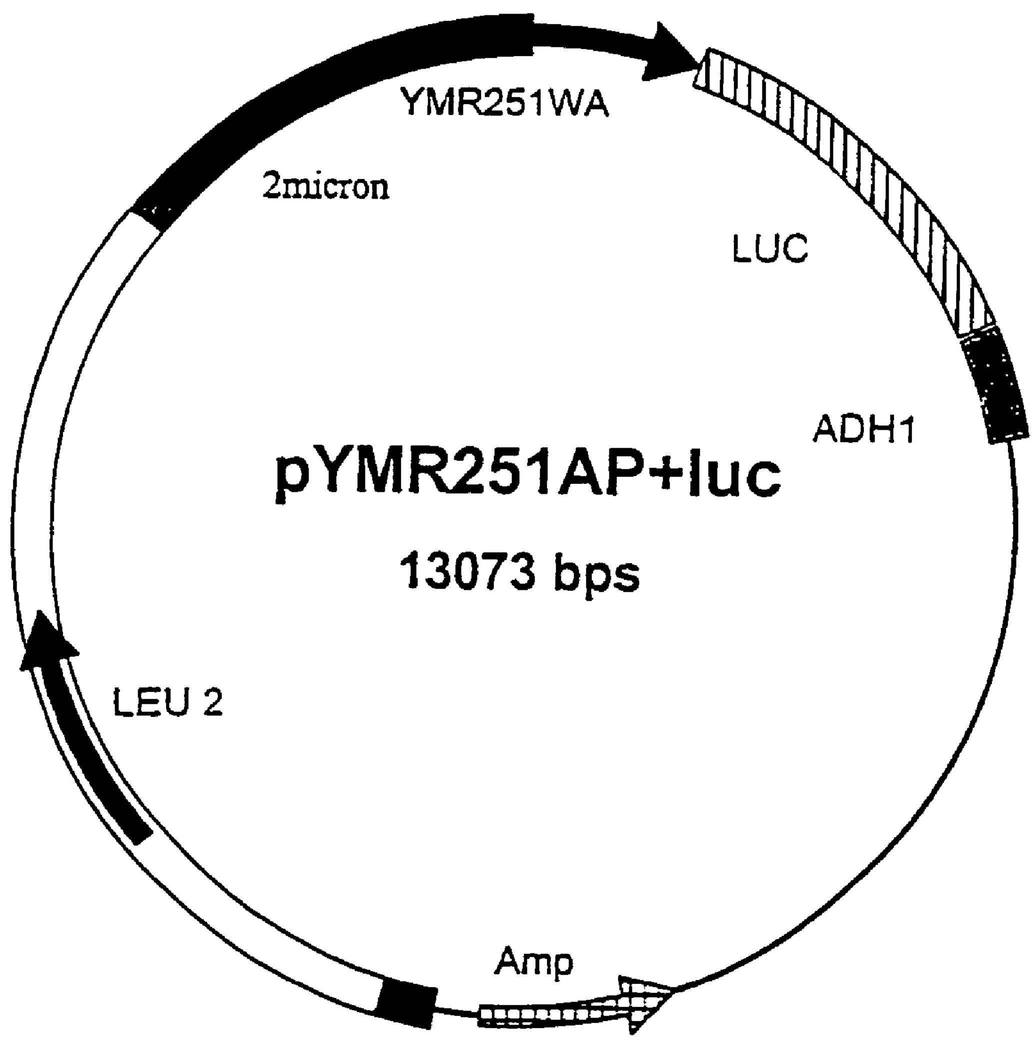
FIG. 6 is a is a map of pYMR251AP+luc.
Figure 7:
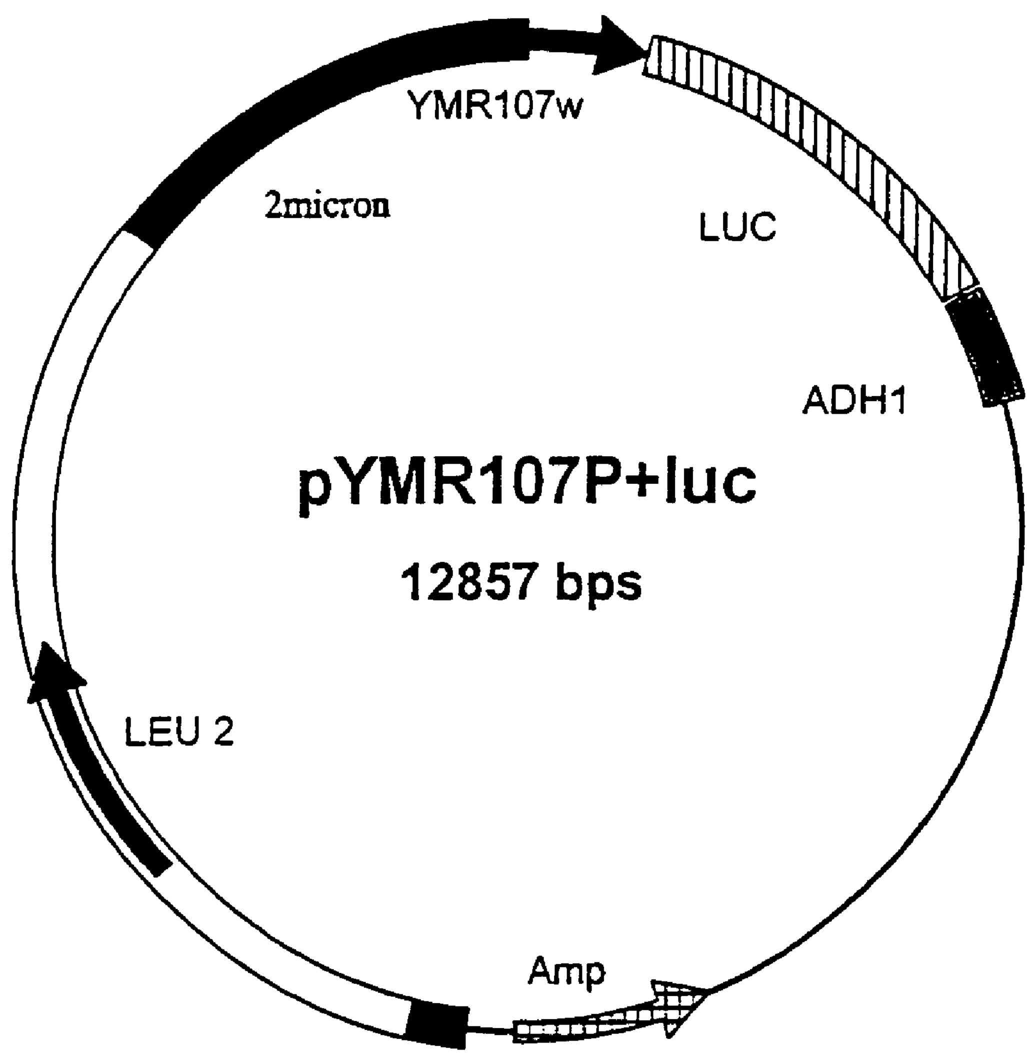
FIG. 7 is a map of pYMR107P+luc.
Figure 8:
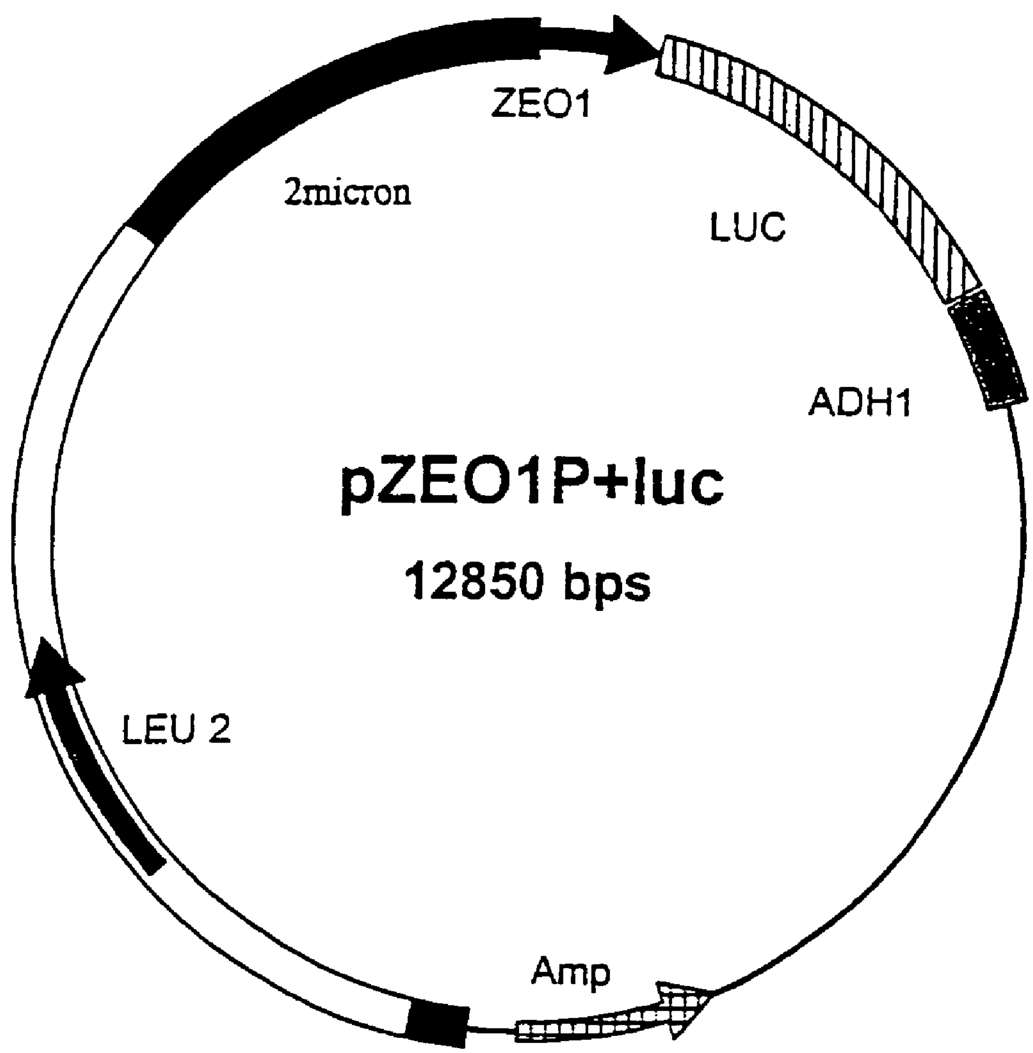
FIG. 8 is a map of pZEO1P+luc.

The PCR products representing the regions upstream of the YLR110C and YMR251WA ORFs were cloned into the suitably digested YEp13-based multicopy yeast expression vector pPRB1P+luc. A map of YEp13 is shown in FIG. 1. The Accession number for YEp13 is U03498. A map of pPRB1P is shown in FIG. 2. The sequence of pPRB1P is shown in SEQ ID NO:27. A map of pPRB1P+luc is shown in FIG. 3 and the sequence is shown in SEQ ID NO:28. The PRB1 promoter was removed from the vector by digesting with the restriction enzymes HindIII and NdeI. The digested backbone was then ligated with a HindIII/NdeI digested PCR product. See FIG. 4.

The PCR products described below, and maxi-prepped pPRB1P+luc were digested as follows. 60 μl of pPRBP1+luc (328 μg/ml), 10 μl of Hind III (Life Technologies, cat. no. 15207-012, 10 units/μl), 10 μl NdeI (Amersham, cat. no. E0216Y, 20 units/μl), 10 μl NEBuffer 2 (NEB, cat. no. 007-2), and 10 μl of $H_2O$. 14 μl YLR110C, 2 μl of Hind III (Life Technologies, cat. no. 15207-012, 10 units/μl), 2 μl Nde I (Amersham, cat. no. E0216Y, 20 units/μl), and 2 μl NEBuffer 2 (NEB, cat. no. 007-2). 14 μl YMR251WA, 2 μl of Hind III (Life Technologies, cat. no. 15207-012, 10 units/μl), 2 μl Nde I (Amersham, cat. no. E0216Y, 20 units/μl), and 2 μl NEBuffer 2 (NEB, cat. no. 007-2). The solutions were allowed to react at 37° C., for 4 hours.

The double digested pPRB1P+luc backbone was purified on an LMP gel using Wizard PCR preps (Promega, cat. no. A7170), and then ethanol precipitated. The remaining digestion products were also ethanol precipitated. The pPBR1P+luc digests were resuspended in 60 μl of $H_2O$ and the PCR product digests were resuspended in 20 μl.

Ligation reactions were then carried out between each promoter region and the digested pPRBP1+luc at 16° C. overnight. The PCR products representing the regions upstream of the following ORFs: YMR107W and ZEO1, were prepared, restricted, and ligated essentially as described above, however BCL restriction buffer B and different amounts of PCR product/volumes were used.

Transformation of Ligation Products into *E. coli*

The products of the ligations described above were transformed into *E. coli* (Invitrogen's One-Shot TOP10 Competent cells, cat. no. C4040-10) according to manufacturers protocol. In each case 5 μl of the ligation product was added to the cell suspension. The total final cell suspension was plated out onto L-amp plates and incubated overnight at 37° C.

Colonies were picked from the plates and PCR screened using the PCR primers used to amplify the promoters originally. Two positive colonies from each ligation were grown in 5 ml overnight cultures and their plasmids were purified (Promega Wizard Plus SV Mini-preps, cat. no. A1330). The eluted DNA was ethanol precipitated and resuspended in 20 μl of water. Analytical restriction digests were carried out to confirm the presence of the correct promoter. Clones containing all four promoter constructs were obtained.

The new constructs were named as follows:

| | |
|---|---|
| *pPRB*1+*luc* backbone+*YLR*110*C* promoter=*pYLR*110*P*+*luc* | SEQ ID NO:19 |
| *pPRB*1+*luc* backbone+*YMR*251*WA* promoter=*pYMR*251*AP*+*luc* | SEQ ID NO:20 |
| *pPRB*1+*luc* backbone+*YMR*107*W* promoter=*pYMR*107*P*+*luc* | SEQ ID NO:21 |
| *pPRB*1+*luc* backbone+*ZEO*1 promoter=*pZEO*1*P*+*luc* | SEQ ID NO:22 |

Maps of pYLR110P+luc, pYMR251AP+luc, pYMR107P+luc, and pZEO1P+luc are shown in FIGS. 5, 6, 7, and 8, respectively. Plasmid DNA (pYLR110P+luc and pYMR251AP+luc) was prepared for transformation into yeast and sequencing using the QIAGEN Plasmid Maxi kit (Cat. no. 12162). The DNA concentrations of the maxi-preps (measured by absorbance at 260 nm) were: pYLR110P+luc 463 μg/ml; pYMR251AP+luc 346 μg/ml; pYMR107P+luc ~300 μg/ml; and pZEO1P+luc ~720 μg/ml. The remaining plasmids were transformed into yeast as Wizard Plus SV Mini-prep DNA, and maxi-prep DNA was obtained for sequencing using the Gibco BRL Concert Plasmid Maxi kit (Cat no. 11452).

Sequencing of Promoter Constructs

DNA of each of the four promoter constructs were sequenced using the ABI PRISM BigDye Terminator Cycle Sequencing Kit (PE Applied Biosystems, part no. 4303153) was used to carry out the sequencing reactions. Each reaction contained 8 μl of Reaction Mix and 1 μl of 3.2 μM primer. The volumes of template DNA and $H_2O$ added are as follows: 1.1 μl of pYLR110P+luc template and 9.9 μl of water; 1.4 μl of pYMR251AP+luc template and 9.6 μl of water; 2.0–6.0 μl of pYMR107P+luc template and 9.0–5.0 μl of water; and 0.5–1.5 μl of pZEO1P+luc template and 10.5–9.5 μl of water.

The thermocycling protocol is described in the ABI protocol, the PCR products were ethanol precipitated by adding 3M NaOAc and absolute Ethanol, standing at room temperature for 15 minutes, centrifuging for 20 minutes and washing with 250 μl of 70% ethanol. The precipitated DNA was resuspended in 3 μl of loading dye and 2 μl of each suspension was analyzed on an PE-ABI 377 automated sequencer.

The following promoter constructs pYLR110P+luc and pYMR251AP+luc were each sequenced using four primers:

Yep13 F2: CCTCAATTGGATTAGTCTCA—SEQ ID NO:13—aligns to the YEp13 backbone, 290 bp 5' of the Hind III site.

Luc R1: CACCTCGATATGTGCATCTG—SEQ ID NO:14—aligns to the Luc ORF, 150 bp 3' of the NdeI site.

Forward PCR primer: forward primer used to PCR clone promoter, i.e., SEQ ID NO:5 and SEQ ID NO:7.

Reverse PCR primer: reverse primer used to PCR clone promoter, i.e., SEQ ID NO:6 and SEQ ID NO:8.

The remaining promoter constructs (pYMR107P+luc and pZEO1P+luc) were each sequenced using primers Yep13 F2 and Luc R1. Combining the data from all primers completely sequenced the promoter regions and spanned the cloning sites of the original vector.

Deviations from Published Genomic Sequences

All sequences differ by a few base pairs around the ATG, this results from the creation of an NdeI site at the 3'end of the promoter. In addition, the following further alterations from published sequences were identified.

pYLR110P+luc: A substitution of a C for a T had taken place at a base pair 361 of the sequence.

pYMR107P+luc: In the initial construct (for which luciferase reporter data is described), a cloning artifact led to the junction between the promoter region and the LUC ORF in pYMR107W+luc to have the sequence: CATAT<u>ATG</u> (where ATG is the luciferase translational start site). This sequence was modified by site directed mutagenesis to create the sequence CAT<u>ATG</u>, which generates a novel NdeI site at the promoter/luciferase junction. Subsequent luciferase expression analysis confirmed that expression from the NdeI site modified pYMR107P+luc construct did not differ significantly from the original construct, therefore the sequence of the corrected CAT<u>ATG</u> construct is included herein.

Other Modifications pYMR107P+luc: Cloning artifacts created in additional HindIII site and linker to the 5' (i.e. outside) of the pYMR107P+luc and promoters:

```
hindIII  NotI        promoter 5'=
AAGCTT-CGCGGCCGCG-NNNNNNN              SEQ ID NO:17
The sequence is:
hindIII     hindIII  NotI       promoter 5'=
AAGCTT-AGCT-AAGCTT-CGCGGCCGCG-NNNNNNN. SEQ ID NO:18
```

EXAMPLE 4

Luciferase Assays of Promoter Activity

Transformation of *S. cerevisiae* with promoter constructs.

*S. cerevisiae* strain 11C was transformed with five promoter constructs. This strain carries six metabolic markers, Ade, Trp, Ura, Lys, Leu and His. It has the genotype ade2-161, trp1-D63, ura3-52, lys2-801, leu2D1 &/or leu2-3 &/or leu2-112, hisD200 &/or hisD200. 11C was generated by crossing the strains YPH500 (Mat a ura3-52 lys2-801 ade2-161 trp1-D63 hisD200 leu2D1) and AH22 (MATa leu2-3 leu2-112 his4-519 can1.

11C cells were streaked from a glycerol stock onto a YPD plate and grown at 30° C. for two days. The cells were transformed with the five plasmids. pYLR110P+luc, pYMR251AP+luc, pYMR107P+luc, & pZEO1P+luc and pPRB1P+luc to act as a control. The transformations were carried out using the Quick and Easy method (Gietz, R. D. and R. A. Woods, 1994, *Molecular Genetics of Yeast: Practical Approaches* pp. 121–134. 10 ml of plasmid was added to the transformation mix in each case. The whole transformation mixes were plated out onto -Leu plates and incubated at 30° C. for three days. Three individual colonies from each transformation plate were picked and used to inoculate 10 ml YPD cultures. The 10 ml cultures were incubated in an orbital shaker set to 200 rpm and 30° C. Cells were harvested from the cultures at two points. First, at a point at which the OD of the culture was close to 1.0, at which time a 4 ml sample was taken. Second, a 3 ml sample was taken after an incubation time of 45 hours. The ODs and incubation time of each sample is shown in Table 5. For all harvested samples, the cells were immediately spun down at 3000 rpm and 4° C., washed in 5 ml of $dH_2O$, repelleted and frozen at −20° C.

TABLE 5

| Plasmid | Clone number | OD at time of harvesting first 4 ml sample | Incubation time at harvesting of first sample (hours) | OD at time of harvesting second 3 ml sample |
|---|---|---|---|---|
| pPRB1P + luc | 7 | 0.98 | 24.5 | 4.80 |
| | 8 | 0.68 | 28 | 5.56 |
| | 9 | 1.15 | 28 | 5.66 |
| pYLR110P + luc | 8 | 1.12 | 28 | 5.50 |
| | 9 | 0.46 | 28 | 4.38 |
| | 10 | 1.16 | 24.5 | 5.51 |
| pYMR251AP + luc | 8 | 1.20 | 24.5 | 4.99 |
| | 9 | 1.05 | 27 | 4.71 |
| | 10 | 1.15 | 27 | 5.18 |
| pYMR107P + luc | 1 | 1.06 | 27 | 5.47 |
| | 2 | 0.49 | 28.5 | 4.54 |
| | 3 | 0.97 | 25.5 | 5.58 |
| pZEO1P + luc | 1 | 1.02 | 28.5 | 4.84 |
| | 2 | 0.62 | 28.5 | 4.97 |
| | 3 | 0.42 | 28.5 | 4.31 |

Analysis of Luciferase Activity

All of the samples were analyzed for luciferase activity, using the LucLite Luciferase Reporter Gene Assay Kit (Packard, cat. no 6016911). The cells were prepared by resuspending in PBS and diluting to a final concentration of $6\times10^6$ cells/ml. 100 ml of each cell suspension was pipetted into wells in duplicate on two 96 well plates, so that each well contained $6\times10^5$ cells. The plates were incubated at 30° C. for 10 minutes. 100 ml of a 1 in 2 dilution of reconstituted substrate was added to each well, and the plate was further incubated at room temperature for 10 minutes. The luminescence was then measured using the Packard TopCount. The luminescence readings obtained after 0.03 min are shown below in counts per second (CPS) in Table 6.

HindIII and NdeI to obtain the vector. The promoter+luc construct was digested with HindIII and NdeI to obtain the promoter fragment. The vector and promoter DNA was purified from LMP agarose using PCRpreps. The vector and promoter was ligated and used to transform *E. coli.* Correct recombinants were screened for.

EXAMPLE 5

Isolation of Active Promoter Fragments

Operative fragments of the YLR110C, YMR251WA, YMR107W and ZEO1 promoters can be generated using restriction endonucleases, 5' or 3' deletion mutagenesis, PCR, site specific deletion, or a combination thereof. For

TABLE 6

| | Clone | First sample | | | | Second sample | | | |
|---|---|---|---|---|---|---|---|---|---|
| Plasmid | number | Readings | (CPS) | Average | Average | Readings | (CPS) | Average | Average |
| pPRB1P + luc | 7 | 35890 | 35690 | 35790 | 34898 | 20322 | 20975 | 20648 | 19867 |
| | 8 | 25498 | 25276 | 25387 | 24495 | 52997 | 51778 | 52388 | 51607 |
| | 9 | 24137 | 27797 | 25967 | 25075 | 49192 | 46971 | 48081 | 47300 |
| pYLR110P + luc | 8 | 52354 | 53618 | 52986 | 52094 | 41789 | 38904 | 40346 | 39565 |
| | 9 | 105299 | 99776 | 102537 | 101645 | 85562 | 84468 | 85015 | 84234 |
| | 10 | 107531 | 109226 | 108379 | 107486 | 22507 | 22436 | 22471 | 21690 |
| pYMR251AP + luc | 8 | 71993 | 69797 | 70895 | 70003 | 40869 | 40202 | 40536 | 39755 |
| | 9 | 98853 | 98389 | 98621 | 97729 | 51159 | 49828 | 50493 | 49712 |
| | 10 | 83210 | 87546 | 85378 | 84485 | 70091 | 74576 | 72334 | 71553 |
| pYMR107P + luc | 1 | 9046 | 8650 | 8848 | 6790 | 29413 | 28505 | 28959 | 28124 |
| | 2 | 3996 | 4009 | 4002 | 1945 | 24391 | 23915 | 24153 | 23318 |
| | 3 | 3018 | 3236 | 3127 | 1069 | 23866 | 23408 | 23637 | 22802 |
| pZEO1P + luc | 1 | 64137 | 63162 | 63649 | 61592 | 47469 | 45769 | 46619 | 45784 |
| | 2 | 19579 | 18329 | 18954 | 16897 | 44910 | 42982 | 43946 | 43111 |
| | 3 | 87572 | 90317 | 88944 | 86887 | 142414 | 142262 | 142338 | 141503 |

The results are summarized in Table 7.

TABLE 7

| Promoter | mRNA levels | Luciferase Expression Glucose | Luciferase Expression Ethanol |
|---|---|---|---|
| PRB1 | Ethanol Induced | 1.00 | 1.00 |
| YLR110C | Highly Ethanol and Glucose Induced | 3.03 | 1.22 |
| YMR251WA | Highly Ethanol and Glucose Induced | 2.92 | 1.35 |
| YMR107W | Ethanol Induced | 0.21 | 0.95 |
| ZEO1 | Very Highly Ethanol and Glucose Induced | 3.62 | 2.89 |

Three promoters give higher levels of expression than PRB1 at both ODs, these are: YLR110C, YMR251WA, and ZEO1. The promoter showing the greatest fold induction is YMR107W.

Creating Vectors with Promoters but without the Luciferase Gene

Figure 9:
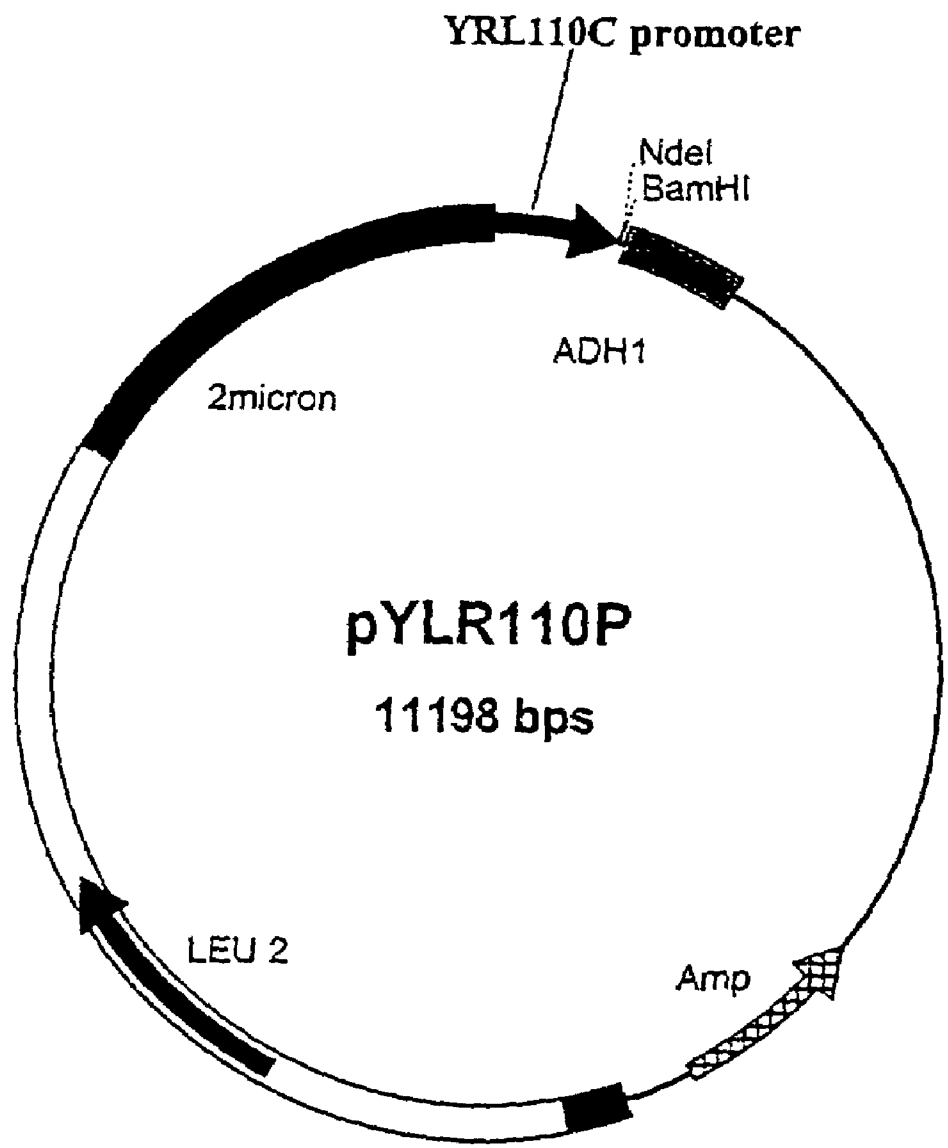
FIG. 9 is a map pYLR110P.
Figure 10:
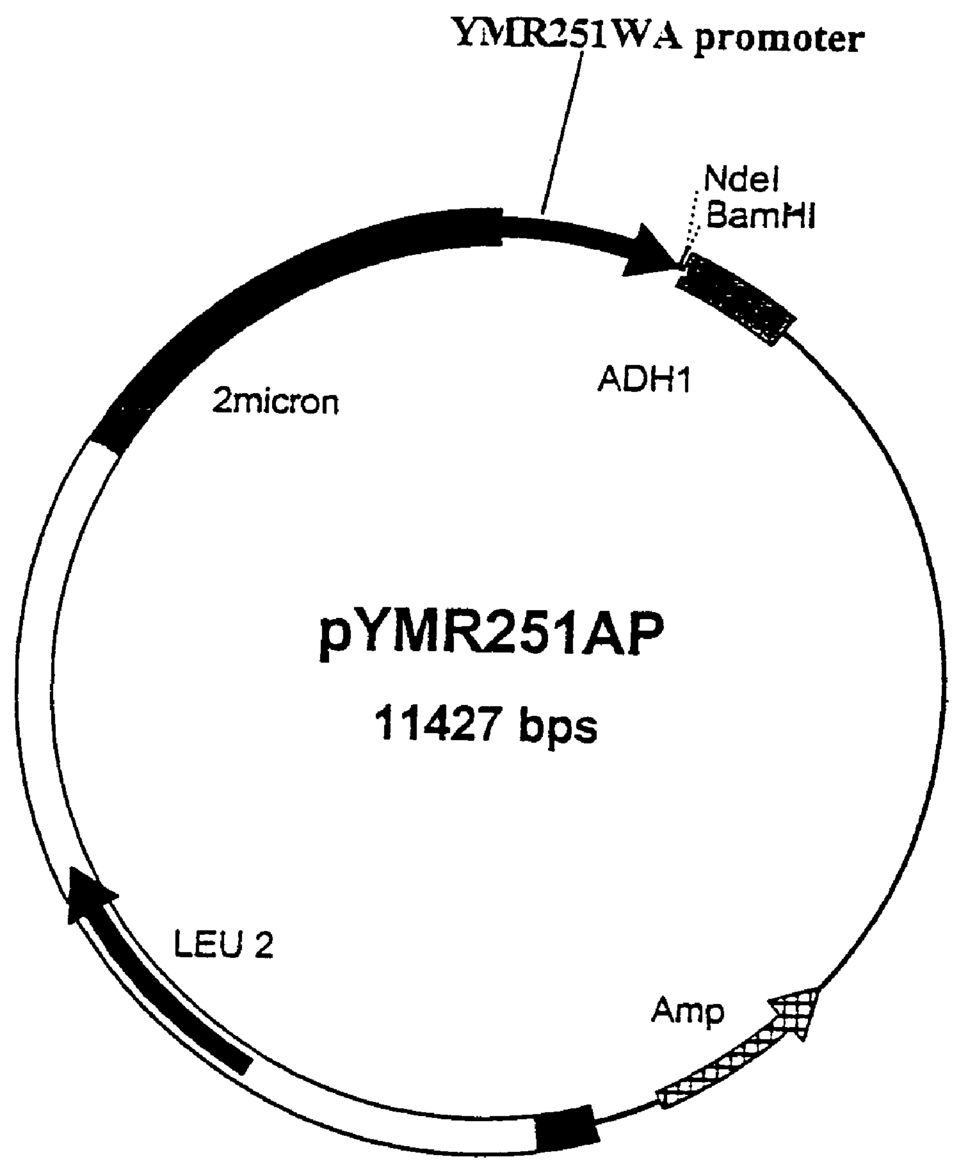
FIG. 10 is a map of pYMR251AP.
Figure 11:
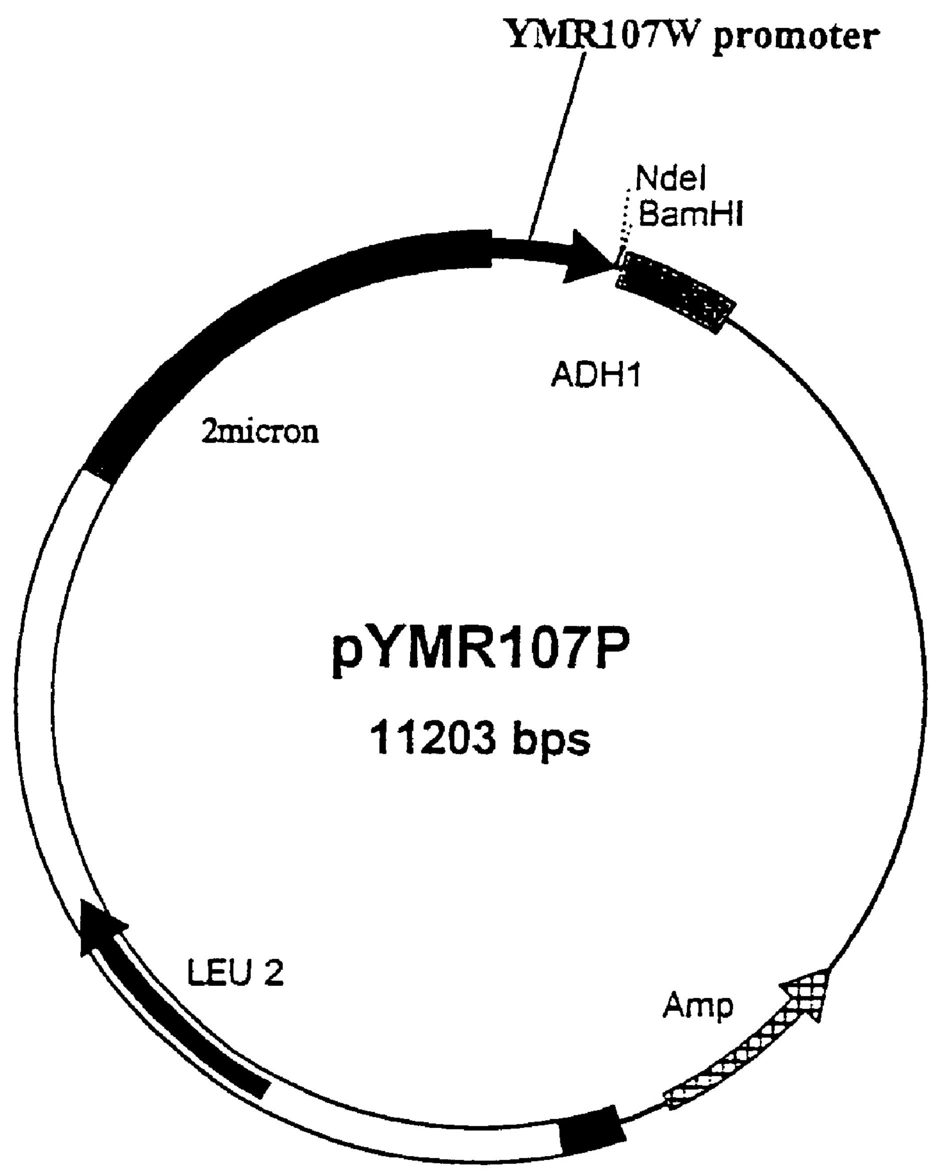
FIG. 11 is a map of pYMR107P.
Figure 12:
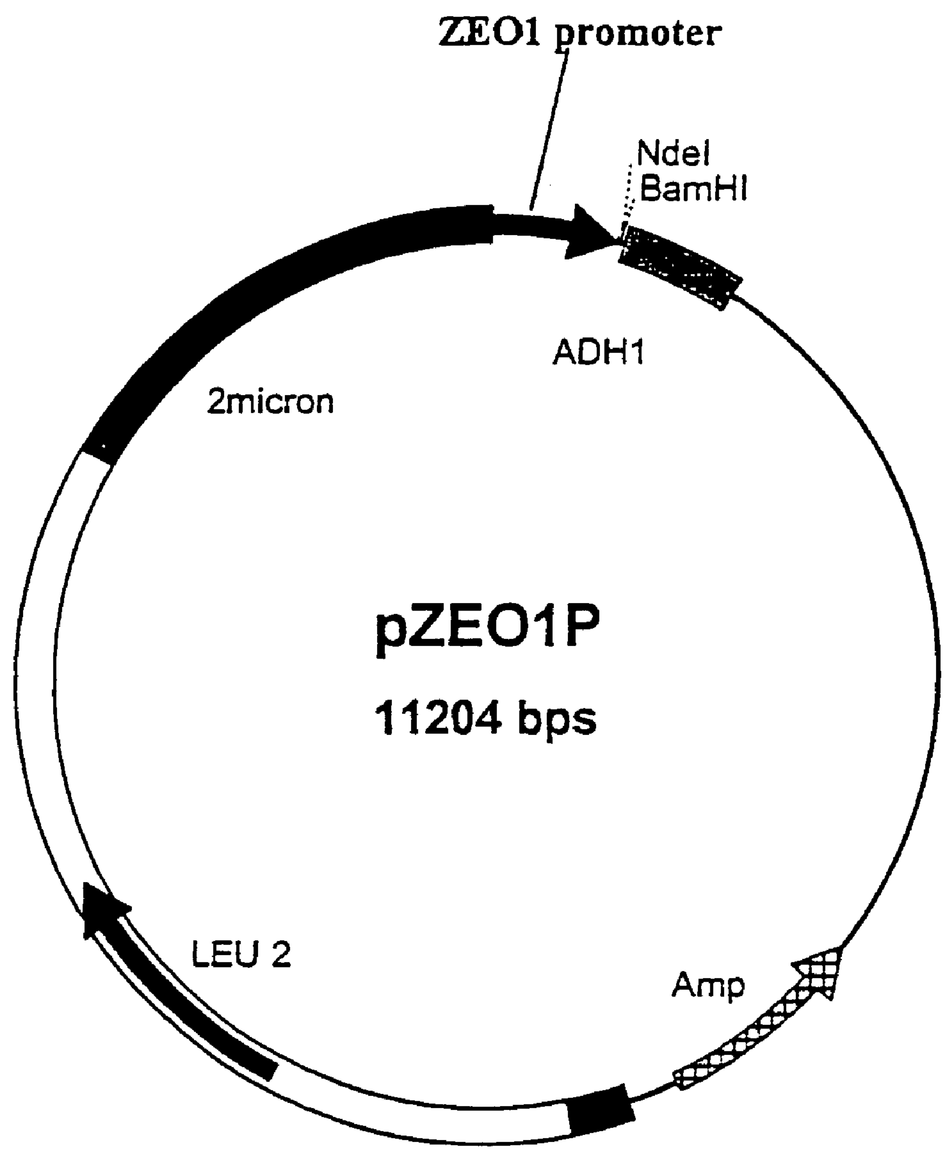
FIG. 12 is a map of pZEO1P.

Based on the analysis of luciferase expression four further promoter constructs have been made. The lack the luciferase gene and can be used to clone nucleic acid molecules encoding polypeptides of interest downstream of the promoters such that they drive expression of the nucleic molecules of interest. The sequences of these four plasmids are named: G1: pYLR110P (SEQ ID NO:23) (map at FIG. 9); G2: pYMR251AP (SEQ ID NO:24) (map at FIG. 10); G3 pYMR107P (SEQ ID NO:25) (map at FIG. 11); and G4: pZEO1P (SEQ ID NO:26) (map at FIG. 12). These were constructed by digesting pPRB1P (SEQ ID NO:27) with example, purified pYLR110P+luc, pYMR251AP+luc, pYMR107P+luc or pZEO1P+luc plasmids, as generated in Example 3, can be subjected to restriction endonucleases to generate fragments of the YLR110C, YMR251WA, YMR107W or ZEO1 promoters. Restriction endonuclease sites, preferably unique restriction endonuclease sites, within the promoter sequences shown in SEQ ID NO:1, SEQ ID NO:2, SEQ ID NO:3, and SEQ ID NO:4 can be identified that generate fragments of the promoter upon restriction endonuclease digestion. Such fragments are preferably, 17, 25, 50, 75, 100, 150, 200, 250, 300, 350, 400, 450, 500, 550, 600, 650 or 700 nucleotides in length.

The fragments generated by restriction endonuclease digestion of the promoters shown in SEQ ID NO:1, SEQ ID NO:2, SEQ ID NO:3, or SEQ ID NO:4 can be separated by agarose gel electrophoresis. The agarose gel band corresponding to the desired promoter fragment can be cut out of the agarose gel. The fragment can be isolated and purified from the agarose gel by, for example, electroelution or kits such as QIAquick™ gel extraction kit or QIAEX® II Gel Extraction System (Qiagen Cat. No. 28704 and 20021).

The purified promoter fragment can be ligated into the isolated and purified HindIII, NdeI, double-digested pPRBP1+luc backbone such that the promoter fragment is operably linked to a luciferase gene and transformed into *E. coli,* as described in Example 3. The new expression vector comprising a fragment of YLR110C, YMR251WA, YMR107W, or ZEO1 promoter region can be isolated and purified from *E. coli,* sequenced, and transformed into yeast as described in Example 3.

To analyze promoter activity, luciferase assays as described in Example 4, can be conducted using *S. cerevi-*

*siae* cultures that have been transformed with the expression vector comprising a fragment of the YLR110C, YMR251WA, YMR107W, or ZEO1 promoter operably linked to a luciferase gene and *S. cerevisiae* cultures that have been transformed with pPRB1P+luc. The *S. cerevisiae* cultures are grown in medium containing a non-fermentable carbon source, such as ethanol, or a fermentable carbon source, such as glucose, or both. Cells are obtained from the cultures and analyzed for luciferase activity as described in Example 4.

A promoter fragment is operative if it expresses at least 75% of the luciferase activity as the PRB1 promoter. Preferably, an operative promoter fragment expresses at least 9100%, 200%, 300%, 400%, or more of the luciferase activity as the PRB1 promoter.

BRIEF DESCRIPTION OF THE SEQUENCES

SEQ ID NO:1 Polynucleotide sequence of promoter YLR110C

SEQ ID NO:2 Polynucleotide sequence of promoter YMR251WA

SEQ ID NO:3 Polynucleotide sequence of promoter YMR107W

SEQ ID NO:4 Polynucleotide sequence of promoter ZEO1

SEQ ID NO:5 Forward PCR primer for YLR110C

SEQ ID NO:6 Reverse PCR primer for YLR110C

SEQ ID NO:7 Forward PCR primer for YMR251WA

SEQ ID NO:8 Reverse PCR primer for YMR251WA

SEQ ID NO:9 Forward PCR primer for YMR107W

SEQ ID NO:10 Reverse PCR primer for YMR107W

SEQ ID NO:11 Forward PCR primer for ZEO1

SEQ ID NO:12 Reverse PCR primer for ZEO1

SEQ ID NO:13: Yep13 Forward PCR primer

SEQ ID NO:14: Luc RI Forward PCR primer

SEQ ID NO:15 Primer used in cDNA sequencing

SEQ ID NO:16 Control oligonucleotide used in GeneChip Microarray assay

SEQ ID NO:17 Original pYMR107P+luc sequence

SEQ ID NO:18 Modified pYMR107P+luc sequence

SEQ ID NO:19 Nucleotide sequence of pYLR110P+luc

SEQ ID NO:20 Nucleotide sequence of pYMR251AP+luc

SEQ ID NO:21 Nucleotide sequence of pYMR107P+luc

SEQ ID NO:22 Nucleotide sequence of pZEO1P+luc

SEQ ID NO:23 Nucleotide sequence of pYLR110P

SEQ ID NO:24 Nucleotide sequence of pYMR251AP

SEQ ID NO:25 Nucleotide sequence of pYMR107P

SEQ ID NO:26 Nucleotide sequence of pZEO1P

SEQ ID NO:27 Nucleotide sequence of pPRB1P

SEQ ID NO:28 Nucleotide sequence of pPRB1P+luc

SEQ ID NO:29 YLR110C promoter region

SEQ ID NO:30 YMR251WA promoter region

SEQ ID NO:31 YMR107W promoter region

SEQ ID NO:32 ZEO1 promoter region.

The invention claimed is:

1. An isolated and purified polynucleotide consisting of SEQ ID NO:2, wherein the polynucleotide is operative as a promoter to express a nucleic acid molecule encoding a polypeptide when operably linked to said nucleic acid molecule.

2. A yeast expression vector comprising the polynucleotide of claim 1.

3. The yeast expression vector of claim 2 wherein the yeast expression vector is selected from the group consisting of pYMR251AP+luc, and pYMR251AP.

4. A yeast cell transformed with the yeast expression vector of claim 2.

5. A yeast cell transformed with the yeast expression vector of claim 3.

6. A method for producing a polypeptide comprising the steps of:

(a) constructing a yeast expression vector wherein a nucleic acid encoding the polypeptide is controlled by the polynucleotide of claim 1;

(b) transforming a culture of yeast cells with the yeast expression vector;

(c) maintaining the yeast cells in culture so that the polypeptide is expressed; and (c) recovering the polypeptide.

7. A method for producing a polypeptide comprising the steps of:

(a) cloning a nucleic acid molecule encoding the polypeptide into an expression vector selected from the group consisting of pYMR251AP+luc, and pYMR251AP, wherein the nucleic acid molecule is operably linked to a promoter of the expression vector;

(b) transforming a culture of yeast cells with the yeast expression vector;

(c) maintaining the yeast cells in culture so that the polypeptide is expressed; and (d) recovering the polypeptide.

8. A method for producing a polypeptide comprising the steps of:

(a) constructing a yeast expression vector wherein a nucleic acid molecule encoding the polypeptide is controlled by, the polynucleotide of claim 1;

(b) transforming a culture of yeast cells with the yeast expression vector;

(c) maintaining the yeast cells in culture medium and controlling the expression of the nucleic acid molecule encoding the polypeptide by varying the level of a fermentable carbon source in the culture medium; and (d) recovering the polypeptide.

9. The method of claim 8 wherein the fermentable carbon source is glucose.

10. A method for producing a polypeptide comprising the steps of:

(a) constructing a yeast expression vector wherein a nucleic acid molecule encoding the polypeptide is controlled by the polynucleotide of claim 1;

(b) transforming a culture of yeast cells with the yeast expression vector;

(c) maintaining the yeast cells in culture medium and controlling the expression of the nucleic acid molecule encoding the polypeptide by varying the level of a non-fermentable carbon source in the culture medium; and (d) recovering the polypeptide.

11. The method of claim 10 wherein the non-fermentable carbon source is ethanol.

12. A method for producing a polypeptide comprising the steps of:

(a) constructing a yeast expression vector wherein a nucleic acid molecule encoding the polypeptide is controlled by the polynucleotide of claim 1;

(b) transforming a culture of yeast cells with the yeast expression vector;

(c) maintaining the yeast cells in culture medium and controlling the expression of the nucleic acid molecule encoding the polypeptide by varying the level of a fermentable carbon source and a non-fermentable carbon source in the culture medium; and (d) recovering the polypeptide.

13. The method of claim 12 wherein the fermentable carbon source is glucose.

14. The method of claim 12 wherein the non-fermentable carbon source is ethanol.

15. A method of identifying a promoter fragment, wherein the fragment has promoter activity comprising the steps of:

(a) generating a fragment comprising at least 17 contiguous nucleotides of an isolated and purified polynucleotide consisting of SEQ ID NO:2;

(b) cloning the fragment into a yeast expression vector, wherein the fragment is operably linked to a reporter gene;

(c) transforming yeast cells with the yeast expression vector;

(d) growing the yeast cells in yeast cell culture under conditions favorable for expression of the reporter gene; and (e) assaying the yeast culture for a reporter protein expressed by the reporter gene;

wherein expression of the reporter gene indicates the fragment has promoter activity.

* * * * *

SEQUENCE LISTING

```
<160> NUMBER OF SEQ ID NOS: 32

<210> SEQ ID NO 1
<211> LENGTH: 494
<212> TYPE: DNA
<213> ORGANISM: Saccharomyces cerevisiae

<400> SEQUENCE: 1

cgtctgattt ccgttttggg aatcctttgc cgcgcgcccc tctcaaaact ccgcacaagt     60

cccagaaagc gggaaagaaa taaaacgcca ccaaaaaaaa aaaaataaaa gccaatcctc    120

gaagcgtggg tggtaggccc tggattatcc cgtacaagta tttctcagga gtaaaaaaac    180

cgtttgtttt ggaattcccc atttcgcggc cacctacgcc gctatctttg caacaactat    240

ctgcgataac tcagcaaatt ttgcatattc gtgttgcagt attgcgataa tgggagtctt    300

actcccaaca taacggcaga aagaaatgtg agaaaatttt gcatcctttg cctccgttca    360

agtatataaa gtcggcatgc ttgataatct ttctttccat cctacattgt tctaattatt    420

cttattctcc tttattcttt cctaacatac caagaaatta atcttctgtc attcgcttaa    480

acactatatc acat                                                      494


<210> SEQ ID NO 2
<211> LENGTH: 723
<212> TYPE: DNA
<213> ORGANISM: Saccharomyces cerevisiae

<400> SEQUENCE: 2

ctttcgatta gcacgcacac acatcacata gactgcgtca taaaaataca ctacggaaaa     60

accataaaga gcaaagcgat acctacttgg aaggaaaagg agcacgcttg taagggggat    120
```

-continued

```
gggggctaag aagtcattca ctttcttttc ccttcgcggt ccggacccgg gacccctcct    180

ctccccgcac gatttcttcc tttcatatct tccttttatt cctatcccgt tgaagcaacc    240

gcactatgac taaatggtgc tggacatctc catggctgtg acttgtgtgt atctcacagt    300

ggtaacggca ccgtggctcg gaaacggttc cttcgtgaca attctagaac aggggctaca    360

gtctcgataa tagaataata agcgcatttt tgctagcgcc gccgcggcgc ccgtttccca    420

atagggaggc gcagtttatc ggcggagctc tacttcttcc tatttgggta agcccctttc    480

tgttttcggc cagtggttgc tgcaggctgc gccggagaac atagtgataa gggatgtaac    540

tttcgatgag agaattagca agcggaaaaa aactatggct agctgggagt tgtttttcaa    600

tcatataaaa gggagaaatt gttgctcact atgtgacagt ttctgggacg tcttaacttt    660

tattgcagag gactatcaaa tcatacagat attgtcaaaa aaaaaaaaga ctaataataa    720

cat                                                                  723
```

<210> SEQ ID NO 3
<211> LENGTH: 497
<212> TYPE: DNA
<213> ORGANISM: Saccharomyces cerevisiae

<400> SEQUENCE: 3

```
gcagaaatga tgaagggtgt tagcgccgtc cactgatgtg cctggtagtc atgatttacg     60

tataactaac acatcatgag gacggcggcg tcaccccaac gcaaaagagt gacttccctg    120

cgctttgcca aaaccccata catcgccatc tggctcctgg cagggcggtt gatggacatc    180

agccgcctcc cttaattgct aaagcctcca caaggcacaa ttaagcaata tttcgggaaa    240

gtacaccagt cagtttgcgc ttttatgact gggttctaag gtactagatg tgaagtagtg    300

gtgacagaat cagggagata agagggagca gggtggggta atgatgtgcg ataacaatct    360

tgcttggcta atcaccccca tatcttgtag tgagtatata aataggagcc tcccttccta    420

ttgcaactcc ataaaatttt tttttgtagc cacttctgta acaagataaa taaaaccaac    480

taatcgagat atcacat                                                   497
```

<210> SEQ ID NO 4
<211> LENGTH: 500
<212> TYPE: DNA
<213> ORGANISM: Saccharomyces cerevisiae

<400> SEQUENCE: 4

```
ggaggtctgc ttcacgagcg cggtgtgcgc ctagtattgc cccgacggtc cgggtgccta     60

tccctagatt tcgtcgtgcc ccgacccaaa tagttaaacg tgtggtttat gggtgcacca    120

gggctttatc gtgttttata tcgatggcga tttgtgcctc cagtgtattt ttgtatatcc    180

aattaaggtt tcttacctaa ttttattttt atcatcttta gttaatgctg gtttgctctg    240

tttctgctgc tttctgtgcg gttctcctct tctcttgttt cttcgtgttg tcccccatcg    300

ccgatgggct tatatggcgt atatatatag agcgagtttt tacgtcgaag atcatctcag    360

tttgcttgat agcctttcta ctttattact ttcgttttta acctcattat actttagttt    420

tctttgatcg gttttttttct ctgtatactt aaaagttcaa atcaaagaaa catacaaaac    480

tacgtttata tcaattacat                                                500
```

<210> SEQ ID NO 5
<211> LENGTH: 35
<212> TYPE: DNA
<213> ORGANISM: Saccharomyces cerevisiae

<400> SEQUENCE: 5
atgcaagctt cgcggccgcc gtctgatttc cgttt 35

<210> SEQ ID NO 6
<211> LENGTH: 30
<212> TYPE: DNA
<213> ORGANISM: Saccharomyces cerevisiae

<400> SEQUENCE: 6
ccaggccgca tatgtcatat agtgtttaag 30

<210> SEQ ID NO 7
<211> LENGTH: 37
<212> TYPE: DNA
<213> ORGANISM: Saccharomyces cerevisiae

<400> SEQUENCE: 7
agctaagctt cgcggccgcc tttcgattag cacgcac 37

<210> SEQ ID NO 8
<211> LENGTH: 27
<212> TYPE: DNA
<213> ORGANISM: Saccharomyces cerevisiae

<400> SEQUENCE: 8
agataccttc atatgttatt attagtc 27

<210> SEQ ID NO 9
<211> LENGTH: 35
<212> TYPE: DNA
<213> ORGANISM: Saccharomyces cerevisiae

<400> SEQUENCE: 9
agctaagctt cgcggccgcg cagaaatgat gaagg 35

<210> SEQ ID NO 10
<211> LENGTH: 29
<212> TYPE: DNA
<213> ORGANISM: Saccharomyces cerevisiae

<400> SEQUENCE: 10
atccatccca tatgtgatat ctcgattag 29

<210> SEQ ID NO 11
<211> LENGTH: 35
<212> TYPE: DNA
<213> ORGANISM: Saccharomyces cerevisiae

<400> SEQUENCE: 11
agctaagctt cgcggccgcg gaggtctgct tcacg 35

<210> SEQ ID NO 12
<211> LENGTH: 29
<212> TYPE: DNA
<213> ORGANISM: Saccharomyces cerevisiae

<400> SEQUENCE: 12
tacgatcgca tatgtaattg atataaacg 29

<210> SEQ ID NO 13
<211> LENGTH: 20
<212> TYPE: DNA

-continued

```
<213> ORGANISM: Saccharomyces cerevisiae

<400> SEQUENCE: 13

cctcaattgg attagtctca                                                20


<210> SEQ ID NO 14
<211> LENGTH: 20
<212> TYPE: DNA
<213> ORGANISM: Saccharomyces cerevisiae

<400> SEQUENCE: 14

cacctcgata tgtgcatctg                                                20


<210> SEQ ID NO 15
<211> LENGTH: 63
<212> TYPE: DNA
<213> ORGANISM: Saccharomyces cerevisiae

<400> SEQUENCE: 15

ggccagtgaa ttgtaatacg actcactata gggaggcggt tttttttttt tttttttttt     60

ttt                                                                  63


<210> SEQ ID NO 16
<211> LENGTH: 20
<212> TYPE: DNA
<213> ORGANISM: Saccharomyces cerevisiae

<400> SEQUENCE: 16

gtcaagatgc taccgttcag                                                20


<210> SEQ ID NO 17
<211> LENGTH: 23
<212> TYPE: DNA
<213> ORGANISM: Saccharomyces cerevisiae
<220> FEATURE:
<221> NAME/KEY: unsure
<222> LOCATION: (17)..(23)
<223> OTHER INFORMATION: The symbol "n" at positions 17 to 23 represents
      any nucleotide.

<400> SEQUENCE: 17

aagcttcgcg gccgcgnnnn nnn                                            23


<210> SEQ ID NO 18
<211> LENGTH: 33
<212> TYPE: DNA
<213> ORGANISM: Saccharomyces cerevisiae
<220> FEATURE:
<221> NAME/KEY: unsure
<222> LOCATION: (27)..(33)
<223> OTHER INFORMATION: The symbol "n" at positions 27 to 33 represents
      any nucleotide.

<400> SEQUENCE: 18

aagcttagct aagcttcgcg gccgcgnnnn nnn                                 33


<210> SEQ ID NO 19
<211> LENGTH: 12844
<212> TYPE: DNA
<213> ORGANISM: Saccharomyces cerevisiae

<400> SEQUENCE: 19

aagcttcgcg gccgccgtct gatttccgtt ttgggaatcc tttgccgcgc gcccctctca     60

aaactccgca caagtcccag aaagcgggaa agaaataaaa cgccaccaaa aaaaaaaaaa    120
```

-continued

```
taaaagccaa tcctcgaagc gtgggtggta ggccctggat tatcccgtac aagtatttct    180
caggagtaaa aaaaccgttt gttttggaat tccccatttc gcggccacct acgccgctat    240
ctttgcaaca actatctgcg ataactcagc aaattttgca tattcgtgtt gcagtattgc    300
gataatggga gtcttacttc caacataacg gcagaaagaa atgtgagaaa attttgcatc    360
ctttgcctcc gttcaagtat ataaagtcgg catgcttgat aatctttctt tccatcctac    420
attgttctaa ttattcttat tctcctttat tctttcctaa cataccaaga aattaatctt    480
ctgtcattcg cttaaacact atatcacata tggaagacgc caaaaacata aagaaaggcc    540
cggcgccatt ctatccgctg gaagatggaa ccgctggaga gcaactgcat aaggctatga    600
agagatacgc cctggttcct ggaacaattg cttttacaga tgcacatatc gaggtggaca    660
tcacttacgc tgagtacttc gaaatgtccg ttcggttggc agaagctatg aaacgatatg    720
ggctgaatac aaatcacaga atcgtcgtat gcagtgaaaa ctctcttcaa ttctttatgc    780
cggtgttggg cgcgttattt atcggagttg cagttgcgcc cgcgaacgac atttataatg    840
aacgtgaatt gctcaacagt atgggcattt cgcagcctac cgtggtgttc gtttccaaaa    900
aggggttgca aaaaattttg aacgtgcaaa aaaagctccc aatcatccaa aaaattatta    960
tcatggattc taaaacggat taccagggat ttcagtcgat gtacacgttc gtcacatctc   1020
atctacctcc cggttttaat gaatacgatt ttgtgccaga gtccttcgat agggacaaga   1080
caattgcact gatcatgaac tcctctggat ctactggtct gcctaaaggt gtcgctctgc   1140
ctcatagaac tgcctgcgtg agattctcgc atgccagaga tcctattttt ggcaatcaaa   1200
tcattccgga tactgcgatt ttaagtgttg ttccattcca tcacggtttt ggaatgttta   1260
ctacactcgg atatttgata tgtggatttc gagtcgtctt aatgtataga tttgaagaag   1320
agctgtttct gaggagcctt caggattaca agattcaaag tgcgctgctg gtgccaaccc   1380
tattctcctt cttcgccaaa agcactctga ttgacaaata cgatttatct aatttacacg   1440
aaattgcttc tggtggcgct cccctctcta aggaagtcgg ggaagcggtt gccaagaggt   1500
tccatctgcc aggtatcagg caaggatatg ggctcactga gactacatca gctattctga   1560
ttacacccga gggggatgat aaaccgggcg cggtcggtaa agttgttcca ttttttgaag   1620
cgaaggttgt ggatctggat accgggaaaa cgctgggcgt taatcaaaga ggcgaactgt   1680
gtgtgagagg tcctatgatt atgtccggtt atgtaaacaa tccggaagcg accaacgcct   1740
tgattgacaa ggatggatgg ctacattctg gagacatagc ttactgggac gaagacgaac   1800
acttcttcat cgttgaccgc ctgaagtctc tgattaagta caaaggctat caggtggctc   1860
ccgctgaatt ggaatccatc ttgctccaac accccaacat cttcgacgca ggtgtcgcag   1920
gtcttcccga cgatgacgcc ggtgaacttc ccgccgccgt tgttgttttg gagcacggaa   1980
agacgatgac ggaaaaagag atcgtggatt acgtcgccag tcaagtaaca accgcgaaaa   2040
agttgcgcgg aggagttgtg tttgtggacg aagtaccgaa aggtcttacc ggaaaactcg   2100
acgcaagaaa aatcagagag atcctcataa aggccaagaa gggcggaaag atcgccgtgt   2160
aattggatcc agtttaaaca gtagctttgg acttcttcgc cagaggtttg gtcaagtctc   2220
caatcaaggt tgtcggcttg tctaccttgc cagaaattta cgaaaagatg gaaaagggtc   2280
aaatcgttgg tagatacgtt gttgacactt ctaaataagc gaatttctta tgatttatga   2340
tttttattat taaataagtt ataaaaaaaa taagtgtata caaattttaa agtgactctt   2400
aggttttaaa acgaaaattc ttgttcttga gtaactcttt cctgtaggtc aggttgcttt   2460
```

-continued

```
ctcaggtata gcatgaggtc gctcttattg accacacctc taccggcatg ccgagcaaat   2520
gcctgcaaat cgctccccat ttcacccaat tgtagatatg ctaactccag caatgagttg   2580
atgaatctcg gtgtgtattt tatgtcctca gaagacaaca cctgttgtaa tcgttcttcc   2640
acacggatcg cggccgcttg atcctctacg ccggacgcat cgtggccggc atcaccggcg   2700
ccacaggtgc ggttgctggc gcctatatcg ccgacatcac cgatggggaa gatcgggctc   2760
gccacttcgg gctcatgagc gcttgtttcg gcgtgggtat ggtggcaggc cccgtggccg   2820
ggggactgtt gggcgccatc tccttgcatg caccattcct tgcggcggcg gtgctcaacg   2880
gcctcaacct actactgggc tgcttcctaa tgcaggagtc gcataaggga gagcgtcgac   2940
cgatgccctt gagagccttc aacccagtca gctccttccg gtgggcgcgg ggcatgacta   3000
tcgtcgccgc acttatgact gtcttcttta tcatgcaact cgtaggacag gtgccggcag   3060
cgctctgggt cattttcggc gaggaccgct ttcgctggag cgcgacgatg atcggcctgt   3120
cgcttgcggt attcggaatc ttgcacgccc tcgctcaagc cttcgtcact ggtcccgcca   3180
ccaaacgttt cggcgagaag caggccatta tcgccggcat ggcggccgac gcgctgggct   3240
acgtcttgct ggcgttcgcg acgcgaggct ggatggcctt ccccattatg attcttctcg   3300
cttccggcgg catcgggatg cccgcgttgc aggccatgct gtccaggcag gtagatgacg   3360
accatcaggg acagcttcaa ggatcgctcg cggctcttac cagcctaact tcgatcactg   3420
gaccgctgat cgtcacggcg atttatgccg cctcggcgag cacatggaac gggttggcat   3480
ggattgtagg cgccgcccta taccttgtct gcctccccgc gttgcgtcgc ggtgcatgga   3540
gccgggccac ctcgacctga atggaagccg gcggcacctc gctaacggat tcaccactcc   3600
aagaattgga gccaatcaat tcttgcggag aactgtgaat gcgcaaacca acccttggca   3660
gaacatatcc atcgcgtccg ccatctccag cagccgcacg cggcgcatct cgggcagcgt   3720
tgggtcctgg ccacgggtgc gcatgatcgt gctcctgtcg ttgaggaccc ggctaggctg   3780
gcggggttgc cttactggtt agcagaatga atcaccgata cgcgagcgaa cgtgaagcga   3840
ctgctgctgc aaaacgtctg cgacctgagc aacaacatga atggtcttcg gtttccgtgt   3900
ttcgtaaagt ctggaaacgc ggaagtcagc gccctgcacc attatgttcc ggatctgcat   3960
cgcaggatgc tgctggctac cctgtggaac acctacatct gtattaacga agcgctggca   4020
ttgaccctga gtgatttttc tctggtcccg ccgcatccat accgccagtt gtttaccctc   4080
acaacgttcc agtaaccggg catgttcatc atcagtaacc cgtatcgtga gcatcctctc   4140
tcgtttcatc ggtatcatta cccccatgaa cagaaattcc cccttacacg gaggcatcaa   4200
gtgaccaaac aggaaaaaac cgcccttaac atggcccgct ttatcagaag ccagacatta   4260
acgcttctgg agaaactcaa cgagctggac gcggatgaac aggcagacat ctgtgaatcg   4320
cttcacgacc acgctgatga gctttaccgc agctgcctcg cgcgtttcgg tgatgacggt   4380
gaaaacctct gacacatgca gctcccggag acggtcacag cttgtctgta agcggatgcc   4440
gggagcagac aagcccgtca gggcgcgtca gcgggtgttg gcgggtgtcg gggcgcagcc   4500
atgacccagt cacgtagcga tagcggagtg tatactggct taactatgcg gcatcagagc   4560
agattgtact gagagtgcac gatatccggt gtgaaatacc gcacagatgc gtaaggagaa   4620
aataccgcat caggcgctct tccgcttcct cgctcactga ctcgctgcgc tcggtcgttc   4680
ggctgcggcg agcggtatca gctcactcaa aggcggtaat acggttatcc acagaatcag   4740
gggataacgc aggaaagaac atgtgagcaa aaggccagca aaaggccagg aaccgtaaaa   4800
aggccgcgtt gctggcgttt ttccataggc tccgcccccc tgacgagcat cacaaaaatc   4860
```

-continued

```
gacgctcaag tcagaggtgg cgaaacccga caggactata aagataccag gcgtttcccc   4920
ctggaagctc cctcgtgcgc tctcctgttc cgaccctgcc gcttaccgga tacctgtccg   4980
cctttctccc ttcgggaagc gtggcgcttt ctcaatgctc acgctgtagg tatctcagtt   5040
cggtgtaggt cgttcgctcc aagctgggct gtgtgcacga accccccgtt cagcccgacc   5100
gctgcgcctt atccggtaac tatcgtcttg agtccaaccc ggtaagacac gacttatcgc   5160
cactggcagc agccactggt aacaggatta gcagagcgag gtatgtaggc ggtgctacag   5220
agttcttgaa gtggtggcct aactacggct acactagaag gacagtattt ggtatctgcg   5280
ctctgctgaa gccagttacc ttcggaaaaa gagttggtag ctcttgatcc ggcaaacaaa   5340
ccaccgctgg tagcggtggt ttttttgttt gcaagcagca gattacgcgc agaaaaaaag   5400
gatctcaaga agatcctttg atcttttcta cggggtctga cgctcagtgg aacgaaaact   5460
cacgttaagg gattttggtc atgagattat caaaaaggat cttcacctag atccttttaa   5520
attaaaaatg aagttttaaa tcaatctaaa gtatatatga gtaaacttgg tctgacagtt   5580
accaatgctt aatcagtgag gcacctatct cagcgatctg tctatttcgt tcatccatag   5640
ttgcctgact ccccgtcgtg tagataacta cgatacggga gggcttacca tctggcccca   5700
gtgctgcaat gataccgcga gacccacgct caccggctcc agatttatca gcaataaacc   5760
agccagccgg aagggccgag cgcagaagtg gtcctgcaac tttatccgcc tccatccagt   5820
ctattaattg ttgccgggaa gctagagtaa gtagttcgcc agttaatagt ttgcgcaacg   5880
ttgttgccat tgctgcaggc atcgtggtgt cacgctcgtc gtttggtatg gcttcattca   5940
gctccggttc ccaacgatca aggcgagtta catgatcccc catgttgtgc aaaaaagcgg   6000
ttagctcctt cggtcctccg atcgttgtca gaagtaagtt ggccgcagtg ttatcactca   6060
tggttatggc agcactgcat aattctctta ctgtcatgcc atccgtaaga tgcttttctg   6120
tgactggtga gtactcaacc aagtcattct gagaatagtg tatgcggcga ccgagttgct   6180
cttgcccggc gtcaacacgg gataataccg cgccacatag cagaacttta aaagtgctca   6240
tcattggaaa acgttcttcg gggcgaaaac tctcaaggat cttaccgctg ttgagatcca   6300
gttcgatgta acccactcgt gcacccaact gatcttcagc atcttttact ttcaccagcg   6360
tttctgggtg agcaaaaaca ggaaggcaaa atgccgcaaa aaagggaata agggcgacac   6420
ggaaatgttg aatactcata ctcttccttt ttcaatatta ttgaagcatt tatcagggtt   6480
attgtctcat gagcggatac atatttgaat gtatttagaa aaataaacaa ataggggttc   6540
cgcgcacatt tccccgaaaa gtgccacctg acgtctaaga aaccattatt atcatgacat   6600
taacctataa aaataggcgt atcacgaggc cctttcgtct tcaagaattc cacggactat   6660
agactatact agtatactcc gtctactgta cgatacactt ccgctcaggt ccttgtcctt   6720
taacgaggcc ttaccactct tttgttactc tattgatcca gctcagcaaa ggcagtgtga   6780
tctaagattc tatcttcgcg atgtagtaaa actagctaga ccgagaaaga gactagaaat   6840
gcaaaaggca cttctacaat ggctgccatc attattatcc gatgtgacgc tgcagaagca   6900
gaaatacacg cggtcagtga agctattccg ctattgaata acctcagtca ccttgtgcaa   6960
gaacttaaca agaaaccaat tattaaaggc ttacttactg atagtagatc aacgatcagt   7020
ataattaagt ctacaaatga agagaaattt agaaacagat tttttggcac aaaggcaatg   7080
agacttagag atgaagtatc aggtaataat ttatacgtat actacatcga gaccaagaag   7140
aacattgctg atgtgatgac aaaacctctt ccgataaaaa catttaaact attaactaac   7200
```

-continued

```
aaatggattc attagatcta ttacattatg ggtggtatgt tggaataaaa atcaactatc   7260
atctactaac tagtatttac gttactagta tattatcata tacggtgtta gaagatgacg   7320
caaatgatga gaaatagtca tctaaattag tggaagctga aacgcaagga ttgataatgt   7380
aataggatca atgaatatta acatataaaa tgatgataat aatatttata gaattgtgta   7440
gaattgcaga ttccctttta tggattccta aatcctcgag gagaacttct agtatatcta   7500
catacctaat attattgcct tattaaaaat ggaatcccaa caattacatc aaaatccaca   7560
ttctcttcaa aatcaattgt cctgtacttc cttgttcatg tgtgttcaaa aacgttatat   7620
ttataggata attatactct atttctcaac aagtaattgg ttgtttggcc gagcggtcta   7680
aggcgcctga ttcaagaaat atcttgaccg cagttaactg tgggaatact caggtatcgt   7740
aagatgcaag agttcgaatc tcttagcaac cattattttt ttcctcaaca taacgagaac   7800
acacaggggc gctatcgcac agaatcaaat tcgatgactg gaaatttttt gttaatttca   7860
gaggtcgcct gacgcatata ccttttttcaa ctgaaaaatt gggagaaaaa ggaaaggtga   7920
gagccgcgga accggctttt catatagaat agagaagcgt tcatgactaa atgcttgcat   7980
cacaatactt gaagttgaca atattattta aggacctatt gttttttcca ataggtggtt   8040
agcaatcgtc ttactttcta acttttctta ccttttacat ttcagcaata tatatatata   8100
tatttcaagg atataccatt ctaatgtctg cccctaagaa gatcgtcgtt ttgccaggtg   8160
accacgttgg tcaagaaatc acagccgaag ccattaaggt tcttaaagct atttctgatg   8220
ttcgttccaa tgtcaagttc gatttcgaaa atcatttaat tggtggtgct gctatcgatg   8280
ctacaggtgt cccacttcca gatgaggcgc tggaagcctc caagaaggtt gatgccgttt   8340
tgttaggtgc tgtgggtggt cctaaatggg gtaccggtag tgttagacct gaacaaggtt   8400
tactaaaaat ccgtaaagaa cttcaattgt acgccaactt aagaccatgt aactttgcat   8460
ccgactctct tttagactta tctccaatca agccacaatt tgctaaaggt actgacttcg   8520
ttgttgtcag agaattagtg ggaggtattt actttggtaa gagaaaggaa gacgatggtg   8580
atggtgtcgc ttgggatagt gaacaataca ccgttccaga agtgcaaaga atcacaagaa   8640
tggccgcttt catggcccta caacatgagc caccattgcc tatttggtcc ttggataaag   8700
ctaatgtttt ggcctcttca agattatgga gaaaaactgt ggaggaaacc atcaagaacg   8760
aattccctac attgaaggtt caacatcaat tgattgattc tgccgccatg atcctagtta   8820
agaacccaac ccacctaaat ggtattataa tcaccagcaa catgtttggt gatatcatct   8880
ccgatgaagc ctccgttatc ccaggttcct tgggtttgtt gccatctgcg tccttggcct   8940
ctttgccaga caagaacacc gcatttggtt tgtacgaacc atgccacggt tctgctccag   9000
atttgccaaa gaataaggtc aaccctatcg ccactatctt gtctgctgca atgatgttga   9060
aattgtcatt gaacttgcct gaagaaggta aggccattga agatgcagtt aaaaaggttt   9120
tggatgcagg tatcagaact ggtgatttag gtggttccaa cagtaccacg gaagtcggtg   9180
atgctgtcgc cgaagaagtt aagaaaatcc ttgcttaaaa agattctctt tttttatgat   9240
atttgtacat aaactttata aatgaaattc ataatagaaa cgacacgaaa ttacaaaatg   9300
gaatatgttc atagggtaga cgaaactata tacgcaatct acatacattt atcaagaagg   9360
agaaaaagga ggatgtaaag gaatacaggt aagcaaattg atactaatgg ctcaacgtga   9420
taaggaaaaa gaattgcact ttaacattaa tattgacaag gaggagggca ccacacaaaa   9480
agttaggtgt aacagaaaat catgaaacta tgattcctaa tttatatatt ggaggatttt   9540
ctctaaaaaa aaaaaaatac aacaaataaa aaacactcaa tgacctgacc atttgatgga   9600
```

-continued

```
gtttaagtca ataccttctt gaaccatttc ccataatggt gaaagttccc tcaagaattt   9660
tactctgtca gaaacggcct taacgacgta gtcgacctcc tcttcagtac taaatctacc   9720
aataccaaat ctgatggaag aatgggctaa tgcatcatcc ttacccagcg catgtaaaac   9780
ataagaaggt tctagggaag cagatgtaca ggctgaaccc gaggataatg cgatatccct   9840
tagtgccatc aataaagatt ctccttccac gtaggcgaaa gaaacgttaa cacaccctgg   9900
ataacgatga tctggagatc cgttcaacgt ggtatgttca gcggataata gacctttgac   9960
taatttatcg gatagtcttt tgatgtgagc ttggtcgttg tcaaattctt tcttcatcaa  10020
tctcgcagct tcaccaaatc ccgctaccaa tggggggcc aaagtaccag atctcaatcc  10080
tctctcttgg ccaccaccgg atagtaaagg ttctaatcta actcttggtc tccttcttac  10140
atagatggca cctattccct ttggaccgta aatcttgtga gaagaaattg atagtaaatc  10200
aatgttcatt tcattgacat caatgtgaat cttaccatag gcttgtgcgg cgtcagtatg  10260
aaagtagatc ttattctttc tacaaattgc accaatttct ttaataggtt gaatgacacc  10320
gatttcatta ttgacagcca tcacagagac gagacaggta tctggtctaa tggcatcttc  10380
caattccttc aaatcgataa gaccttgatc gtccacattt aggaaagtga cttcaaatcc  10440
ctccttcatc atggcccgtg cggcttccaa gacacacttg tgttccgttc tagtggtgat  10500
gatgtgtttc ttagtcttct tataaaatct tgggacaccc ttaagaacca tattattaga  10560
ttcggtcgct cccgaagtga atattatttc cttggggtcg gcattgatca tctttgctac  10620
gtaagctcta gcattttcca cagcagtatt tgtttcccaa ccgtaagagt gagtgttgga  10680
atgaggatta ccataaagtc ccgtataaaa cttcaacatc gtatccaaaa ccctagggtc  10740
tgttggtgta gtggcttgca tgtcaagata tatgggacga gtaccaaaac ctgtgttttc  10800
ttgataagca tggctcattg cagtgctacc agaagctact acagcatctg ggtggtacc  10860
ggatgcactc gcacgggcac tagcctgtgc ctttgcagca gcctgaatat cggtatgcgt  10920
ttccagagag aagttgtcgt ctaacttcac gcctgctgca gtctcaatga tattcgaata  10980
cgctttgagg agatacagcc taatatccga caaactgttt tacagattta cgatcgtact  11040
tgttacccat cattgaattt tgaacatccg aacctgggag ttttccctga aacagatagt  11100
atatttgaac ctgtataata atatatagtc tagcgcttta cggaagacaa tgtatgtatt  11160
tcggttcctg gagaaactat tgcatctatt gcataggtaa tcttgcacgt cgcatccccg  11220
gttcattttc tgcgtttcca tcttgcactt caatagcata tctttgttaa cgaagcatct  11280
gtgcttcatt ttgtagaaca aaaatgcaac gcgagagcgc taatttttca aacaaagaat  11340
ctgagctgca tttttacaga acagaaatgc aacgcgaaag cgctatttta ccaacgaaga  11400
atctgtgctt catttttgta aaacaaaaat gcaacgcgag agcgctaatt tttcaaacaa  11460
agaatctgag ctgcattttt acagaacaga aatgcaacgc gagagcgcta ttttaccaac  11520
aaagaatcta tacttctttt ttgttctaca aaaatgcatc ccgagagcgc tatttttcta  11580
acaaagcatc ttagattact ttttttctcc tttgtgcgct ctataatgca gtctcttgat  11640
aactttttgc actgtaggtc cgttaaggtt agaagaaggc tactttggtg tctattttct  11700
cttccataaa aaaagcctga ctccacttcc cgcgtttact gattactagc gaagctgcgg  11760
gtgcattttt tcaagataaa ggcatccccg attatattct ataccgatgt ggattgcgca  11820
tactttgtga acagaaagtg atagcgttga tgattcttca ttggtcagaa aattatgaac  11880
ggtttcttct attttgtctc tatatactac gtataggaaa tgtttacatt ttcgtattgt  11940
```

-continued

```
tttcgattca ctctatgaat agttcttact acaatttttt tgtctaaaga gtaatactag  12000

agataaacat aaaaaatgta gaggtcgagt ttagatgcaa gttcaaggag cgaaaggtgg  12060

atgggtaggt tatataggga tatagcacag agatatatag caaagagata cttttgagca  12120

atgtttgtgg aagcggtatt cgcaatattt tagtagctcg ttacagtccg gtgcgttttt  12180

ggtttttga aagtgcgtct tcagagcgct tttggttttc aaaagcgctc tgaagttcct  12240

atactttcta gagaatagga acttcggaat aggaacttca aagcgtttcc gaaaacgagc  12300

gcttccgaaa atgcaacgcg agctgcgcac atacagctca ctgttcacgt cgcacctata  12360

tctgcgtgtt gcctgtatat atatatacat gagaagaacg gcatagtgcg tgtttatgct  12420

taaatgcgta cttatatgcg tctatttatg taggatgaaa ggtagtctag tacctcctgt  12480

gatattatcc cattccatgc ggggtatcgt atgcttcctt cagcactacc ctttagctgt  12540

tctatatgct gccactcctc aattggatta gtctcatcct tcaatgctat catttccttt  12600

gatattcgat cctaggcata gtaccgagaa actagtgcga agtagtgatc aggtattgct  12660

gttatctgat gagtatacgt tgtcctggcc acggcagaag cacgcttatc gctccaattt  12720

cccacaacat tagtcaactc cgttaggccc ttcattgaaa gaaatgaggt catcaaatgt  12780

cttccaatgt gagattttgg gccatttttt atagcaaaga ttgaataagg cgcatttttc  12840

ttca                                                               12844
```

<210> SEQ ID NO 20
<211> LENGTH: 13073
<212> TYPE: DNA
<213> ORGANISM: Saccharomyces cerevisiae

<400> SEQUENCE: 20

```
aagcttcgcg gccgcctttc gattagcacg cacacacatc acatagactg cgtcataaaa     60

atacactacg gaaaaaccat aaagagcaaa gcgataccta cttggaagga aaaggagcac    120

gcttgtaagg gggatggggg ctaagaagtc attcactttc ttttcccttc gcggtccgga    180

cccgggaccc ctcctctccc cgcacgattt cttcctttca tatcttcctt ttattcctat    240

cccgttgaag caaccgcact atgactaaat ggtgctggac atctccatgg ctgtgacttg    300

tgtgtatctc acagtggtaa cggcaccgtg gctcggaaac ggttccttcg tgacaattct    360

agaacagggg ctacagtctc gataatagaa taataagcgc atttttgcta gcgccgccgc    420

ggcgcccgtt tcccaatagg gaggcgcagt ttatcggcgg agctctactt cttcctattt    480

gggtaagccc ctttctgttt tcggccagtg gttgctgcag gctgcgccgg agaacatagt    540

gataagggat gtaactttcg atgagagaat tagcaagcgg aaaaaaacta tggctagctg    600

ggagttgttt ttcaatcata taaaagggag aaattgttgc tcactatgtg acagtttctg    660

ggacgtctta acttttattg cagaggacta tcaaatcata cagatattgt caaaaaaaaa    720

aaagactaat aataacatat ggaagacgcc aaaaacataa agaaaggccc ggcgccattc    780

tatccgctgg aagatggaac cgctggagag caactgcata aggctatgaa gagatacgcc    840

ctggttcctg gaacaattgc ttttacagat gcacatatcg aggtggacat cacttacgct    900

gagtacttcg aaatgtccgt tcggttggca gaagctatga aacgatatgg gctgaataca    960

aatcacagaa tcgtcgtatg cagtgaaaac tctcttcaat tctttatgcc ggtgttgggc   1020

gcgttattta tcggagttgc agttgcgccc gcgaacgaca tttataatga acgtgaattg   1080

ctcaacagta tgggcatttc gcagcctacc gtggtgttcg tttccaaaaa ggggttgcaa   1140

aaaattttga acgtgcaaaa aaagctccca atcatccaaa aaattattat catggattct   1200
```

-continued

```
aaaacggatt accagggatt tcagtcgatg tacacgttcg tcacatctca tctacctccc   1260
ggttttaatg aatacgattt tgtgccagag tccttcgata gggacaagac aattgcactg   1320
atcatgaact cctctggatc tactggtctg cctaaaggtg tcgctctgcc tcatagaact   1380
gcctgcgtga gattctcgca tgccagagat cctatttttg gcaatcaaat cattccggat   1440
actgcgattt taagtgttgt tccattccat cacggttttg gaatgtttac tacactcgga   1500
tatttgatat gtggatttcg agtcgtctta atgtatagat ttgaagaaga gctgtttctg   1560
aggagccttc aggattacaa gattcaaagt gcgctgctgg tgccaaccct attctccttc   1620
ttcgccaaaa gcactctgat tgacaaatac gatttatcta atttacacga aattgcttct   1680
ggtggcgctc ccctctctaa ggaagtcggg gaagcggttg ccaagaggtt ccatctgcca   1740
ggtatcaggc aaggatatgg gctcactgag actacatcag ctattctgat tacacccgag   1800
ggggatgata aaccgggcgc ggtcggtaaa gttgttccat tttttgaagc gaaggttgtg   1860
gatctggata ccgggaaaac gctgggcgtt aatcaaagag gcgaactgtg tgtgagaggt   1920
cctatgatta tgtccggtta tgtaaacaat ccggaagcga ccaacgcctt gattgacaag   1980
gatggatggc tacattctgg agacatagct tactgggacg aagacgaaca cttcttcatc   2040
gttgaccgcc tgaagtctct gattaagtac aaaggctatc aggtggctcc cgctgaattg   2100
gaatccatct tgctccaaca ccccaacatc ttcgacgcag gtgtcgcagg tcttcccgac   2160
gatgacgccg gtgaacttcc cgccgccgtt gttgttttgg agcacggaaa gacgatgacg   2220
gaaaaagaga tcgtggatta cgtcgccagt caagtaacaa ccgcgaaaaa gttgcgcgga   2280
ggagttgtgt ttgtggacga agtaccgaaa ggtcttaccg gaaaactcga cgcaagaaaa   2340
atcagagaga tcctcataaa ggccaagaag ggcggaaaga tcgccgtgta attggatcca   2400
gtttaaacag tagctttgga cttcttcgcc agaggtttgg tcaagtctcc aatcaaggtt   2460
gtcggcttgt ctaccttgcc agaaatttac gaaaagatgg aaaagggtca aatcgttggt   2520
agatacgttg ttgacacttc taaataagcg aatttcttat gatttatgat ttttattatt   2580
aaataagtta taaaaaaaat aagtgtatac aaattttaaa gtgactctta ggttttaaaa   2640
cgaaaattct tgttcttgag taactctttc ctgtaggtca ggttgctttc tcaggtatag   2700
catgaggtcg ctcttattga ccacacctct accggcatgc cgagcaaatg cctgcaaatc   2760
gctccccatt tcacccaatt gtagatatgc taactccagc aatgagttga tgaatctcgg   2820
tgtgtatttt atgtcctcag aagacaacac ctgttgtaat cgttcttcca cacggatcgc   2880
ggccgcttga tcctctacgc cggacgcatc gtggccggca tcaccggcgc cacaggtgcg   2940
gttgctggcg cctatatcgc cgacatcacc gatggggaag atcgggctcg ccacttcggg   3000
ctcatgagcg cttgtttcgg cgtgggtatg gtggcaggcc ccgtggccgg gggactgttg   3060
ggcgccatct ccttgcatgc accattcctt gcggcggcgg tgctcaacgg cctcaaccta   3120
ctactgggct gcttcctaat gcaggagtcg cataagggag agcgtcgacc gatgcccttg   3180
agagccttca acccagtcag ctccttccgg tgggcgcggg gcatgactat cgtcgccgca   3240
cttatgactg tcttctttat catgcaactc gtaggacagg tgccggcagc gctctgggtc   3300
attttcggcg aggaccgctt tcgctggagc gcgacgatga tcggcctgtc gcttgcggta   3360
ttcggaatct tgcacgccct cgctcaagcc ttcgtcactg gtcccgccac caaacgtttc   3420
ggcgagaagc aggccattat cgccggcatg gcggccgacg cgctgggcta cgtcttgctg   3480
gcgttcgcga cgcgaggctg gatggccttc cccattatga ttcttctcgc ttccggcggc   3540
```

-continued

```
atcgggatgc ccgcgttgca ggccatgctg tccaggcagg tagatgacga ccatcaggga   3600
cagcttcaag gatcgctcgc ggctcttacc agcctaactt cgatcactgg accgctgatc   3660
gtcacggcga tttatgccgc ctcggcgagc acatggaacg ggttggcatg gattgtaggc   3720
gccgccctat accttgtctg cctccccgcg ttgcgtcgcg gtgcatggag ccgggccacc   3780
tcgacctgaa tggaagccgg cggcacctcg ctaacggatt caccactcca agaattggag   3840
ccaatcaatt cttgcggaga actgtgaatg cgcaaaccaa cccttggcag aacatatcca   3900
tcgcgtccgc catctccagc agccgcacgc ggcgcatctc gggcagcgtt gggtcctggc   3960
cacgggtgcg catgatcgtg ctcctgtcgt tgaggacccg gctaggctgg cggggttgcc   4020
ttactggtta gcagaatgaa tcaccgatac gcgagcgaac gtgaagcgac tgctgctgca   4080
aaacgtctgc gacctgagca acaacatgaa tggtcttcgg tttccgtgtt tcgtaaagtc   4140
tggaaacgcg gaagtcagcg ccctgcacca ttatgttccg gatctgcatc gcaggatgct   4200
gctggctacc ctgtggaaca cctacatctg tattaacgaa gcgctggcat tgaccctgag   4260
tgatttttct ctggtcccgc cgcatccata ccgccagttg tttaccctca caacgttcca   4320
gtaaccgggc atgttcatca tcagtaaccc gtatcgtgag catcctctct cgtttcatcg   4380
gtatcattac ccccatgaac agaaattccc ccttacacgg aggcatcaag tgaccaaaca   4440
ggaaaaaacc gcccttaaca tggcccgctt tatcagaagc cagacattaa cgcttctgga   4500
gaaactcaac gagctggacg cggatgaaca ggcagacatc tgtgaatcgc ttcacgacca   4560
cgctgatgag ctttaccgca gctgcctcgc gcgtttcggt gatgacggtg aaaacctctg   4620
acacatgcag ctcccggaga cggtcacagc ttgtctgtaa gcggatgccg ggagcagaca   4680
agcccgtcag ggcgcgtcag cgggtgttgg cgggtgtcgg ggcgcagcca tgacccagtc   4740
acgtagcgat agcggagtgt atactggctt aactatgcgg catcagagca gattgtactg   4800
agagtgcacg atatccggtg tgaaataccg cacagatgcg taaggagaaa ataccgcatc   4860
aggcgctctt ccgcttcctc gctcactgac tcgctgcgct cggtcgttcg gctgcggcga   4920
gcggtatcag ctcactcaaa ggcggtaata cggttatcca cagaatcagg ggataacgca   4980
ggaaagaaca tgtgagcaaa aggccagcaa aaggccagga accgtaaaaa ggccgcgttg   5040
ctggcgtttt tccataggct ccgcccccct gacgagcatc acaaaaatcg acgctcaagt   5100
cagaggtggc gaaacccgac aggactataa agataccagg cgtttccccc tggaagctcc   5160
ctcgtgcgct ctcctgttcc gaccctgccg cttaccggat acctgtccgc ctttctccct   5220
tcgggaagcg tggcgctttc tcaatgctca cgctgtaggt atctcagttc ggtgtaggtc   5280
gttcgctcca agctgggctg tgtgcacgaa ccccccgttc agcccgaccg ctgcgcctta   5340
tccggtaact atcgtcttga gtccaacccg gtaagacacg acttatcgcc actggcagca   5400
gccactggta acaggattag cagagcgagg tatgtaggcg gtgctacaga gttcttgaag   5460
tggtggccta actacggcta cactagaagg acagtatttg gtatctgcgc tctgctgaag   5520
ccagttacct tcggaaaaag agttggtagc tcttgatccg gcaaacaaac caccgctggt   5580
agcggtggtt tttttgtttg caagcagcag attacgcgca gaaaaaaagg atctcaagaa   5640
gatcctttga tcttttctac ggggtctgac gctcagtgga acgaaaactc acgttaaggg   5700
attttggtca tgagattatc aaaaaggatc ttcacctaga tccttttaaa ttaaaaatga   5760
agttttaaat caatctaaag tatatatgag taaacttggt ctgacagtta ccaatgctta   5820
atcagtgagg cacctatctc agcgatctgt ctatttcgtt catccatagt tgcctgactc   5880
cccgtcgtgt agataactac gatacgggag ggcttaccat ctggccccag tgctgcaatg   5940
```

-continued

```
ataccgcgag acccacgctc accggctcca gatttatcag caataaacca gccagccgga   6000
agggccgagc gcagaagtgg tcctgcaact ttatccgcct ccatccagtc tattaattgt   6060
tgccgggaag ctagagtaag tagttcgcca gttaatagtt tgcgcaacgt tgttgccatt   6120
gctgcaggca tcgtggtgtc acgctcgtcg tttggtatgg cttcattcag ctccggttcc   6180
caacgatcaa ggcgagttac atgatccccc atgttgtgca aaaaagcggt tagctccttc   6240
ggtcctccga tcgttgtcag aagtaagttg gccgcagtgt tatcactcat ggttatggca   6300
gcactgcata attctcttac tgtcatgcca tccgtaagat gcttttctgt gactggtgag   6360
tactcaacca agtcattctg agaatagtgt atgcggcgac cgagttgctc ttgcccggcg   6420
tcaacacggg ataataccgc gccacatagc agaactttaa aagtgctcat cattggaaaa   6480
cgttcttcgg ggcgaaaact ctcaaggatc ttaccgctgt tgagatccag ttcgatgtaa   6540
cccactcgtg cacccaactg atcttcagca tcttttactt tcaccagcgt ttctgggtga   6600
gcaaaaacag gaaggcaaaa tgccgcaaaa aagggaataa gggcgacacg gaaatgttga   6660
atactcatac tcttcctttt tcaatattat tgaagcattt atcagggtta ttgtctcatg   6720
agcggataca tatttgaatg tatttagaaa aataaacaaa taggggttcc gcgcacattt   6780
ccccgaaaag tgccacctga cgtctaagaa accattatta tcatgacatt aacctataaa   6840
aataggcgta tcacgaggcc ctttcgtctt caagaattcc acggactata gactatacta   6900
gtatactccg tctactgtac gatacacttc cgctcaggtc cttgtccttt aacgaggcct   6960
taccactctt ttgttactct attgatccag ctcagcaaag gcagtgtgat ctaagattct   7020
atcttcgcga tgtagtaaaa ctagctagac cgagaaagag actagaaatg caaaaggcac   7080
ttctacaatg gctgccatca ttattatccg atgtgacgct gcagaagcag aaatacacgc   7140
ggtcagtgaa gctattccgc tattgaataa cctcagtcac cttgtgcaag aacttaacaa   7200
gaaaccaatt attaaaggct tacttactga tagtagatca acgatcagta taattaagtc   7260
tacaaatgaa gagaaattta gaaacagatt ttttggcaca aaggcaatga gacttagaga   7320
tgaagtatca ggtaataatt tatacgtata ctacatcgag accaagaaga acattgctga   7380
tgtgatgaca aaacctcttc cgataaaaac atttaaacta ttaactaaca aatggattca   7440
ttagatctat tacattatgg gtggtatgtt ggaataaaaa tcaactatca tctactaact   7500
agtatttacg ttactagtat attatcatat acggtgttag aagatgacgc aaatgatgag   7560
aaatagtcat ctaaattagt ggaagctgaa acgcaaggat tgataatgta ataggatcaa   7620
tgaatattaa catataaaat gatgataata atatttatag aattgtgtag aattgcagat   7680
tcccttttat ggattcctaa atcctcgagg agaacttcta gtatatctac atacctaata   7740
ttattgcctt attaaaaatg gaatcccaac aattacatca aaatccacat tctcttcaaa   7800
atcaattgtc ctgtacttcc ttgttcatgt gtgttcaaaa acgttatatt tataggataa   7860
ttatactcta tttctcaaca agtaattggt tgtttggccg agcggtctaa ggcgcctgat   7920
tcaagaaata tcttgaccgc agttaactgt gggaatactc aggtatcgta agatgcaaga   7980
gttcgaatct cttagcaacc attatttttt tcctcaacat aacgagaaca cacaggggcg   8040
ctatcgcaca gaatcaaatt cgatgactgg aaattttttg ttaatttcag aggtcgcctg   8100
acgcatatac ctttttcaac tgaaaaattg ggagaaaaag gaaaggtgag agccgcggaa   8160
ccggcttttc atatagaata gagaagcgtt catgactaaa tgcttgcatc acaatacttg   8220
aagttgacaa tattatttaa ggacctattg ttttttccaa taggtggtta gcaatcgtct   8280
```

-continued

```
tactttctaa cttttcttac cttttacatt tcagcaatat atatatatat atttcaagga   8340
tataccattc taatgtctgc ccctaagaag atcgtcgttt tgccaggtga ccacgttggt   8400
caagaaatca cagccgaagc cattaaggtt cttaaagcta tttctgatgt tcgttccaat   8460
gtcaagttcg atttcgaaaa tcatttaatt ggtggtgctg ctatcgatgc tacaggtgtc   8520
ccacttccag atgaggcgct ggaagcctcc aagaaggttg atgccgtttt gttaggtgct   8580
gtgggtggtc ctaaatgggg taccggtagt gttagacctg aacaaggttt actaaaaatc   8640
cgtaaagaac ttcaattgta cgccaactta agaccatgta actttgcatc cgactctctt   8700
ttagacttat ctccaatcaa gccacaattt gctaaaggta ctgacttcgt tgttgtcaga   8760
gaattagtgg gaggtattta ctttggtaag agaaaggaag acgatggtga tggtgtcgct   8820
tgggatagtg aacaatacac cgttccagaa gtgcaaagaa tcacaagaat ggccgctttc   8880
atggccctac aacatgagcc accattgcct atttggtcct tggataaagc taatgttttg   8940
gcctcttcaa gattatggag aaaaactgtg gaggaaacca tcaagaacga attccctaca   9000
ttgaaggttc aacatcaatt gattgattct gccgccatga tcctagttaa gaacccaacc   9060
cacctaaatg gtattataat caccagcaac atgtttggtg atatcatctc cgatgaagcc   9120
tccgttatcc caggttcctt gggtttgttg ccatctgcgt ccttggcctc tttgccagac   9180
aagaacaccg catttggttt gtacgaacca tgccacggtt ctgctccaga tttgccaaag   9240
aataaggtca accctatcgc cactatcttg tctgctgcaa tgatgttgaa attgtcattg   9300
aacttgcctg aagaaggtaa ggccattgaa gatgcagtta aaaaggtttt ggatgcaggt   9360
atcagaactg gtgatttagg tggttccaac agtaccacgg aagtcggtga tgctgtcgcc   9420
gaagaagtta agaaaatcct tgcttaaaaa gattctcttt ttttatgata tttgtacata   9480
aactttataa atgaaattca taatagaaac gacacgaaat tacaaaatgg aatatgttca   9540
tagggtagac gaaactatat acgcaatcta catacattta tcaagaagga gaaaaaggag   9600
gatgtaaagg aatacaggta agcaaattga tactaatggc tcaacgtgat aaggaaaaag   9660
aattgcactt taacattaat attgacaagg aggagggcac cacacaaaaa gttaggtgta   9720
acagaaaatc atgaaactat gattcctaat ttatatattg gaggattttc tctaaaaaaa   9780
aaaaaataca acaaataaaa aacactcaat gacctgacca tttgatggag tttaagtcaa   9840
taccttcttg aaccatttcc cataatggtg aaagttccct caagaatttt actctgtcag   9900
aaacggcctt aacgacgtag tcgacctcct cttcagtact aaatctacca ataccaaatc   9960
tgatggaaga atgggctaat gcatcatcct tacccagcgc atgtaaaaca taagaaggtt  10020
ctagggaagc agatgtacag gctgaacccg aggataatgc gatatccctt agtgccatca  10080
ataaagattc tccttccacg taggcgaaag aaacgttaac acaccctgga taacgatgat  10140
ctggagatcc gttcaacgtg gtatgttcag cggataatag acctttgact aatttatcgg  10200
atagtctttt gatgtgagct tggtcgttgt caaattcttt cttcatcaat ctcgcagctt  10260
caccaaatcc cgctaccaat gggggggcca aagtaccaga tctcaatcct ctctcttggc  10320
caccaccgga tagtaaaggt tctaatctaa ctcttggtct ccttcttaca tagatggcac  10380
ctattccctt tggaccgtaa atcttgtgag aagaaattga tagtaaatca atgttcattt  10440
cattgacatc aatgtgaatc ttaccatagg cttgtgcggc gtcagtatga aagtagatct  10500
tattctttct acaaattgca ccaatttctt taataggttg aatgacaccg atttcattat  10560
tgacagccat cacagagacg agacaggtat ctggtctaat ggcatcttcc aattccttca  10620
aatcgataag accttgatcg tccacattta ggaaagtgac ttcaaatccc tccttcatca  10680
```

-continued

```
tggcccgtgc ggcttccaag acacacttgt gttccgttct agtggtgatg atgtgtttct  10740
tagtcttctt ataaaatctt gggacaccct taagaaccat attattagat tcggtcgctc  10800
ccgaagtgaa tattatttcc ttggggtcgg cattgatcat ctttgctacg taagctctag  10860
cattttccac agcagtattt gtttcccaac cgtaagagtg agtgttggaa tgaggattac  10920
cataaagtcc cgtataaaac ttcaacatcg tatccaaaac cctagggtct gttggtgtag  10980
tggcttgcat gtcaagatat atgggacgag taccaaaacc tgtgttttct tgataagcat  11040
ggctcattgc agtgctacca gaagctacta cagcatctgg ggtggtaccg gatgcactcg  11100
cacgggcact agcctgtgcc tttgcagcag cctgaatatc ggtatgcgtt tccagagaga  11160
agttgtcgtc taacttcacg cctgctgcag tctcaatgat attcgaatac gctttgagga  11220
gatacagcct aatatccgac aaactgtttt acagatttac gatcgtactt gttacccatc  11280
attgaatttt gaacatccga acctgggagt tttccctgaa acagatagta tatttgaacc  11340
tgtataataa tatatagtct agcgctttac ggaagacaat gtatgtattt cggttcctgg  11400
agaaactatt gcatctattg cataggtaat cttgcacgtc gcatccccgg ttcattttct  11460
gcgtttccat cttgcacttc aatagcatat ctttgttaac gaagcatctg tgcttcattt  11520
tgtagaacaa aaatgcaacg cgagagcgct aatttttcaa acaaagaatc tgagctgcat  11580
ttttacagaa cagaaatgca acgcgaaagc gctattttac caacgaagaa tctgtgcttc  11640
atttttgtaa aacaaaaatg caacgcgaga gcgctaattt ttcaaacaaa gaatctgagc  11700
tgcattttta cagaacagaa atgcaacgcg agagcgctat tttaccaaca aagaatctat  11760
acttcttttt tgttctacaa aaatgcatcc cgagagcgct atttttctaa caaagcatct  11820
tagattactt tttttctcct ttgtgcgctc tataatgcag tctcttgata actttttgca  11880
ctgtaggtcc gttaaggtta gaagaaggct actttggtgt ctattttctc ttccataaaa  11940
aaagcctgac tccacttccc gcgtttactg attactagcg aagctgcggg tgcatttttt  12000
caagataaag gcatccccga ttatattcta taccgatgtg gattgcgcat actttgtgaa  12060
cagaaagtga tagcgttgat gattcttcat tggtcagaaa attatgaacg gtttcttcta  12120
ttttgtctct atatactacg tataggaaat gtttacattt tcgtattgtt ttcgattcac  12180
tctatgaata gttcttacta caattttttt gtctaaagag taatactaga gataaacata  12240
aaaaatgtag aggtcgagtt tagatgcaag ttcaaggagc gaaaggtgga tgggtaggtt  12300
atatagggat atagcacaga gatatatagc aaagagatac ttttgagcaa tgtttgtgga  12360
agcggtattc gcaatatttt agtagctcgt tacagtccgg tgcgtttttg gtttttttgaa  12420
agtgcgtctt cagagcgctt ttggttttca aaagcgctct gaagttccta tactttctag  12480
agaataggaa cttcggaata ggaacttcaa agcgtttccg aaaacgagcg cttccgaaaa  12540
tgcaacgcga gctgcgcaca tacagctcac tgttcacgtc gcacctatat ctgcgtgttg  12600
cctgtatata tatatacatg agaagaacgg catagtgcgt gtttatgctt aaatgcgtac  12660
ttatatgcgt ctatttatgt aggatgaaag gtagtctagt acctcctgtg atattatccc  12720
attccatgcg gggtatcgta tgcttccttc agcactaccc tttagctgtt ctatatgctg  12780
ccactcctca attggattag tctcatcctt caatgctatc atttcctttg atattcgatc  12840
ctaggcatag taccgagaaa ctagtgcgaa gtagtgatca ggtattgctg ttatctgatg  12900
agtatacgtt gtcctggcca cggcagaagc acgcttatcg ctccaatttc ccacaacatt  12960
agtcaactcc gttaggccct tcattgaaag aaatgaggtc atcaaatgtc ttccaatgtg  13020
```

-continued

```
agattttggg ccattttttta tagcaaagat tgaataaggc gcatttttct tca        13073


<210> SEQ ID NO 21
<211> LENGTH: 12851
<212> TYPE: DNA
<213> ORGANISM: Saccharomyces cerevisiae

<400> SEQUENCE: 21

aagcttagct aagcttcgcg gccgcgcaga aatgatgaag ggtgttagcg ccgtccactg     60

atgtgcctgg tagtcatgat ttacgtataa ctaacacatc atgaggacgg cggcgtcacc    120

ccaacgcaaa agagtgactt ccctgcgctt tgccaaaacc ccatacatcg ccatctggct    180

cctggcaggg cggttgatgg acatcagccg cctcccttaa ttgctaaagc ctccacaagg    240

cacaattaag caatatttcg ggaaagtaca ccagtcagtt tgcgctttta tgactgggtt    300

ctaaggtact agatgtgaag tagtggtgac agaatcaggg agataagagg gagcagggtg    360

gggtaatgat gtgcgataac aatcttgctt ggctaatcac ccccatatct tgtagtgagt    420

atataaatag gagcctccct tcctattgca actccataaa attttttttt gtagccactt    480

ctgtaacaag ataaataaaa ccaactaatc gagatatcac atatggaaga cgccaaaaac    540

ataaagaaag gcccggcgcc attctatccg ctggaagatg gaaccgctgg agagcaactg    600

cataaggcta tgaagagata cgccctggtt cctggaacaa ttgcttttac agatgcacat    660

atcgaggtgg acatcactta cgctgagtac ttcgaaatgt ccgttcggtt ggcagaagct    720

atgaaacgat atgggctgaa tacaaatcac agaatcgtcg tatgcagtga aaactctctt    780

caattcttta tgccggtgtt gggcgcgtta tttatcggag ttgcagttgc gcccgcgaac    840

gacatttata atgaacgtga attgctcaac agtatgggca tttcgcagcc taccgtggtg    900

ttcgtttcca aaaaggggtt gcaaaaaatt ttgaacgtgc aaaaaaagct cccaatcatc    960

caaaaaatta ttatcatgga ttctaaaacg gattaccagg gatttcagtc gatgtacacg   1020

ttcgtcacat ctcatctacc tcccggtttt aatgaatacg attttgtgcc agagtccttc   1080

gatagggaca agacaattgc actgatcatg aactcctctg gatctactgg tctgcctaaa   1140

ggtgtcgctc tgcctcatag aactgcctgc gtgagattct cgcatgccag agatcctatt   1200

tttggcaatc aaatcattcc ggatactgcg attttaagtg ttgttccatt ccatcacggt   1260

tttggaatgt ttactacact cggatatttg atatgtggat ttcgagtcgt cttaatgtat   1320

agatttgaag aagagctgtt tctgaggagc cttcaggatt acaagattca aagtgcgctg   1380

ctggtgccaa ccctattctc cttcttcgcc aaaagcactc tgattgacaa atacgattta   1440

tctaatttac acgaaattgc ttctggtggc gctcccctct ctaaggaagt cggggaagcg   1500

gttgccaaga ggttccatct gccaggtatc aggcaaggat atgggctcac tgagactaca   1560

tcagctattc tgattacacc cgagggggat gataaaccgg gcgcggtcgg taaagttgtt   1620

ccattttttg aagcgaaggt tgtggatctg gataccggga aaacgctggg cgttaatcaa   1680

agaggcgaac tgtgtgtgag aggtcctatg attatgtccg gttatgtaaa caatccggaa   1740

gcgaccaacg ccttgattga caaggatgga tggctacatt ctggagacat agcttactgg   1800

gacgaagacg aacacttctt catcgttgac cgcctgaagt ctctgattaa gtacaaaggc   1860

tatcaggtgg ctcccgctga attggaatcc atcttgctcc aacaccccaa catcttcgac   1920

gcaggtgtcg caggtcttcc cgacgatgac gccggtgaac ttcccgccgc cgttgttgtt   1980

ttggagcacg gaaagacgat gacggaaaaa gagatcgtgg attacgtcgc cagtcaagta   2040

acaaccgcaa aaagttgcgc ggaggagttg tgtttgtgga cgaagtaccg aaaggtctta   2100
```

-continued

```
ccggaaaact cgacgcaaga aaaatcagag agatcctcat aaaggccaag aagggcggaa   2160
agatcgccgt gtaattggat ccagtttaaa cagtagcttt ggacttcttc gccagaggtt   2220
tggtcaagtc tccaatcaag gttgtcggct tgtctacctt gccagaaatt tacgaaaaga   2280
tggaaaaggg tcaaatcgtt ggtagatacg ttgttgacac ttctaaataa gcgaatttct   2340
tatgatttat gatttttatt attaaataag ttataaaaaa aataagtgta tacaaatttt   2400
aaagtgactc ttaggtttta aaacgaaaat tcttgttctt gagtaactct ttcctgtagg   2460
tcaggttgct ttctcaggta tagcatgagg tcgctcttat tgaccacacc tctaccggca   2520
tgccgagcaa atgcctgcaa atcgctcccc atttcaccca attgtagata tgctaactcc   2580
agcaatgagt tgatgaatct cggtgtgtat tttatgtcct cagaagacaa cacctgttgt   2640
aatcgttctt ccacacggat cgcggccgct tgatcctcta cgccggacgc atcgtggccg   2700
gcatcaccgg cgccacaggt gcggttgctg gcgcctatat cgccgacatc accgatgggg   2760
aagatcgggc tcgccacttc gggctcatga gcgcttgttt cggcgtgggt atggtggcag   2820
gccccgtggc cgggggactg ttgggcgcca tctccttgca tgcaccattc cttgcggcgg   2880
cggtgctcaa cggcctcaac ctactactgg gctgcttcct aatgcaggag tcgcataagg   2940
gagagcgtcg accgatgccc ttgagagcct tcaacccagt cagctccttc cggtgggcgc   3000
ggggcatgac tatcgtcgcc gcacttatga ctgtcttctt tatcatgcaa ctcgtaggac   3060
aggtgccggc agcgctctgg gtcattttcg gcgaggaccg ctttcgctgg agcgcgacga   3120
tgatcggcct gtcgcttgcg gtattcggaa tcttgcacgc cctcgctcaa gccttcgtca   3180
ctggtcccgc caccaaacgt ttcggcgaga agcaggccat tatcgccggc atggcggccg   3240
acgcgctggg ctacgtcttg ctggcgttcg cgacgcgagg ctggatggcc ttccccatta   3300
tgattcttct cgcttccggc ggcatcggga tgcccgcgtt gcaggccatg ctgtccaggc   3360
aggtagatga cgaccatcag ggacagcttc aaggatcgct cgcggctctt accagcctaa   3420
cttcgatcac tggaccgctg atcgtcacgg cgatttatgc cgcctcggcg agcacatgga   3480
acgggttggc atggattgta ggcgccgccc tataccttgt ctgcctcccc gcgttgcgtc   3540
gcggtgcatg gagccgggcc acctcgacct gaatggaagc cggcggcacc tcgctaacgg   3600
attcaccact ccaagaattg gagccaatca attcttgcgg agaactgtga atgcgcaaac   3660
caacccttgg cagaacatat ccatcgcgtc cgccatctcc agcagccgca cgcggcgcat   3720
ctcgggcagc gttgggtcct ggccacgggt gcgcatgatc gtgctcctgt cgttgaggac   3780
ccggctaggc tggcggggtt gccttactgg ttagcagaat gaatcaccga tacgcgagcg   3840
aacgtgaagc gactgctgct gcaaaacgtc tgcgacctga gcaacaacat gaatggtctt   3900
cggtttccgt gtttcgtaaa gtctggaaac gcggaagtca gcgccctgca ccattatgtt   3960
ccggatctgc atcgcaggat gctgctggct accctgtgga acacctacat ctgtattaac   4020
gaagcgctgg cattgaccct gagtgatttt tctctggtcc cgccgcatcc ataccgccag   4080
ttgtttaccc tcacaagttc cagtaaccgg gcatgttcat catcagtaac ccgtatcgtg   4140
agcatcctct ctcgtttcat cggtatcatt acccccatga acagaaattc ccccttacac   4200
ggaggcatca agtgaccaaa caggaaaaaa ccgcccttaa catggcccgc tttatcagaa   4260
gccagacatt aacgcttctg gagaaactca acgagctgga cgcggatgaa caggcagaca   4320
tctgtgaatc gcttcacgac cacgctgatg agctttaccg cagctgcctc gcgcgtttcg   4380
gtgatgacgg tgaaaacctc tgacacatgc agctcccgga gacggtcaca gcttgtctgt   4440
```

-continued

```
aagcggatgc cgggagcaga caagcccgtc agggcgcgtc agcgggtgtt ggcgggtgtc   4500
ggggcgcagc catgacccag tcacgtagcg atagcggagt gtatactggc ttaactatgc   4560
ggcatcagag cagattgtac tgagagtgca cgatatccgg tgtgaaatac cgcacagatg   4620
cgtaaggaga aaataccgca tcaggcgctc ttccgcttcc tcgctcactg actcgctgcg   4680
ctcggtcgtt cggctgcggc gagcggtatc agctcactca aaggcggtaa tacggttatc   4740
cacagaatca ggggataacg caggaaagaa catgtgagca aaaggccagc aaaaggccag   4800
gaaccgtaaa aaggccgcgt tgctggcgtt tttccatagg ctccgccccc ctgacgagca   4860
tcacaaaaat cgacgctcaa gtcagaggtg gcgaaacccg acaggactat aaagatacca   4920
ggcgtttccc cctggaagct ccctcgtgcg ctctcctgtt ccgaccctgc cgcttaccgg   4980
atacctgtcc gcctttctcc cttcgggaag cgtggcgctt tctcaatgct cacgctgtag   5040
gtatctcagt tcggtgtagg tcgttcgctc caagctgggc tgtgtgcacg aaccccccgt   5100
tcagcccgac cgctgcgcct tatccggtaa ctatcgtctt gagtccaacc cggtaagaca   5160
cgacttatcg ccactggcag cagccactgg taacaggatt agcagagcga ggtatgtagg   5220
cggtgctaca gagttcttga agtggtggcc taactacggc tacactagaa ggacagtatt   5280
tggtatctgc gctctgctga agccagttac cttcggaaaa agagttggta gctcttgatc   5340
cggcaaacaa accaccgctg gtagcggtgg tttttttgtt tgcaagcagc agattacgcg   5400
cagaaaaaaa ggatctcaag aagatccttt gatcttttct acggggtctg acgctcagtg   5460
gaacgaaaac tcacgttaag ggattttggt catgagatta tcaaaaagga tcttcaccta   5520
gatcctttta aattaaaaat gaagttttaa atcaatctaa agtatatatg agtaaacttg   5580
gtctgacagt taccaatgct taatcagtga ggcacctatc tcagcgatct gtctatttcg   5640
ttcatccata gttgcctgac tccccgtcgt gtagataact acgatacggg agggcttacc   5700
atctggcccc agtgctgcaa tgataccgcg agacccacgc tcaccggctc cagatttatc   5760
agcaataaac cagccagccg gaagggccga gcgcagaagt ggtcctgcaa ctttatccgc   5820
ctccatccag tctattaatt gttgccggga agctagagta agtagttcgc cagttaatag   5880
tttgcgcaac gttgttgcca ttgctgcagg catcgtggtg tcacgctcgt cgtttggtat   5940
ggcttcattc agctccggtt cccaacgatc aaggcgagtt acatgatccc ccatgttgtg   6000
caaaaaagcg gttagctcct tcggtcctcc gatcgttgtc agaagtaagt tggccgcagt   6060
gttatcactc atggttatgg cagcactgca taattctctt actgtcatgc catccgtaag   6120
atgcttttct gtgactggtg agtatcaacc aagtcattct gagaatagtg tatgcggcga   6180
ccgagttgct cttgcccggc gtcaacacgg gataataccg cgccacatag cagaacttta   6240
aaagtgctca tcattggaaa acgttcttcg gggcgaaaac tctcaaggat cttaccgctg   6300
ttgagatcca gttcgatgta acccactcgt gcacccaact gatcttcagc atcttttact   6360
ttcaccagcg tttctgggtg agcaaaaaca ggaaggcaaa atgccgcaaa aaagggaata   6420
agggcgacac ggaaatgttg aatactcata ctcttccttt ttcaatatta ttgaagcatt   6480
tatcagggtt attgtctcat gagcggatac atatttgaat gtatttagaa aaataaacaa   6540
ataggggttc cgcgcacatt tccccgaaaa gtgccacctg acgtctaaga aaccattatt   6600
atcatgacat taacctataa aaataggcgt atcacgaggc cctttcgtct tcaagaattc   6660
cacggactat agactatact agtatactcc gtctactgta cgatacactt ccgctcaggt   6720
ccttgtcctt taacgaggcc ttaccactct tttgttactc tattgatcca gctcagcaaa   6780
ggcagtgtga tctaagattc tatcttcgcg atgtagtaaa actagctaga ccgagaaaga   6840
```

-continued

```
gactagaaat gcaaaaggca cttctacaat ggctgccatc attattatcc gatgtgacgc   6900
tgcagaagca gaaatacacg cggtcagtga agctattccg ctattgaata acctcagtca   6960
ccttgtgcaa gaacttaaca agaaaccaat tattaaaggc ttacttactg atagtagatc   7020
aacgatcagt ataattaagt ctacaaatga agagaaattt agaaacagat tttttggcac   7080
aaaggcaatg agacttagag atgaagtatc aggtaataat ttatacgtat actacatcga   7140
gaccaagaag aacattgctg atgtgatgac aaaacctctt ccgataaaaa catttaaact   7200
attaactaac aaatggattc attagatcta ttacattatg ggtggtatgt tggaataaaa   7260
atcaactatc atctactaac tagtatttac gttactagta tattatcata tacggtgtta   7320
gaagatgacg caaatgatga gaaatagtca tctaaattag tggaagctga aacgcaagga   7380
ttgataatgt aataggatca atgaatatta acatataaaa tgatgataat aatatttata   7440
gaattgtgta gaattgcaga ttccctttta tggattccta aatcctcgag gagaacttct   7500
agtatatcta catacctaat attattgcct tattaaaaat ggaatcccaa caattacatc   7560
aaaatccaca ttctcttcaa aatcaattgt cctgtacttc cttgttcatg tgtgttcaaa   7620
aacgttatat ttataggata attatactct atttctcaac aagtaattgg ttgtttggcc   7680
gagcggtcta aggcgcctga ttcaagaaat atcttgaccg cagttaactg tgggaatact   7740
caggtatcgt aagatgcaag agttcgaatc tcttagcaac cattattttt ttcctcaaca   7800
taacgagaac acacaggggc gctatcgcac agaatcaaat tcgatgactg gaaatttttt   7860
gttaatttca gaggtcgcct gacgcatata ccttttttcaa ctgaaaaatt gggagaaaaa   7920
ggaaaggtga gagccgcgga accggctttt catatagaat agagaagcgt tcatgactaa   7980
atgcttgcat cacaatactt gaagttgaca atattattta aggacctatt gtttttttcca   8040
ataggtggtt agcaatcgtc ttactttcta actttctta ccttttacat ttcagcaata   8100
tatatatata tatttcaagg atataccatt ctaatgtctg cccctaagaa gatcgtcgtt   8160
ttgccaggtg accacgttgg tcaagaaatc acgccgaagc cattaaggtt cttaaagcta   8220
tttctgatgt tcgttccaat gtcaagttcg atttcgaaaa tcatttaatt ggtggtgctg   8280
ctatcgatgc tacaggtgtc ccacttccag atgaggcgct ggaagcctcc aagaaggttg   8340
atgccgtttt gttaggtgct gtgggtggtc ctaaatgggg taccggtagt gttagacctg   8400
aacaaggttt actaaaaatc cgtaaagaac ttcaattgta cgccaactta agaccatgta   8460
actttgcatc cgactctctt ttagacttat ctccaatcaa gccacaattt gctaaaggta   8520
ctgacttcgt tgttgtcaga gaattagtgg gaggtattta ctttggtaag agaaaggaag   8580
acgatggtga tggtgtcgct tgggatagtg aacaatacac cgttccagaa gtgcaaagaa   8640
tcacaagaat ggccgctttc atggccctac aacatgagcc accattgcct atttggtcct   8700
tggataaagc taatgttttg gcctcttcaa gattatggag aaaaactgtg gaggaaacca   8760
tcaagaacga attccctaca ttgaaggttc aacatcaatt gattgattct gccgccatga   8820
tcctagttaa gaacccaacc cacctaaatg gtattataat caccagcaac atgtttggtg   8880
atatcatctc cgatgaagcc tccgttatcc caggttcctt gggtttgttg ccatctgcgt   8940
ccttggcctc tttgccagac aagaacaccg catttggttt gtacgaacca tgccacggtt   9000
ctgctccaga tttgccaaag aataaggtca accctatcgc cactatcttg tctgctgcaa   9060
tgatgttgaa attgtcattg aacttgcctg aagaaggtaa ggccattgaa gatgcagtta   9120
aaaaggtttt ggatgcaggt atcagaactg gtgatttagg tggttccaac agtaccacgg   9180
```

-continued

```
aagtcggtga tgctgtcgcc gaagaagtta agaaaatcct tgcttaaaaa gattctcttt   9240
ttttatgata tttgtacata aactttataa atgaaattca taatagaaac gacacgaaat   9300
tacaaaatgg aatatgttca tagggtagac gaaactatat acgcaatcta catacattta   9360
tcaagaagga gaaaaaggag gatgtaaagg aatacaggta agcaaattga tactaatggc   9420
tcaacgtgat aaggaaaaag aattgcactt taacattaat attgacaagg aggagggcac   9480
cacacaaaaa gttaggtgta acagaaaatc atgaaactat gattcctaat ttatatattg   9540
gaggattttc tctaaaaaaa aaaaaataca acaaataaaa aacactcaat gacctgacca   9600
tttgatggag tttaagtcaa taccttcttg aaccatttcc cataatggtg aaagttccct   9660
caagaatttt actctgtcag aaacggcctt aacgacgtag tcgacctcct cttcagtact   9720
aaatctacca ataccaaatc tgatggaaga atgggctaat gcatcatcct tacccagcgc   9780
atgtaaaaca taagaaggtt ctagggaagc agatgtacag gctgaacccg aggataatgc   9840
gatatccctt agtgccatca ataaagattc tccttccacg taggcgaaag aaacgttaac   9900
acaccctgga taacgatgat ctggagatcc gttcaacgtg gtatgttcag cggataatag   9960
acctttgact aatttatcgg atagtctttt gatgtgagct tggtcgttgt caaattcttt  10020
cttcatcaat ctcgcagctt caccaaatcc cgctaccaat ggggggcca aagtaccaga  10080
tctcaatcct ctctcttggc caccaccgga tagtaaaggt tctaatctaa ctcttggtct  10140
ccttcttaca tagatggcac ctattccctt tggaccgtaa atcttgtgag aagaaattga  10200
tagtaaatca atgttcattt cattgacatc aatgtgaatc taccataggc ttgtgcggcg  10260
tcagtatgaa agtagatctt attctttcta caaattgcac caatttcttt aataggttga  10320
atgacaccga tttcattatt gacagccatc acagagacga gacaggtatc tggtctaatg  10380
gcatcttcca attccttcaa atcgataaga ccttgatcgt ccacatttag gaaagtgact  10440
tcaaatccct ccttcatcat ggcccgtgcg gcttccaaga cacacttgtg ttccgttcta  10500
gtggtgatga tgtgtttctt agtcttctta taaaatcttg ggacaccctt aagaaccata  10560
ttattagatt cggtcgctcc cgaagtgaat attatttcct tggggtcggc attgatcatc  10620
tttgctacgt aagctctagc attttccaca gcagtatttg tttcccaacc gtaagagtga  10680
gtgttggaat gaggattacc ataaagtccc gtataaaact tcaacatcgt atccaaaacc  10740
ctagggtctg ttggtgtagt ggcttgcatg tcaagatata tgggacgagt accaaaacct  10800
gtgttttctt gataagcatg gctcattgca gtgctaccag aagctactac agcatctggg  10860
gtggtaccgg atgcactcgc acgggcacta gcctgtgcct ttgcagcagc ctgaatatcg  10920
gtatgcgttt ccagagagaa gttgtcgtct aacttcacgc ctgctgcagt ctcaatgata  10980
ttcgaatacg ctttgaggag atacagccta atatccgaca aactgtttta cagatttacg  11040
atcgtacttg ttacccatca ttgaattttg aacatccgaa cctgggagtt ttccctgaaa  11100
cagatagtat atttgaacct gtataataat atatagtcta gcgctttacg gaagacaatg  11160
tatgtatttc ggttcctgga gaaactattg catctattgc ataggtaatc ttgcacgtcg  11220
catccccggt tcattttctg cgtttccatc ttgcacttca atagcatatc tttgttaacg  11280
aagcatctgt gcttcatttt gtagaacaaa aatgcaacgc gagagcgcta atttttcaaa  11340
caaagaatct gagctgcatt tttacagaac agaaatgcaa cgcgaaagcg ctattttacc  11400
aacgaagaat ctgtgcttca tttttgtaaa acaaaaatgc aacgcgagag cgctaatttt  11460
tcaaacaaag aatctgagct gcatttttac agaacagaaa tgcaacgcga gagcgctatt  11520
ttaccaacaa agaatctata cttctttttt gttctacaaa aatgcatccc gagagcgcta  11580
```

```
tttttctaac aaagcatctt agattacttt ttttctcctt tgtgcgctct ataatgcagt  11640
ctcttgataa ctttttgcac tgtaggtccg ttaaggttag aagaaggcta ctttggtgtc  11700
tattttctct tccataaaaa aagcctgact ccacttcccg cgtttactga ttactagcga  11760
agctgcgggt gcattttttc aagataaagg catccccgat tatattctat accgatgtgg  11820
attgcgcata ctttgtgaac agaaagtgat agcgttgatg attcttcatt ggtcagaaaa  11880
ttatgaacgg tttcttctat tttgtctcta tatactacgt ataggaaatg tttacatttt  11940
cgtattgttt tcgattcact ctatgaatag ttcttactac aattttttttg tctaaagagt  12000
aatactagag ataaacataa aaaatgtaga ggtcgagttt agatgcaagt tcaaggagcg  12060
aaaggtggat gggtaggtta tatagggata tagcacagag atatatagca aagagatact  12120
tttgagcaat gtttgtggaa gcggtattcg caatatttta gtagctcgtt acagtccggt  12180
gcgtttttgg tttttttgaaa gtgcgtcttc agagcgcttt tggttttcaa aagcgctctg  12240
aagttcctat actttctaga gaataggaac ttcggaatag gaacttcaag cgtttccgaa  12300
aacgagcgct tccgaaaatg caacgcgagc tgcgcacata cagctcactg ttcacgtcgc  12360
acctatatct gcgtgttgcc tgtatatata tatacatgag aagaacggca tagtgcgtgt  12420
ttatgcttaa atgcgtactt atatgcgtct atttatgtag gatgaaaggt agtctagtac  12480
ctcctgtgat attatcccat tccatgcggg gtatcgtatg cttccttcag cactaccctt  12540
tagctgttct atatgctgcc actcctcaat tggattagtc tcatccttca atgctatcat  12600
ttcctttgat attcgatcct aggcatagta ccgagaaact agtgcgaagt agtgatcagg  12660
tattgctgtt atctgatgag tatacgttgt cctggccacg gcagaagcac gcttatcgct  12720
ccaatttccc acaacattag tcaactccgt taggcccttc attgaaagaa atgaggtcat  12780
caaatgtctt ccaatgtgag attttgggcc attttttata gcaaagattg aataaggcgc  12840
atttttcttc a                                                       12851
```

```
<210> SEQ ID NO 22
<211> LENGTH: 12850
<212> TYPE: DNA
<213> ORGANISM: Saccharomyces cerevisiae

<400> SEQUENCE: 22

aagcttcgcg gccgcggagg tctgcttcac gagcgcggtg tgcgcctagt attgccccga     60
cggtccgggt gcctatccct agatttcgtc gtgccccgac ccaaatagtt aaacgtgtgg    120
tttatgggtg caccagggct ttatcgtgtt ttatatcgat ggcgatttgt gcctccagtg    180
tatttttgta tatccaatta aggtttctta cctaatttta tttttatcat ctttagttaa    240
tgctggtttg ctctgtttct gctgctttct gtgcggttct cctcttctct tgtttcttcg    300
tgttgtcccc catcgccgat gggcttatat ggcgtatata tatagagcga gtttttacgt    360
cgaagatcat ctcagtttgc ttgatagcct ttctacttta ttactttcgt ttttaacctc    420
attatacttt agttttcttt gatcggtttt tttctctgta tacttaaaag ttcaaatcaa    480
agaaacatac aaaactacgt ttatatcaat tacatatgga agacgccaaa aacataaaga    540
aaggcccggc gccattctat ccgctggaag atggaaccgc tggagagcaa ctgcataagg    600
ctatgaagag atacgccctg gttcctggaa caattgcttt tacagatgca catatcgagg    660
tggacatcac ttacgctgag tacttcgaaa tgtccgttcg gttggcagaa gctatgaaac    720
gatatgggct gaatacaaat cacagaatcg tcgtatgcag tgaaaactct cttcaattct    780
```

-continued

```
ttatgccggt gttgggcgcg ttatttatcg gagttgcagt tgcgcccgcg aacgacattt    840
ataatgaacg tgaattgctc aacagtatgg gcatttcgca gcctaccgtg gtgttcgttt    900
ccaaaaaggg gttgcaaaaa attttgaacg tgcaaaaaaa gctcccaatc atccaaaaaa    960
ttattatcat ggattctaaa acggattacc agggatttca gtcgatgtac acgttcgtca   1020
catctcatct acctcccggt tttaatgaat acgattttgt gccagagtcc ttcgataggg   1080
acaagacaat tgcactgatc atgaactcct ctggatctac tggtctgcct aaaggtgtcg   1140
ctctgcctca tagaactgcc tgcgtgagat tctcgcatgc cagagatcct atttttggca   1200
atcaaatcat tccggatact gcgattttaa gtgttgttcc attccatcac ggttttggaa   1260
tgtttactac actcggatat ttgatatgtg gatttcgagt cgtcttaatg tatagatttg   1320
aagaagagct gtttctgagg agccttcagg attacaagat tcaaagtgcg ctgctggtgc   1380
caaccctatt ctccttcttc gccaaaagca ctctgattga caaatacgat ttatctaatt   1440
tacacgaaat tgcttctggt ggcgctcccc tctctaagga agtcggggaa gcggttgcca   1500
agaggttcca tctgccaggt atcaggcaag gatatgggct cactgagact acatcagcta   1560
ttctgattac acccgagggg gatgataaac cgggcgcggt cggtaaagtt gttccatttt   1620
ttgaagcgaa ggttgtggat ctggataccg ggaaaacgct gggcgttaat caaagaggcg   1680
aactgtgtgt gagaggtcct atgattatgt ccggttatgt aaacaatccg gaagcgacca   1740
acgccttgat tgacaaggat ggatggctac attctggaga catagcttac tgggacgaag   1800
acgaacactt cttcatcgtt gaccgcctga agtctctgat taagtacaaa ggctatcagg   1860
tggctcccgc tgaattggaa tccatcttgc tccaacaccc caacatcttc gacgcaggtg   1920
tcgcaggtct tcccgacgat gacgccggtg aacttcccgc cgccgttgtt gttttggagc   1980
acggaaagac gatgacggaa aaagagatcg tggattacgt cgccagtcaa gtaacaaccg   2040
cgaaaaagtt gcgcggagga gttgtgtttg tggacgaagt accgaaaggt cttaccggaa   2100
aactcgacgc aagaaaaatc agagagatcc tcataaaggc caagaagggc ggaaagatcg   2160
ccgtgtaatt ggatccagtt taaacagtag ctttggactt cttcgccaga ggtttggtca   2220
agtctccaat caaggttgtc ggcttgtcta ccttgccaga aatttacgaa aagatggaaa   2280
agggtcaaat cgttggtaga tacgttgttg acacttctaa ataagcgaat ttcttatgat   2340
ttatgatttt tattattaaa taagttataa aaaaaataag tgtatacaaa ttttaaagtg   2400
actcttaggt tttaaaacga aaattcttgt tcttgagtaa ctctttcctg taggtcaggt   2460
tgctttctca ggtatagcat gaggtcgctc ttattgacca cacctctacc ggcatgccga   2520
gcaaatgcct gcaaatcgct ccccatttca cccaattgta gatatgctaa ctccagcaat   2580
gagttgatga atctcggtgt gtattttatg tcctcagaag acaacacctg ttgtaatcgt   2640
tcttccacac ggatcgcggc cgcttgatcc tctacgccgg acgcatcgtg gccggcatca   2700
ccggcgccac aggtgcggtt gctggcgcct atatcgccga catcaccgat ggggaagatc   2760
gggctcgcca cttcgggctc atgagcgctt gtttcggcgt gggtatggtg gcaggccccg   2820
tggccggggg actgttgggc gccatctcct tgcatgcacc attccttgcg gcggcggtgc   2880
tcaacggcct caacctacta ctgggctgct tcctaatgca ggagtcgcat aagggagagc   2940
gtcgaccgat gcccttgaga gccttcaacc cagtcagctc cttccggtgg gcgcggggca   3000
tgactatcgt cgccgcactt atgactgtct tctttatcat gcaactcgta ggacaggtgc   3060
cggcagcgct ctgggtcatt ttcggcgagg accgctttcg ctggagcgcg acgatgatcg   3120
gcctgtcgct tgcggtattc ggaatcttgc acgccctcgc tcaagccttc gtcactggtc   3180
```

-continued

```
ccgccaccaa acgtttcggc gagaagcagg ccattatcgc cggcatggcg gccgacgcgc   3240
tgggctacgt cttgctggcg ttcgcgacgc gaggctggat ggccttcccc attatgattc   3300
ttctcgcttc cggcggcatc gggatgcccg cgttgcaggc catgctgtcc aggcaggtag   3360
atgacgacca tcagggacag cttcaaggat cgctcgcggc tcttaccagc ctaacttcga   3420
tcactggacc gctgatcgtc acggcgattt atgccgcctc ggcgagcaca tggaacgggt   3480
tggcatggat tgtaggcgcc gccctatacc ttgtctgcct ccccgcgttg cgtcgcggtg   3540
catggagccg ggccacctcg acctgaatgg aagccggcgg cacctcgcta acggattcac   3600
cactccaaga attggagcca atcaattctt gcggagaact gtgaatgcgc aaaccaaccc   3660
ttggcagaac atatccatcg cgtccgccat ctccagcagc cgcacgcggc gcatctcggg   3720
cagcgttggg tcctggccac gggtgcgcat gatcgtgctc ctgtcgttga ggacccggct   3780
aggctggcgg ggttgcctta ctggttagca gaatgaatca ccgatacgcg agcgaacgtg   3840
aagcgactgc tgctgcaaaa cgtctgcgac ctgagcaaca acatgaatgg tcttcggttt   3900
ccgtgtttcg taaagtctgg aaacgcggaa gtcagcgccc tgcaccatta tgttccggat   3960
ctgcatcgca ggatgctgct ggctaccctg tggaacacct acatctgtat taacgaagcg   4020
ctggcattga ccctgagtga tttttctctg gtcccgccgc atccataccg ccagttgttt   4080
accctcacaa cgttccagta accgggcatg ttcatcatca gtaacccgta tcgtgagcat   4140
cctctctcgt ttcatcggta tcattacccc catgaacaga aattccccct tacacggagg   4200
catcaagtga ccaaacagga aaaaaccgcc cttaacatgg cccgctttat cagaagccag   4260
acattaacgc ttctggagaa actcaacgag ctggacgcgg atgaacaggc agacatctgt   4320
gaatcgcttc acgaccacgc tgatgagctt taccgcagct gcctcgcgcg tttcggtgat   4380
gacggtgaaa acctctgaca catgcagctc ccggagacgg tcacagcttg tctgtaagcg   4440
gatgccggga gcagacaagc ccgtcagggc gcgtcagcgg gtgttggcgg gtgtcggggc   4500
gcagccatga cccagtcacg tagcgatagc ggagtgtata ctggcttaac tatgcggcat   4560
cagagcagat tgtactgaga gtgcacgata tccggtgtga aataccgcac agatgcgtaa   4620
ggagaaaata ccgcatcagg cgctcttccg cttcctcgct cactgactcg ctgcgctcgg   4680
tcgttcggct gcggcgagcg gtatcagctc actcaaaggc ggtaatacgg ttatccacag   4740
aatcagggga taacgcagga aagaacatgt gagcaaaagg ccagcaaaag gccaggaacc   4800
gtaaaaaggc cgcgttgctg gcgtttttcc ataggctccg cccccctgac gagcatcaca   4860
aaaatcgacg ctcaagtcag aggtggcgaa acccgacagg actataaaga taccaggcgt   4920
ttccccctgg aagctccctc gtgcgctctc ctgttccgac cctgccgctt accggatacc   4980
tgtccgcctt tctcccttcg ggaagcgtgg cgctttctca atgctcacgc tgtaggtatc   5040
tcagttcggt gtaggtcgtt cgctccaagc tgggctgtgt gcacgaaccc cccgttcagc   5100
ccgaccgctg cgccttatcc ggtaactatc gtcttgagtc caacccggta agacacgact   5160
tatcgccact ggcagcagcc actggtaaca ggattagcag agcgaggtat gtaggcggtg   5220
ctacagagtt cttgaagtgg tggcctaact acggctacac tagaaggaca gtatttggta   5280
tctgcgctct gctgaagcca gttaccttcg gaaaaagagt tggtagctct tgatccggca   5340
aacaaaccac cgctggtagc ggtggttttt ttgtttgcaa gcagcagatt acgcgcagaa   5400
aaaaaggatc tcaagaagat cctttgatct tttctacggg gtctgacgct cagtggaacg   5460
aaaactcacg ttaagggatt ttggtcatga gattatcaaa aaggatcttc acctagatcc   5520
```

-continued

```
ttttaaatta aaaatgaagt tttaaatcaa tctaaagtat atatgagtaa acttggtctg   5580
acagttacca atgcttaatc agtgaggcac ctatctcagc gatctgtcta tttcgttcat   5640
ccatagttgc ctgactcccc gtcgtgtaga taactacgat acgggagggc ttaccatctg   5700
gccccagtgc tgcaatgata ccgcgagacc cacgctcacc ggctccagat ttatcagcaa   5760
taaaccagcc agccggaagg gccgagcgca gaagtggtcc tgcaacttta tccgcctcca   5820
tccagtctat taattgttgc cgggaagcta gagtaagtag ttcgccagtt aatagtttgc   5880
gcaacgttgt tgccattgct gcaggcatcg tggtgtcacg ctcgtcgttt ggtatggctt   5940
cattcagctc cggttcccaa cgatcaaggc gagttacatg atcccccatg ttgtgcaaaa   6000
aagcggttag ctccttcggt cctccgatcg ttgtcagaag taagttggcc gcagtgttat   6060
cactcatggt tatggcagca ctgcataatt ctcttactgt catgccatcc gtaagatgct   6120
tttctgtgac tggtgagtac tcaaccaagt cattctgaga atagtgtatg cggcgaccga   6180
gttgctcttg cccggcgtca acacgggata ataccgcgcc acatagcaga actttaaaag   6240
tgctcatcat tggaaaacgt tcttcggggc gaaaactctc aaggatctta ccgctgttga   6300
gatccagttc gatgtaaccc actcgtgcac ccaactgatc ttcagcatct tttactttca   6360
ccagcgtttc tgggtgagca aaaacaggaa ggcaaaatgc cgcaaaaaag ggaataaggg   6420
cgacacggaa atgttgaata ctcatactct tcctttttca atattattga agcatttatc   6480
agggttattg tctcatgagc ggatacatat ttgaatgtat ttagaaaaat aaacaaatag   6540
gggttccgcg cacatttccc cgaaaagtgc cacctgacgt ctaagaaacc attattatca   6600
tgacattaac ctataaaaat aggcgtatca cgaggccctt tcgtcttcaa gaattccacg   6660
gactatagac tatactagta tactccgtct actgtacgat acacttccgc tcaggtcctt   6720
gtcctttaac gaggccttac cactcttttg ttactctatt gatccagctc agcaaaggca   6780
gtgtgatcta agattctatc ttcgcgatgt agtaaaacta gctagaccga gaaagagact   6840
agaaatgcaa aaggcacttc tacaatggct gccatcatta ttatccgatg tgacgctgca   6900
gaagcagaaa tacacgcggt cagtgaagct attccgctat tgaataacct cagtcacctt   6960
gtgcaagaac ttaacaagaa accaattatt aaaggcttac ttactgatag tagatcaacg   7020
atcagtataa ttaagtctac aaatgaagag aaatttagaa acagattttt tggcacaaag   7080
gcaatgagac ttagagatga agtatcaggt aataatttat acgtatacta catcgagacc   7140
aagaagaaca ttgctgatgt gatgacaaaa cctcttccga taaaaacatt taaactatta   7200
actaacaaat ggattcatta gatctattac attatgggtg gtatgttgga ataaaaatca   7260
actatcatct actaactagt atttacgtta ctagtatatt atcatatacg gtgttagaag   7320
atgacgcaaa tgatgagaaa tagtcatcta aattagtgga agctgaaacg caaggattga   7380
taatgtaata ggatcaatga atattaacat ataaaatgat gataataata tttatagaat   7440
tgtgtagaat tgcagattcc cttttatgga ttcctaaatc ctcgaggaga acttctagta   7500
tatctacata cctaatatta ttgccttatt aaaaatggaa tcccaacaat tacatcaaaa   7560
tccacattct cttcaaaatc aattgtcctg tacttccttg ttcatgtgtg ttcaaaaacg   7620
ttatatttat aggataatta tactctattt ctcaacaagt aattggttgt ttggccgagc   7680
ggtctaaggc gcctgattca agaaatatct tgaccgcagt taactgtggg aatactcagg   7740
tatcgtaaga tgcaagagtt cgaatctctt agcaaccatt attttttttcc tcaacataac   7800
gagaacacac aggggcgcta tcgcacagaa tcaaattcga tgactggaaa ttttttgtta   7860
atttcagagg tcgcctgacg catatacctt tttcaactga aaaattggga gaaaaaggaa   7920
```

-continued

```
aggtgagagc cgcggaaccg gcttttcata tagaatagag aagcgttcat gactaaatgc   7980
ttgcatcaca atacttgaag ttgacaatat tatttaagga cctattgttt tttccaatag   8040
gtggttagca atcgtcttac tttctaactt ttcttacctt ttacatttca gcaatatata   8100
tatatatatt tcaaggatat accattctaa tgtctgcccc taagaagatc gtcgttttgc   8160
caggtgacca cgttggtcaa gaaatcacag ccgaagccat taaggttctt aaagctattt   8220
ctgatgttcg ttccaatgtc aagttcgatt tcgaaaatca tttaattggt ggtgctgcta   8280
tcgatgctac aggtgtccca cttccagatg aggcgctgga agcctccaag aaggttgatg   8340
ccgttttgtt aggtgctgtg ggtggtccta aatggggtac cggtagtgtt agacctgaac   8400
aaggtttact aaaaatccgt aaagaacttc aattgtacgc caacttaaga ccatgtaact   8460
ttgcatccga ctctctttta gacttatctc caatcaagcc acaatttgct aaaggtactg   8520
acttcgttgt tgtcagagaa ttagtgggag gtatttactt tggtaagaga aaggaagacg   8580
atggtgatgg tgtcgcttgg gatagtgaac aatacaccgt tccagaagtg caaagaatca   8640
caagaatggc cgctttcatg gccctacaac atgagccacc attgcctatt tggtccttgg   8700
ataaagctaa tgttttggcc tcttcaagat tatggagaaa aactgtggag gaaaccatca   8760
agaacgaatt ccctacattg aaggttcaac atcaattgat tgattctgcc gccatgatcc   8820
tagttaagaa cccaacccac ctaaatggta ttataatcac cagcaacatg tttggtgata   8880
tcatctccga tgaagcctcc gttatcccag gttccttggg tttgttgcca tctgcgtcct   8940
tggcctcttt gccagacaag aacaccgcat ttggtttgta cgaaccatgc cacggttctg   9000
ctccagattt gccaaagaat aaggtcaacc ctatcgccac tatcttgtct gctgcaatga   9060
tgttgaaatt gtcattgaac ttgcctgaag aaggtaaggc cattgaagat gcagttaaaa   9120
aggttttgga tgcaggtatc agaactggtg atttaggtgg ttccaacagt accacggaag   9180
tcggtgatgc tgtcgccgaa gaagttaaga aaatccttgc ttaaaaagat tctctttttt   9240
tatgatattt gtacataaac tttataaatg aaattcataa tagaaacgac acgaaattac   9300
aaaatggaat atgttcatag ggtagacgaa actatatacg caatctacat acatttatca   9360
agaaggagaa aaaggaggat gtaaaggaat acaggtaagc aaattgatac taatggctca   9420
acgtgataag gaaaaagaat tgcactttaa cattaatatt gacaaggagg agggcaccac   9480
acaaaaagtt aggtgtaaca gaaaatcatg aaactatgat tcctaattta tatattggag   9540
gattttctct aaaaaaaaaa aaatacaaca aataaaaaac actcaatgac ctgaccattt   9600
gatggagttt aagtcaatac cttcttgaac catttcccat aatggtgaaa gttccctcaa   9660
gaattttact ctgtcagaaa cggccttaac gacgtagtcg acctcctctt cagtactaaa   9720
tctaccaata ccaaatctga tggaagaatg ggctaatgca tcatccttac ccagcgcatg   9780
taaaacataa gaaggttcta gggaagcaga tgtacaggct gaacccgagg ataatgcgat   9840
atcccttagt gccatcaata aagattctcc ttccacgtag gcgaaagaaa cgttaacaca   9900
ccctggataa cgatgatctg gagatccgtt caacgtggta tgttcagcgg ataatagacc   9960
tttgactaat ttatcggata gtcttttgat gtgagcttgg tcgttgtcaa attctttctt  10020
catcaatctc gcagcttcac caaatcccgc taccaatggg ggggccaaag taccagatct  10080
caatcctctc tcttggccac caccggatag taaaggttct aatctaactc ttggtctcct  10140
tcttacatag atggcaccta ttccctttgg accgtaaatc ttgtgagaag aaattgatag  10200
taaatcaatg ttcatttcat tgacatcaat gtgaatctta ccataggctt gtgcggcgtc  10260
```

-continued

```
agtatgaaag tagatcttat tctttctaca aattgcacca atttctttaa taggttgaat  10320
gacaccgatt tcattattga cagccatcac agagacgaga caggtatctg gtctaatggc  10380
atcttccaat tccttcaaat cgataagacc ttgatcgtcc acatttagga aagtgacttc  10440
aaatccctcc ttcatcatgg cccgtgcggc ttccaagaca cacttgtgtt ccgttctagt  10500
ggtgatgatg tgtttcttag tcttcttata aaatcttggg acacccttaa gaaccatatt  10560
attagattcg gtcgctcccg aagtgaatat tatttccttg gggtcggcat tgatcatctt  10620
tgctacgtaa gctctagcat tttccacagc agtatttgtt tcccaaccgt aagagtgagt  10680
gttggaatga ggattaccat aaagtcccgt ataaaacttc aacatcgtat ccaaaaccct  10740
agggtctgtt ggtgtagtgg cttgcatgtc aagatatatg ggacgagtac caaaacctgt  10800
gttttcttga taagcatggc tcattgcagt gctaccagaa gctactacag catctggggt  10860
ggtaccggat gcactcgcac gggcactagc ctgtgccttt gcagcagcct gaatatcggt  10920
atgcgtttcc agagagaagt tgtcgtctaa cttcacgcct gctgcagtct caatgatatt  10980
cgaatacgct ttgaggagat acagcctaat atccgacaaa ctgttttaca gatttacgat  11040
cgtacttgtt acccatcatt gaattttgaa catccgaacc tgggagtttt ccctgaaaca  11100
gatagtatat ttgaacctgt ataataatat atagtctagc gctttacgga agacaatgta  11160
tgtatttcgg ttcctggaga aactattgca tctattgcat aggtaatctt gcacgtcgca  11220
tccccggttc attttctgcg tttccatctt gcacttcaat agcatatctt tgttaacgaa  11280
gcatctgtgc ttcattttgt agaacaaaaa tgcaacgcga gagcgctaat tttcaaaca   11340
aagaatctga gctgcatttt tacagaacag aaatgcaacg cgaaagcgct attttaccaa  11400
cgaagaatct gtgcttcatt tttgtaaaac aaaaatgcaa cgcgagagcg ctaatttttc  11460
aaacaaagaa tctgagctgc atttttacag aacagaaatg caacgcgaga gcgctatttt  11520
accaacaaag aatctatact tctttttgt tctacaaaaa tgcatcccga gagcgctatt   11580
tttctaacaa agcatcttag attacttttt ttctcctttg tgcgctctat aatgcagtct  11640
cttgataact ttttgcactg taggtccgtt aaggttagaa gaaggctact ttggtgtcta  11700
ttttctcttc cataaaaaaa gcctgactcc acttcccgcg tttactgatt actagcgaag  11760
ctgcgggtgc attttttcaa gataaaggca tccccgatta tattctatac cgatgtggat  11820
tgcgcatact ttgtgaacag aaagtgatag cgttgatgat tcttcattgg tcagaaaatt  11880
atgaacggtt tcttctattt tgtctctata tactacgtat aggaaatgtt tacattttcg  11940
tattgttttc gattcactct atgaatagtt cttactacaa tttttttgtc taaagagtaa  12000
tactagagat aaacataaaa aatgtagagg tcgagtttag atgcaagttc aaggagcgaa  12060
aggtggatgg gtaggttata tagggatata gcacagagat atatagcaaa gagatacttt  12120
tgagcaatgt ttgtggaagc ggtattcgca atattttagt agctcgttac agtccggtgc  12180
gtttttggtt ttttgaaagt gcgtcttcag agcgcttttg gttttcaaaa gcgctctgaa  12240
gttcctatac tttctagaga ataggaactt cggaatagga acttcaaagc gtttccgaaa  12300
acgagcgctt ccgaaaatgc aacgcgagct gcgcacatac agctcactgt tcacgtcgca  12360
cctatatctg cgtgttgcct gtatatatat atacatgaga agaacggcat agtgcgtgtt  12420
tatgcttaaa tgcgtactta tatgcgtcta tttatgtagg atgaaaggta gtctagtacc  12480
tcctgtgata ttatcccatt ccatgcgggg tatcgtatgc ttccttcagc actacccttt  12540
agctgttcta tatgctgcca ctcctcaatt ggattagtct catccttcaa tgctatcatt  12600
tcctttgata ttcgatccta ggcatagtac cgagaaacta gtgcgaagta gtgatcaggt  12660
```

-continued attgctgtta tctgatgagt atacgttgtc ctggccacgg cagaagcacg cttatcgctc 12720
caatttccca caacattagt caactccgtt aggcccttca ttgaaagaaa tgaggtcatc 12780
aaatgtcttc caatgtgaga ttttgggcca ttttttatag caaagattga ataaggcgca 12840
tttttcttca 12850

<210> SEQ ID NO 23
<211> LENGTH: 11198
<212> TYPE: DNA
<213> ORGANISM: Saccharomyces cerevisiae

<400> SEQUENCE: 23
agcttcgcgg ccgccgtctg atttccgttt tgggaatcct ttgccgcgcg cccctctcaa 60
aactccgcac aagtcccaga aagcgggaaa gaaataaaac gccaccaaaa aaaaaaaaat 120
aaaagccaat cctcgaagcg tgggtggtag gccctggatt atcccgtaca agtatttctc 180
aggagtaaaa aaaccgtttg ttttggaatt ccccatttcg cggccaccta cgccgctatc 240
tttgcaacaa ctatctgcga taactcagca aattttgcat attcgtgttg cagtattgcg 300
ataatgggag tcttactccc aacataacgg cagaaagaaa tgtgagaaaa ttttgcatcc 360
tttgcctccg ttcaagtata taaagtcggc atgcttgata atctttcttt ccatcctaca 420
ttgttctaat tattcttatt ctcctttatt ctttcctaac ataccaagaa attaatcttc 480
tgtcattcgc ttaaacacta tatcacatat gcggtccgga tccagtttaa acagtagctt 540
tggacttctt cgccagaggt ttggtcaagt ctccaatcaa ggttgtcggc ttgtctacct 600
tgccagaaat ttacgaaaag atggaaaagg gtcaaatcgt tggtagatac gttgttgaca 660
cttctaaata agcgaatttc ttatgattta tgatttttat tattaaataa gttataaaaa 720
aaataagtgt atacaaattt taaagtgact cttaggtttt aaaacgaaaa ttcttgttct 780
tgagtaactc tttcctgtag gtcaggttgc tttctcaggt atagcatgag gtcgctctta 840
ttgaccacac ctctaccggc atgccgagca aatgcctgca aatcgctccc catttcaccc 900
aattgtagat atgctaactc cagcaatgag ttgatgaatc tcggtgtgta ttttatgtcc 960
tcagaagaca acacctgttg taatcgttct tccacacgga tcgcggccgc ttgatcctct 1020
acgccggacg catcgtggcc ggcatcaccg gcgccacagg tgcggttgct ggcgcctata 1080
tcgccgacat caccgatggg gaagatcggg ctcgccactt cgggctcatg agcgcttgtt 1140
tcggcgtggg tatggtggca ggccccgtgg ccgggggact gttgggcgcc atctccttgc 1200
atgcaccatt ccttgcggcg gcggtgctca acggcctcaa cctactactg ggctgcttcc 1260
taatgcagga gtcgcataag ggagagcgtc gaccgatgcc cttgagagcc ttcaacccag 1320
tcagctcctt ccggtgggcg cggggcatga ctatcgtcgc cgcacttatg actgtcttct 1380
ttatcatgca actcgtagga caggtgccgg cagcgctctg ggtcattttc ggcgaggacc 1440
gctttcgctg gagcgcgacg atgatcggcc tgtcgcttgc ggtattcgga atcttgcacg 1500
ccctcgctca agccttcgtc actggtcccg ccaccaaacg tttcggcgag aagcaggcca 1560
ttatcgccgg catggcggcc gacgcgctgg gctacgtctt gctggcgttc gcgacgcgag 1620
gctggatggc cttccccatt atgattcttc tcgcttccgg cggcatcggg atgcccgcgt 1680
tgcaggccat gctgtccagg caggtagatg acgaccatca gggacagctt caaggatcgc 1740
tcgcggctct taccagccta acttcgatca ctggaccgct gatcgtcacg gcgatttatg 1800
ccgcctcggc gagcacatgg aacgggttgg catggattgt aggcgccgcc ctataccttg 1860

-continued

```
tctgcctccc cgcgttgcgt cgcggtgcat ggagccgggc cacctcgacc tgaatggaag   1920
ccggcggcac ctcgctaacg gattcaccac tccaagaatt ggagccaatc aattcttgcg   1980
gagaactgtg aatgcgcaaa ccaacccttg gcagaacata tccatcgcgt ccgccatctc   2040
cagcagccgc acgcggcgca tctcgggcag cgttgggtcc tggccacggg tgcgcatgat   2100
cgtgctcctg tcgttgagga cccggctagg ctggcggggt tgccttactg gttagcagaa   2160
tgaatcaccg atacgcgagc gaacgtgaag cgactgctgc tgcaaaacgt ctgcgacctg   2220
agcaacaaca tgaatggtct tcggtttccg tgtttcgtaa agtctggaaa cgcggaagtc   2280
agcgccctgc accattatgt tccggatctg catcgcagga tgctgctggc taccctgtgg   2340
aacacctaca tctgtattaa cgaagcgctg gcattgaccc tgagtgattt ttctctggtc   2400
ccgccgcatc cataccgcca gttgtttacc ctcacaacgt tccagtaacc gggcatgttc   2460
atcatcagta acccgtatcg tgagcatcct ctctcgtttc atcggtatca ttacccccat   2520
gaacagaaat tcccccttac acggaggcat caagtgacca aacaggaaaa aaccgccctt   2580
aacatggccc gctttatcag aagccagaca ttaacgcttc tggagaaact caacgagctg   2640
gacgcggatg aacaggcaga catctgtgaa tcgcttcacg accacgctga tgagctttac   2700
cgcagctgcc tcgcgcgttt cggtgatgac ggtgaaaacc tctgacacat gcagctcccg   2760
gagacggtca cagcttgtct gtaagcggat gccgggagca gacaagcccg tcagggcgcg   2820
tcagcgggtg ttggcgggtg tcggggcgca gccatgaccc agtcacgtag cgatagcgga   2880
gtgtatactg gcttaactat gcggcatcag agcagattgt actgagagtg cacgatatcc   2940
ggtgtgaaat accgcacaga tgcgtaagga gaaaataccg catcaggcgc tcttccgctt   3000
cctcgctcac tgactcgctg cgctcggtcg ttcggctgcg gcgagcggta tcagctcact   3060
caaaggcggt aatacggtta tccacagaat caggggataa cgcaggaaag aacatgtgag   3120
caaaaggcca gcaaaaggcc aggaaccgta aaaaggccgc gttgctggcg tttttccata   3180
ggctccgccc ccctgacgag catcacaaaa atcgacgctc aagtcagagg tggcgaaacc   3240
cgacaggact ataaagatac caggcgtttc cccctggaag ctccctcgtg cgctctcctg   3300
ttccgaccct gccgcttacc ggatacctgt ccgcctttct cccttcggga agcgtggcgc   3360
tttctcaatg ctcacgctgt aggtatctca gttcggtgta ggtcgttcgc tccaagctgg   3420
gctgtgtgca cgaacccccc gttcagcccg accgctgcgc cttatccggt aactatcgtc   3480
ttgagtccaa cccggtaaga cacgacttat cgccactggc agcagccact ggtaacagga   3540
ttagcagagc gaggtatgta ggcggtgcta cagagttctt gaagtggtgg cctaactacg   3600
gctacactag aaggacagta tttggtatct gcgctctgct gaagccagtt accttcggaa   3660
aaagagttgg tagctcttga tccggcaaac aaaccaccgc tggtagcggt ggtttttttg   3720
tttgcaagca gcagattacg cgcagaaaaa aaggatctca agaagatcct ttgatctttt   3780
ctacggggtc tgacgctcag tggaacgaaa actcacgtta agggattttg gtcatgagat   3840
tatcaaaaag gatcttcacc tagatccttt taaattaaaa atgaagtttt aaatcaatct   3900
aaagtatata tgagtaaact tggtctgaca gttaccaatg cttaatcagt gaggcaccta   3960
tctcagcgat ctgtctattt cgttcatcca tagttgcctg actccccgtc gtgtagataa   4020
ctacgatacg ggagggctta ccatctggcc ccagtgctgc aatgataccg cgagacccac   4080
gctcaccggc tccagattta tcagcaataa accagccagc cggaagggcc gagcgcagaa   4140
gtggtcctgc aactttatcc gcctccatcc agtctattaa ttgttgccgg gaagctagag   4200
taagtagttc gccagttaat agtttgcgca acgttgttgc cattgctgca ggcatcgtgg   4260
```

-continued

```
tgtcacgctc gtcgtttggt atggcttcat tcagctccgg ttcccaacga tcaaggcgag   4320
ttacatgatc ccccatgttg tgcaaaaaag cggttagctc cttcggtcct ccgatcgttg   4380
tcagaagtaa gttggccgca gtgttatcac tcatggttat ggcagcactg cataattctc   4440
ttactgtcat gccatccgta agatgctttt ctgtgactgg tgagtactca accaagtcat   4500
tctgagaata gtgtatgcgg cgaccgagtt gctcttgccc ggcgtcaaca cgggataata   4560
ccgcgccaca tagcagaact ttaaaagtgc tcatcattgg aaaacgttct tcggggcgaa   4620
aactctcaag gatcttaccg ctgttgagat ccagttcgat gtaacccact cgtgcaccca   4680
actgatcttc agcatctttt actttcacca gcgtttctgg gtgagcaaaa acaggaaggc   4740
aaaatgccgc aaaaaaggga ataagggcga cacggaaatg ttgaatactc atactcttcc   4800
tttttcaata ttattgaagc atttatcagg gttattgtct catgagcgga tacatatttg   4860
aatgtattta gaaaaataaa caaatagggg ttccgcgcac atttccccga aaagtgccac   4920
ctgacgtcta agaaaccatt attatcatga cattaaccta taaaaatagg cgtatcacga   4980
ggccctttcg tcttcaagaa ttccacggac tatagactat actagtatac tccgtctact   5040
gtacgataca cttccgctca ggtccttgtc ctttaacgag gccttaccac tcttttgtta   5100
ctctattgat ccagctcagc aaaggcagtg tgatctaaga ttctatcttc gcgatgtagt   5160
aaaactagct agaccgagaa agagactaga aatgcaaaag gcacttctac aatggctgcc   5220
atcattatta tccgatgtga cgctgcagaa gcagaaatac acgcggtcag tgaagctatt   5280
ccgctattga ataacctcag tcaccttgtg caagaactta acaagaaacc aattattaaa   5340
ggcttactta ctgatagtag atcaacgatc agtataatta agtctacaaa tgaagagaaa   5400
tttagaaaca gatttttttgg cacaaaggca atgagactta gagatgaagt atcaggtaat   5460
aatttatacg tatactacat cgagaccaag aagaacattg ctgatgtgat gacaaaacct   5520
cttccgataa aaacatttaa actattaact aacaaatgga ttcattagat ctattacatt   5580
atgggtggta tgttggaata aaaatcaact atcatctact aactagtatt tacgttacta   5640
gtatattatc atatacggtg ttagaagatg acgcaaatga tgagaaatag tcatctaaat   5700
tagtggaagc tgaaacgcaa ggattgataa tgtaatagga tcaatgaata ttaacatata   5760
aaatgatgat aataatattt atagaattgt gtagaattgc agattccctt ttatggattc   5820
ctaaatcctc gaggagaact tctagtatat ctacatacct aatattattg ccttattaaa   5880
aatggaatcc caacaattac atcaaaatcc acattctctt caaaatcaat tgtcctgtac   5940
ttccttgttc atgtgtgttc aaaaacgtta tatttatagg ataattatac tctatttctc   6000
aacaagtaat tggttgtttg gccgagcggt ctaaggcgcc tgattcaaga aatatcttga   6060
ccgcagttaa ctgtgggaat actcaggtat cgtaagatgc aagagttcga atctcttagc   6120
aaccattatt tttttcctca acataacgag aacacacagg ggcgctatcg cacagaatca   6180
aattcgatga ctggaaattt tttgttaatt tcagaggtcg cctgacgcat ataccttttt   6240
caactgaaaa attgggagaa aaaggaaagg tgagagccgc ggaaccggct tttcatatag   6300
aatagagaag cgttcatgac taaatgcttg catcacaata cttgaagttg acaatattat   6360
ttaaggacct attgtttttt ccaataggtg gttagcaatc gtcttacttt ctaacttttc   6420
ttacctttta catttcagca atatatatat atatatttca aggatatacc attctaatgt   6480
ctgcccctaa gaagatcgtc gttttgccag gtgaccacgt tggtcaagaa atcacagccg   6540
aagccattaa ggttcttaaa gctatttctg atgttcgttc caatgtcaag ttcgatttcg   6600
```

-continued

```
aaaatcattt aattggtggt gctgctatcg atgctacagg tgtcccactt ccagatgagg   6660
cgctggaagc ctccaagaag gttgatgccg ttttgttagg tgctgtgggt ggtcctaaat   6720
ggggtaccgg tagtgttaga cctgaacaag gtttactaaa aatccgtaaa gaacttcaat   6780
tgtacgccaa cttaagacca tgtaactttg catccgactc tcttttagac ttatctccaa   6840
tcaagccaca atttgctaaa ggtactgact tcgttgttgt cagagaatta gtgggaggta   6900
tttactttgg taagagaaag gaagacgatg gtgatggtgt cgcttgggat agtgaacaat   6960
acaccgttcc agaagtgcaa agaatcacaa gaatggccgc tttcatggcc ctacaacatg   7020
agccaccatt gcctatttgg tccttggata aagctaatgt tttggcctct tcaagattat   7080
ggagaaaaac tgtggaggaa accatcaaga acgaattccc tacattgaag gttcaacatc   7140
aattgattga ttctgccgcc atgatcctag ttaagaaccc aacccaccta aatggtatta   7200
taatcaccag caacatgttt ggtgatatca tctccgatga agcctccgtt atcccaggtt   7260
ccttgggttt gttgccatct gcgtccttgg cctctttgcc agacaagaac accgcatttg   7320
gtttgtacga accatgccac ggttctgctc cagatttgcc aaagaataag gtcaacccta   7380
tcgccactat cttgtctgct gcaatgatgt tgaaattgtc attgaacttg cctgaagaag   7440
gtaaggccat tgaagatgca gttaaaaagg ttttggatgc aggtatcaga actggtgatt   7500
taggtggttc caacagtacc acggaagtcg gtgatgctgt cgccgaagaa gttaagaaaa   7560
tccttgctta aaaagattct cttttttat gatatttgta cataaacttt ataaatgaaa    7620
ttcataatag aaacgacacg aaattacaaa atggaatatg ttcatagggt agacgaaact   7680
atatacgcaa tctacataca tttatcaaga aggagaaaaa ggaggatgta aaggaataca   7740
ggtaagcaaa ttgatactaa tggctcaacg tgataaggaa aaagaattgc actttaacat   7800
taatattgac aaggaggagg gcaccacaca aaaagttagg tgtaacagaa aatcatgaaa   7860
ctatgattcc taatttatat attggaggat tttctctaaa aaaaaaaaaa tacaacaaat   7920
aaaaaacact caatgacctg accatttgat ggagtttaag tcaatacctt cttgaaccat   7980
ttcccataat ggtgaaagtt ccctcaagaa ttttactctg tcagaaacgg ccttaacgac   8040
gtagtcgacc tcctcttcag tactaaatct accaatacca aatctgatgg aagaatgggc   8100
taatgcatca tccttaccca gcgcatgtaa aacataagaa ggttctaggg aagcagatgt   8160
acaggctgaa cccgaggata atgcgatatc ccttagtgcc atcaataaag attctccttc   8220
cacgtaggcg aaagaaacgt taacacaccc tggataacga tgatctggag atccgttcaa   8280
cgtggtatgt tcagcggata atagaccttt gactaattta tcggatagtc ttttgatgtg   8340
agcttggtcg ttgtcaaatt ctttcttcat caatctcgca gcttcaccaa atcccgctac   8400
caatgggggg gccaaagtac cagatctcaa tcctctctct tggccaccac cggatagtaa   8460
aggttctaat ctaactcttg gtctccttct tacatagatg gcacctattc cctttggacc   8520
gtaaatcttg tgagaagaaa ttgatagtaa atcaatgttc atttcattga catcaatgtg   8580
aatcttacca taggcttgtg cggcgtcagt atgaaagtag atcttattct ttctacaaat   8640
tgcaccaatt tctttaatag gttgaatgac accgatttca ttattgacag ccatcacaga   8700
gacgagacag gtatctggtc taatggcatc ttccaattcc ttcaaatcga taagaccttg   8760
atcgtccaca tttaggaaag tgacttcaaa tccctccttc atcatggccc gtgcggcttc   8820
caagacacac ttgtgttccg ttctagtggt gatgatgtgt ttcttagtct tcttataaaa   8880
tcttgggaca cccttaagaa ccatattatt agattcggtc gctcccgaag tgaatattat   8940
ttccttgggg tcggcattga tcatctttgc tacgtaagct ctagcatttt ccacagcagt   9000
```

```
atttgtttcc caaccgtaag agtgagtgtt ggaatgagga ttaccataaa gtcccgtata   9060
aaacttcaac atcgtatcca aaaccctagg gtctgttggt gtagtggctt gcatgtcaag   9120
atatatggga cgagtaccaa aacctgtgtt ttcttgataa gcatggctca ttgcagtgct   9180
accagaagct actacagcat ctggggtggt accggatgca ctcgcacggg cactagcctg   9240
tgcctttgca gcagcctgaa tatcggtatg cgtttccaga gagaagttgt cgtctaactt   9300
cacgcctgct gcagtctcaa tgatattcga atacgctttg aggagataca gcctaatatc   9360
cgacaaactg ttttacagat ttacgatcgt acttgttacc catcattgaa ttttgaacat   9420
ccgaacctgg gagttttccc tgaaacagat agtatatttg aacctgtata ataatatata   9480
gtctagcgct ttacggaaga caatgtatgt atttcggttc ctggagaaac tattgcatct   9540
attgcatagg taatcttgca cgtcgcatcc ccggttcatt ttctgcgttt ccatcttgca   9600
cttcaatagc atatctttgt taacgaagca tctgtgcttc attttgtaga acaaaaatgc   9660
aacgcgagag cgctaatttt tcaaacaaag aatctgagct gcatttttac agaacagaaa   9720
tgcaacgcga aagcgctatt ttaccaacga agaatctgtg cttcattttt gtaaaacaaa   9780
aatgcaacgc gagagcgcta atttttcaaa caaagaatct gagctgcatt tttacagaac   9840
agaaatgcaa cgcgagagcg ctattttacc aacaaagaat ctatacttct tttttgttct   9900
acaaaaatgc atcccgagag cgctattttt ctaacaaagc atcttagatt actttttttc   9960
tcctttgtgc gctctataat gcagtctctt gataactttt tgcactgtag gtccgttaag  10020
gttagaagaa ggctactttg gtgtctattt tctcttccat aaaaaaagcc tgactccact  10080
tcccgcgttt actgattact agcgaagctg cgggtgcatt ttttcaagat aaaggcatcc  10140
ccgattatat tctataccga tgtggattgc gcatactttg tgaacagaaa gtgatagcgt  10200
tgatgattct tcattggtca gaaaattatg aacggtttct tctattttgt ctctatatac  10260
tacgtatagg aaatgtttac attttcgtat tgttttcgat tcactctatg aatagttctt  10320
actacaattt ttttgtctaa agagtaatac tagagataaa cataaaaaat gtagaggtcg  10380
agtttagatg caagttcaag gagcgaaagg tggatgggta ggttatatag ggatatagca  10440
cagagatata tagcaaagag atacttttga gcaatgtttg tggaagcggt attcgcaata  10500
ttttagtagc tcgttacagt ccggtgcgtt tttggttttt tgaaagtgcg tcttcagagc  10560
gcttttggtt ttcaaaagcg ctctgaagtt cctatacttt ctagagaata ggaacttcgg  10620
aataggaact tcaaagcgtt tccgaaaacg agcgcttccg aaaatgcaac gcgagctgcg  10680
cacatacagc tcactgttca cgtcgcacct atatctgcgt gttgcctgta tatatatata  10740
catgagaaga acggcatagt gcgtgtttat gcttaaatgc gtacttatat gcgtctattt  10800
atgtaggatg aaaggtagtc tagtacctcc tgtgatatta tcccattcca tgcggggtat  10860
cgtatgcttc cttcagcact accctttagc tgttctatat gctgccactc ctcaattgga  10920
ttagtctcat ccttcaatgc tatcatttcc tttgatattc gatcctaggc atagtaccga  10980
gaaactagtg cgaagtagtg atcaggtatt gctgttatct gatgagtata cgttgtcctg  11040
gccacggcag aagcacgctt atcgctccaa tttcccacaa cattagtcaa ctccgttagg  11100
cccttcattg aaagaaatga ggtcatcaaa tgtcttccaa tgtgagattt tgggccattt  11160
tttatagcaa agattgaata aggcgcattt ttcttcaa                         11198
```

<210> SEQ ID NO 24
<211> LENGTH: 11427
<212> TYPE: DNA

<213> ORGANISM: Saccharomyces cerevisiae

<400> SEQUENCE: 24

```
agcttcgcgg ccgcctttcg attagcacgc acacacatca catagactgc gtcataaaaa     60
tacactacgg aaaaaccata aagagcaaag cgatacctac ttggaaggaa aaggagcacg    120
cttgtaaggg ggatgggggc taagaagtca ttcactttct tttcccttcg cggtccggac    180
ccgggacccc tcctctcccc gcacgatttc ttcctttcat atcttccttt tattcctatc    240
ccgttgaagc aaccgcacta tgactaaatg gtgctggaca tctccatggc tgtgacttgt    300
gtgtatctca cagtggtaac ggcaccgtgg ctcggaaacg gttccttcgt gacaattcta    360
gaacaggggc tacagtctcg ataatagaat aataagcgca tttttgctag cgccgccgcg    420
gcgcccgttt cccaataggg aggcgcagtt tatcggcgga gctctacttc ttcctatttg    480
ggtaagcccc tttctgtttt cggccagtgg ttgctgcagg ctgcgccgga gaacatagtg    540
ataagggatg taactttcga tgagagaatt agcaagcgga aaaaaactat ggctagctgg    600
gagttgtttt tcaatcatat aaaagggaga aattgttgct cactatgtga cagtttctgg    660
gacgtcttaa cttttattgc agaggactat caaatcatac agatattgtc aaaaaaaaaa    720
aagactaata ataacatatg cggtccggat ccagtttaaa cagtagcttt ggacttcttc    780
gccagaggtt tggtcaagtc tccaatcaag gttgtcggct tgtctacctt gccagaaatt    840
tacgaaaaga tggaaaaggg tcaaatcgtt ggtagatacg ttgttgacac ttctaaataa    900
gcgaatttct tatgatttat gatttttatt attaaataag ttataaaaaa aataagtgta    960
tacaaatttt aaagtgactc ttaggtttta aaacgaaaat tcttgttctt gagtaactct   1020
ttcctgtagg tcaggttgct ttctcaggta tagcatgagg tcgctcttat tgaccacacc   1080
tctaccggca tgccgagcaa atgcctgcaa atcgctcccc atttcaccca attgtagata   1140
tgctaactcc agcaatgagt tgatgaatct cggtgtgtat tttatgtcct cagaagacaa   1200
cacctgttgt aatcgttctt ccacacggat cgcggccgct tgatcctcta cgccggacgc   1260
atcgtggccg gcatcaccgg cgccacaggt gcggttgctg gcgcctatat cgccgacatc   1320
accgatgggg aagatcgggc tcgccacttc gggctcatga gcgcttgttt cggcgtgggt   1380
atggtggcag gccccgtggc cgggggactg ttgggcgcca tctccttgca tgcaccattc   1440
cttgcggcgg cggtgctcaa cggcctcaac ctactactgg gctgcttcct aatgcaggag   1500
tcgcataagg gagagcgtcg accgatgccc ttgagagcct tcaacccagt cagctccttc   1560
cggtgggcgc ggggcatgac tatcgtcgcc gcacttatga ctgtcttctt tatcatgcaa   1620
ctcgtaggac aggtgccggc agcgctctgg gtcattttcg gcgaggaccg ctttcgctgg   1680
agcgcgacga tgatcggcct gtcgcttgcg gtattcggaa tcttgcacgc cctcgctcaa   1740
gccttcgtca ctggtcccgc caccaaacgt ttcggcgaga agcaggccat tatcgccggc   1800
atggcggccg acgcgctggg ctacgtcttg ctggcgttcg cgacgcgagg ctggatggcc   1860
ttccccatta tgattcttct cgcttccggc ggcatcggga tgcccgcgtt gcaggccatg   1920
ctgtccaggc aggtagatga cgaccatcag ggacagcttc aaggatcgct cgcggctctt   1980
accagcctaa cttcgatcac tggaccgctg atcgtcacgg cgatttatgc cgcctcggcg   2040
agcacatgga acgggttggc atggattgta ggcgccgccc tataccttgt ctgcctcccc   2100
gcgttgcgtc gcggtgcatg gagccgggcc acctcgacct gaatggaagc cggcggcacc   2160
tcgctaacgg attcaccact ccaagaattg gagccaatca attcttgcgg agaactgtga   2220
atgcgcaaac caacccttgg cagaacatat ccatcgcgtc cgccatctcc agcagccgca   2280
```

-continued

```
cgcggcgcat ctcgggcagc gttgggtcct ggccacgggt gcgcatgatc gtgctcctgt   2340
cgttgaggac ccggctaggc tggcggggtt gccttactgg ttagcagaat gaatcaccga   2400
tacgcgagcg aacgtgaagc gactgctgct gcaaaacgtc tgcgacctga gcaacaacat   2460
gaatggtctt cggtttccgt gtttcgtaaa gtctggaaac gcggaagtca gcgccctgca   2520
ccattatgtt ccggatctgc atcgcaggat gctgctggct accctgtgga acacctacat   2580
ctgtattaac gaagcgctgg cattgaccct gagtgatttt tctctggtcc cgccgcatcc   2640
ataccgccag ttgtttaccc tcacaacgtt ccagtaaccg ggcatgttca tcatcagtaa   2700
cccgtatcgt gagcatcctc tctcgtttca tcggtatcat tacccccatg aacagaaatt   2760
ccccttaca cggaggcatc aagtgaccaa acaggaaaaa accgccctta acatggcccg   2820
ctttatcaga agccagacat taacgcttct ggagaaactc aacgagctgg acgcggatga   2880
acaggcagac atctgtgaat cgcttcacga ccacgctgat gagctttacc gcagctgcct   2940
cgcgcgtttc ggtgatgacg gtgaaaacct ctgacacatg cagctcccgg agacggtcac   3000
agcttgtctg taagcggatg ccgggagcag acaagcccgt cagggcgcgt cagcgggtgt   3060
tggcgggtgt cggggcgcag ccatgaccca gtcacgtagc gatagcggag tgtatactgg   3120
cttaactatg cggcatcaga gcagattgta ctgagagtgc acgatatccg gtgtgaaata   3180
ccgcacagat gcgtaaggag aaaataccgc atcaggcgct cttccgcttc ctcgctcact   3240
gactcgctgc gctcggtcgt tcggctgcgg cgagcggtat cagctcactc aaaggcggta   3300
atacggttat ccacagaatc aggggataac gcaggaaaga acatgtgagc aaaaggccag   3360
caaaaggcca ggaaccgtaa aaaggccgcg ttgctggcgt ttttccatag gctccgcccc   3420
cctgacgagc atcacaaaaa tcgacgctca agtcagaggt ggcgaaaccc gacaggacta   3480
taaagatacc aggcgtttcc ccctggaagc tccctcgtgc gctctcctgt tccgaccctg   3540
ccgcttaccg gatacctgtc cgcctttctc ccttcgggaa gcgtggcgct ttctcaatgc   3600
tcacgctgta ggtatctcag ttcggtgtag gtcgttcgct ccaagctggg ctgtgtgcac   3660
gaaccccccg ttcagcccga ccgctgcgcc ttatccggta actatcgtct tgagtccaac   3720
ccggtaagac acgacttatc gccactggca gcagccactg gtaacaggat tagcagagcg   3780
aggtatgtag gcggtgctac agagttcttg aagtggtggc ctaactacgg ctacactaga   3840
aggacagtat ttggtatctg cgctctgctg aagccagtta ccttcggaaa aagagttggt   3900
agctcttgat ccggcaaaca aaccaccgct ggtagcggtg gtttttttgt ttgcaagcag   3960
cagattacgc gcagaaaaaa aggatctcaa gaagatcctt tgatcttttc tacggggtct   4020
gacgctcagt ggaacgaaaa ctcacgttaa gggattttgg tcatgagatt atcaaaaagg   4080
atcttcacct agatcctttt aaattaaaaa tgaagtttta aatcaatcta aagtatatat   4140
gagtaaactt ggtctgacag ttaccaatgc ttaatcagtg aggcacctat ctcagcgatc   4200
tgtctatttc gttcatccat agttgcctga ctccccgtcg tgtagataac tacgatacgg   4260
gagggcttac catctggccc cagtgctgca atgataccgc gagacccacg ctcaccggct   4320
ccagatttat cagcaataaa ccagccagcc ggaagggccg agcgcagaag tggtcctgca   4380
actttatccg cctccatcca gtctattaat tgttgccggg aagctagagt aagtagttcg   4440
ccagttaata gtttgcgcaa cgttgttgcc attgctgcag gcatcgtggt gtcacgctcg   4500
tcgtttggta tggcttcatt cagctccggt tcccaacgat caaggcgagt tacatgatcc   4560
cccatgttgt gcaaaaaagc ggttagctcc ttcggtcctc cgatcgttgt cagaagtaag   4620
```

-continued

```
ttggccgcag tgttatcact catggttatg gcagcactgc ataattctct tactgtcatg   4680

ccatccgtaa gatgcttttc tgtgactggt gagtactcaa ccaagtcatt ctgagaatag   4740

tgtatgcggc gaccgagttg ctcttgcccg gcgtcaacac gggataatac cgcgccacat   4800

agcagaactt taaaagtgct catcattgga aaacgttctt cggggcgaaa actctcaagg   4860

atcttaccgc tgttgagatc cagttcgatg taacccactc gtgcacccaa ctgatcttca   4920

gcatctttta ctttcaccag cgtttctggg tgagcaaaaa caggaaggca aaatgccgca   4980

aaaaagggaa taagggcgac acggaaatgt tgaatactca tactcttcct ttttcaatat   5040

tattgaagca tttatcaggg ttattgtctc atgagcggat acatatttga atgtatttag   5100

aaaaataaac aaataggggt tccgcgcaca tttccccgaa aagtgccacc tgacgtctaa   5160

gaaaccatta ttatcatgac attaacctat aaaaataggc gtatcacgag gccctttcgt   5220

cttcaagaat tccacggact atagactata ctagtatact ccgtctactg tacgatacac   5280

ttccgctcag gtccttgtcc tttaacgagg ccttaccact cttttgttac tctattgatc   5340

cagctcagca aaggcagtgt gatctaagat tctatcttcg cgatgtagta aaactagcta   5400

gaccgagaaa gagactagaa atgcaaaagg cacttctaca atggctgcca tcattattat   5460

ccgatgtgac gctgcagaag cagaaataca cgcggtcagt gaagctattc cgctattgaa   5520

taacctcagt caccttgtgc aagaacttaa caagaaacca attattaaag gcttacttac   5580

tgatagtaga tcaacgatca gtataattaa gtctacaaat gaagagaaat ttagaaacag   5640

attttttggc acaaaggcaa tgagacttag agatgaagta tcaggtaata atttatacgt   5700

atactacatc gagaccaaga agaacattgc tgatgtgatg acaaaacctc ttccgataaa   5760

aacatttaaa ctattaacta acaaatggat tcattagatc tattacatta tgggtggtat   5820

gttggaataa aaatcaacta tcatctacta actagtattt acgttactag tatattatca   5880

tatacggtgt tagaagatga cgcaaatgat gagaaatagt catctaaatt agtggaagct   5940

gaaacgcaag gattgataat gtaataggat caatgaatat taacatataa aatgatgata   6000

ataatattta tagaattgtg tagaattgca gattcccttt tatggattcc taaatcctcg   6060

aggagaactt ctagtatatc tacataccta atattattgc cttattaaaa atggaatccc   6120

aacaattaca tcaaaatcca cattctcttc aaaatcaatt gtcctgtact tccttgttca   6180

tgtgtgttca aaaacgttat atttatagga taattatact ctatttctca acaagtaatt   6240

ggttgtttgg ccgagcggtc taaggcgcct gattcaagaa atatcttgac cgcagttaac   6300

tgtgggaata ctcaggtatc gtaagatgca agagttcgaa tctcttagca accattattt   6360

ttttcctcaa cataacgaga acacacaggg gcgctatcgc acagaatcaa attcgatgac   6420

tggaaatttt ttgttaattt cagaggtcgc ctgacgcata tacctttttc aactgaaaaa   6480

ttgggagaaa aaggaaaggt gagagccgcg gaaccggctt ttcatataga atagagaagc   6540

gttcatgact aaatgcttgc atcacaatac ttgaagttga caatattatt taaggaccta   6600

ttgtttttc caataggtgg ttagcaatcg tcttactttc taacttttct taccttttac   6660

atttcagcaa tatatatata tatatttcaa ggatatacca ttctaatgtc tgcccctaag   6720

aagatcgtcg ttttgccagg tgaccacgtt ggtcaagaaa tcacagccga agccattaag   6780

gttcttaaag ctatttctga tgttcgttcc aatgtcaagt tcgatttcga aaatcattta   6840

attggtggtg ctgctatcga tgctacaggt gtcccacttc cagatgaggc gctggaagcc   6900

tccaagaagg ttgatgccgt tttgttaggt gctgtgggtg gtcctaaatg gggtaccggt   6960

agtgttagac ctgaacaagg tttactaaaa atccgtaaag aacttcaatt gtacgccaac   7020
```

-continued

```
ttaagaccat gtaactttgc atccgactct cttttagact tatctccaat caagccacaa   7080
tttgctaaag gtactgactt cgttgttgtc agagaattag tgggaggtat ttactttggt   7140
aagagaaagg aagacgatgg tgatggtgtc gcttgggata gtgaacaata caccgttcca   7200
gaagtgcaaa gaatcacaag aatggccgct ttcatggccc tacaacatga gccaccattg   7260
cctatttggt ccttggataa agctaatgtt ttggcctctt caagattatg gagaaaaact   7320
gtggaggaaa ccatcaagaa cgaattccct acattgaagg ttcaacatca attgattgat   7380
tctgccgcca tgatcctagt taagaaccca acccacctaa atggtattat aatcaccagc   7440
aacatgtttg gtgatatcat ctccgatgaa gcctccgtta tcccaggttc cttgggtttg   7500
ttgccatctg cgtccttggc ctctttgcca gacaagaaca ccgcatttgg tttgtacgaa   7560
ccatgccacg gttctgctcc agatttgcca aagaataagg tcaaccctat cgccactatc   7620
ttgtctgctg caatgatgtt gaaattgtca ttgaacttgc ctgaagaagg taaggccatt   7680
gaagatgcag ttaaaaaggt tttggatgca ggtatcagaa ctggtgattt aggtggttcc   7740
aacagtacca cggaagtcgg tgatgctgtc gccgaagaag ttaagaaaat ccttgcttaa   7800
aaagattctc ttttttttatg atatttgtac ataaacttta taaatgaaat tcataataga   7860
aacgacacga aattacaaaa tggaatatgt tcatagggta gacgaaacta tatacgcaat   7920
ctacatacat ttatcaagaa ggagaaaaag gaggatgtaa aggaatacag gtaagcaaat   7980
tgatactaat ggctcaacgt gataaggaaa aagaattgca ctttaacatt aatattgaca   8040
aggaggaggg caccacacaa aaagttaggt gtaacagaaa atcatgaaac tatgattcct   8100
aatttatata ttggaggatt ttctctaaaa aaaaaaaaat acaacaaata aaaaacactc   8160
aatgacctga ccatttgatg gagtttaagt caataccttc ttgaaccatt tcccataatg   8220
gtgaaagttc cctcaagaat ttactctgt cagaaacggc cttaacgacg tagtcgacct   8280
cctcttcagt actaaatcta ccaataccaa atctgatgga agaatgggct aatgcatcat   8340
ccttacccag cgcatgtaaa acataagaag gttctaggga agcagatgta caggctgaac   8400
ccgaggataa tgcgatatcc cttagtgcca tcaataaaga ttctccttcc acgtaggcga   8460
aagaaacgtt aacacaccct ggataacgat gatctggaga tccgttcaac gtggtatgtt   8520
cagcggataa tagacctttg actaatttat cggatagtct tttgatgtga gcttggtcgt   8580
tgtcaaattc tttcttcatc aatctcgcag cttcaccaaa tcccgctacc aatggggggg   8640
ccaaagtacc agatctcaat cctctctctt ggccaccacc ggatagtaaa ggttctaatc   8700
taactcttgg tctccttctt acatagatgg cacctattcc ctttggaccg taaatcttgt   8760
gagaagaaat tgatagtaaa tcaatgttca tttcattgac atcaatgtga atcttaccat   8820
aggcttgtgc ggcgtcagta tgaaagtaga tcttattctt tctacaaatt gcaccaattt   8880
ctttaatagg ttgaatgaca ccgatttcat tattgacagc catcacagag acgagacagg   8940
tatctggtct aatggcatct tccaattcct tcaaatcgat aagaccttga tcgtccacat   9000
ttaggaaagt gacttcaaat ccctccttca tcatggcccg tgcggcttcc aagacacact   9060
tgtgttccgt tctagtggtg atgatgtgtt tcttagtctt cttataaaat cttgggacac   9120
ccttaagaac catattatta gattcggtcg ctcccgaagt gaatattatt tccttggggt   9180
cggcattgat catctttgct acgtaagctc tagcattttc cacagcagta tttgtttccc   9240
aaccgtaaga gtgagtgttg gaatgaggat taccataaag tcccgtataa aacttcaaca   9300
tcgtatccaa aaccctaggg tctgttggtg tagtggcttg catgtcaaga tatatgggac   9360
```

-continued

```
gagtaccaaa acctgtgttt tcttgataag catggctcat tgcagtgcta ccagaagcta   9420
ctacagcatc tggggtggta ccggatgcac tcgcacgggc actagcctgt gcctttgcag   9480
cagcctgaat atcggtatgc gtttccagag agaagttgtc gtctaacttc acgcctgctg   9540
cagtctcaat gatattcgaa tacgctttga ggagatacag cctaatatcc gacaaactgt   9600
tttacagatt tacgatcgta cttgttaccc atcattgaat tttgaacatc cgaacctggg   9660
agttttccct gaaacagata gtatatttga acctgtataa taatatatag tctagcgctt   9720
tacggaagac aatgtatgta tttcggttcc tggagaaact attgcatcta ttgcataggt   9780
aatcttgcac gtcgcatccc cggttcattt tctgcgtttc catcttgcac ttcaatagca   9840
tatctttgtt aacgaagcat ctgtgcttca ttttgtagaa caaaaatgca acgcgagagc   9900
gctaattttt caaacaaaga atctgagctg catttttaca gaacagaaat gcaacgcgaa   9960
agcgctattt taccaacgaa gaatctgtgc ttcatttttg taaaacaaaa atgcaacgcg  10020
agagcgctaa tttttcaaac aaagaatctg agctgcattt ttacagaaca gaaatgcaac  10080
gcgagagcgc tattttacca acaaagaatc tatacttctt ttttgttcta caaaaatgca  10140
tcccgagagc gctatttttc taacaaagca tcttagatta cttttttttct cctttgtgcg  10200
ctctataatg cagtctcttg ataacttttt gcactgtagg tccgttaagg ttagaagaag  10260
gctactttgg tgtctatttt ctcttccata aaaaaagcct gactccactt cccgcgttta  10320
ctgattacta gcgaagctgc gggtgcattt tttcaagata aaggcatccc cgattatatt  10380
ctataccgat gtggattgcg catactttgt gaacagaaag tgatagcgtt gatgattctt  10440
cattggtcag aaaattatga acggtttctt ctattttgtc tctatatact acgtatagga  10500
aatgtttaca ttttcgtatt gttttcgatt cactctatga atagttctta ctacaatttt  10560
tttgtctaaa gagtaatact agagataaac ataaaaaatg tagaggtcga gtttagatgc  10620
aagttcaagg agcgaaaggt ggatgggtag gttatatagg gatatagcac agagatatat  10680
agcaaagaga tacttttgag caatgtttgt ggaagcggta ttcgcaatat tttagtagct  10740
cgttacagtc cggtgcgttt ttggtttttt gaaagtgcgt cttcagagcg cttttggttt  10800
tcaaaagcgc tctgaagttc ctatactttc tagagaatag gaacttcgga ataggaactt  10860
caaagcgttt ccgaaaacga gcgcttccga aaatgcaacg cgagctgcgc acatacagct  10920
cactgttcac gtcgcaccta tatctgcgtg ttgcctgtat atatatatac atgagaagaa  10980
cggcatagtg cgtgtttatg cttaaatgcg tacttatatg cgtctattta tgtaggatga  11040
aaggtagtct agtacctcct gtgatattat cccattccat gcggggtatc gtatgcttcc  11100
ttcagcacta ccctttagct gttctatatg ctgccactcc tcaattggat tagtctcatc  11160
cttcaatgct atcatttcct ttgatattcg atcctaggca tagtaccgag aaactagtgc  11220
gaagtagtga tcaggtattg ctgttatctg atgagtatac gttgtcctgg ccacggcaga  11280
agcacgctta tcgctccaat ttcccacaac attagtcaac tccgttaggc ccttcattga  11340
aagaaatgag gtcatcaaat gtcttccaat gtgagatttt gggccatttt ttatagcaaa  11400
gattgaataa ggcgcatttt tcttcaa                                      11427
```

<210> SEQ ID NO 25
<211> LENGTH: 11201
<212> TYPE: DNA
<213> ORGANISM: Saccharomyces cerevisiae

<400> SEQUENCE: 25

```
aagcttcgcg gccgcgcaga aatgatgaag ggtgttagcg ccgtccactg atgtgcctgg     60
```

-continued

```
tagtcatgat ttacgtataa ctaacacatc atgaggacgg cggcgtcacc ccaacgcaaa    120
agagtgactt ccctgcgctt tgccaaaacc ccatacatcg ccatctggct cctggcaggg    180
cggttgatgg acatcagccg cctcccttaa ttgctaaagc ctccacaagg cacaattaag    240
caatatttcg ggaaagtaca ccagtcagtt tgcgctttta tgactgggtt ctaaggtact    300
agatgtgaag tagtggtgac agaatcaggg agataagagg gagcagggtg gggtaatgat    360
gtgcgataac aatcttgctt ggctaatcac ccccatatct tgtagtgagt atataaatag    420
gagcctccct tcctattgca actccataaa attttttttt gtagccactt ctgtaacaag    480
ataaataaaa ccaactaatc gagatatcac atatgcggtc cggatccagt ttaaacagta    540
gctttggact tcttcgccag aggtttggtc aagtctccaa tcaaggttgt cggcttgtct    600
accttgccag aaatttacga aaagatggaa aagggtcaaa tcgttggtag atacgttgtt    660
gacacttcta aataagcgaa tttcttatga tttatgattt ttattattaa ataagttata    720
aaaaaaataa gtgtatacaa attttaaagt gactcttagg ttttaaaacg aaaattcttg    780
ttcttgagta actctttcct gtaggtcagg ttgctttctc aggtatagca tgaggtcgct    840
cttattgacc acacctctac cggcatgccg agcaaatgcc tgcaaatcgc tccccatttc    900
acccaattgt agatatgcta actccagcaa tgagttgatg aatctcggtg tgtattttat    960
gtcctcagaa gacaacacct gttgtaatcg ttcttccaca cggatcgcgg ccgcttgatc   1020
ctctacgccg gacgcatcgt ggccggcatc accggcgcca caggtgcggt tgctggcgcc   1080
tatatcgccg acatcaccga tggggaagat cgggctcgcc acttcgggct catgagcgct   1140
tgtttcggcg tgggtatggt ggcaggcccc gtggccgggg gactgttggg cgccatctcc   1200
ttgcatgcac cattccttgc ggcggcggtg ctcaacggcc tcaacctact actgggctgc   1260
ttcctaatgc aggagtcgca taagggagag cgtcgaccga tgcccttgag agccttcaac   1320
ccagtcagct ccttccggtg ggcgcggggc atgactatcg tcgccgcact tatgactgtc   1380
ttctttatca tgcaactcgt aggacaggtg ccggcagcgc tctgggtcat tttcggcgag   1440
gaccgctttc gctggagcgc gacgatgatc ggcctgtcgc ttgcggtatt cggaatcttg   1500
cacgccctcg ctcaagcctt cgtcactggt cccgccacca aacgtttcgg cgagaagcag   1560
gccattatcg ccggcatggc ggccgacgcg ctgggctacg tcttgctggc gttcgcgacg   1620
cgaggctgga tggccttccc cattatgatt cttctcgctt ccggcggcat cgggatgccc   1680
gcgttgcagg ccatgctgtc caggcaggta gatgacgacc atcagggaca gcttcaagga   1740
tcgctcgcgg ctcttaccag cctaacttcg atcactggac cgctgatcgt cacggcgatt   1800
tatgccgcct cggcgagcac atggaacggg ttggcatgga ttgtaggcgc cgccctatac   1860
cttgtctgcc tccccgcgtt gcgtcgcggt gcatggagcc gggccacctc gacctgaatg   1920
gaagccggcg gcacctcgct aacggattca ccactccaag aattggagcc aatcaattct   1980
tgcggagaac tgtgaatgcg caaaccaacc cttggcagaa catatccatc gcgtccgcca   2040
tctccagcag ccgcacgcgg cgcatctcgg gcagcgttgg gtcctggcca cgggtgcgca   2100
tgatcgtgct cctgtcgttg aggacccggc taggctggcg gggttgcctt actggttagc   2160
agaatgaatc accgatacgc gagcgaacgt gaagcgactg ctgctgcaaa acgtctgcga   2220
cctgagcaac aacatgaatg gtcttcggtt tccgtgtttc gtaaagtctg gaaacgcgga   2280
agtcagcgcc ctgcaccatt atgttccgga tctgcatcgc aggatgctgc tggctaccct   2340
gtggaacacc tacatctgta ttaacgaagc gctggcattg accctgagtg atttttctct   2400
```

-continued

```
ggtcccgccg catccatacc gccagttgtt taccctcaca acgttccagt aaccgggcat   2460
gttcatcatc agtaacccgt atcgtgagca tcctctctcg tttcatcggt atcattaccc   2520
ccatgaacag aaattccccc ttacacggag gcatcaagtg accaaacagg aaaaaaccgc   2580
ccttaacatg gcccgcttta tcagaagcca gacattaacg cttctggaga aactcaacga   2640
gctggacgcg gatgaacagg cagacatctg tgaatcgctt cacgaccacg ctgatgagct   2700
ttaccgcagc tgcctcgcgc gtttcggtga tgacggtgaa aacctctgac acatgcagct   2760
cccggagacg gtcacagctt gtctgtaagc ggatgccggg agcagacaag cccgtcaggg   2820
cgcgtcagcg ggtgttggcg ggtgtcgggg cgcagccatg acccagtcac gtagcgatag   2880
cggagtgtat actggcttaa ctatgcggca tcagagcaga ttgtactgag agtgcacgat   2940
atccggtgtg aaataccgca cagatgcgta aggagaaaat accgcatcag gcgctcttcc   3000
gcttcctcgc tcactgactc gctgcgctcg gtcgttcggc tgcggcgagc ggtatcagct   3060
cactcaaagg cggtaatacg gttatccaca gaatcagggg ataacgcagg aaagaacatg   3120
tgagcaaaag gccagcaaaa ggccaggaac cgtaaaaagg ccgcgttgct ggcgtttttc   3180
cataggctcc gcccccctga cgagcatcac aaaaatcgac gctcaagtca gaggtggcga   3240
aacccgacag gactataaag ataccaggcg tttccccctg gaagctccct cgtgcgctct   3300
cctgttccga ccctgccgct taccggatac ctgtccgcct ttctcccttc gggaagcgtg   3360
gcgctttctc aatgctcacg ctgtaggtat ctcagttcgg tgtaggtcgt tcgctccaag   3420
ctgggctgtg tgcacgaacc ccccgttcag cccgaccgct gcgccttatc cggtaactat   3480
cgtcttgagt ccaacccggt aagacacgac ttatcgccac tggcagcagc cactggtaac   3540
aggattagca gagcgaggta tgtaggcggt gctacagagt tcttgaagtg gtggcctaac   3600
tacggctaca ctagaaggac agtatttggt atctgcgctc tgctgaagcc agttaccttc   3660
ggaaaaagag ttggtagctc ttgatccggc aaacaaacca ccgctggtag cggtggtttt   3720
tttgtttgca agcagcagat tacgcgcaga aaaaaaggat ctcaagaaga tcctttgatc   3780
ttttctacgg ggtctgacgc tcagtggaac gaaaactcac gttaagggat tttggtcatg   3840
agattatcaa aaaggatctt cacctagatc cttttaaatt aaaaatgaag ttttaaatca   3900
atctaaagta tatatgagta aacttggtct gacagttacc aatgcttaat cagtgaggca   3960
cctatctcag cgatctgtct atttcgttca tccatagttg cctgactccc cgtcgtgtag   4020
ataactacga tacgggaggg cttaccatct ggccccagtg ctgcaatgat accgcgagac   4080
ccacgctcac cggctccaga tttatcagca ataaaccagc cagccggaag ggccgagcgc   4140
agaagtggtc ctgcaacttt atccgcctcc atccagtcta ttaattgttg ccgggaagct   4200
agagtaagta gttcgccagt taatagtttg cgcaacgttg ttgccattgc tgcaggcatc   4260
gtggtgtcac gctcgtcgtt tggtatggct tcattcagct ccggttccca acgatcaagg   4320
cgagttacat gatcccccat gttgtgcaaa aaagcggtta gctccttcgg tcctccgatc   4380
gttgtcagaa gtaagttggc cgcagtgtta tcactcatgg ttatggcagc actgcataat   4440
tctcttactg tcatgccatc cgtaagatgc ttttctgtga ctggtgagta ctcaaccaag   4500
tcattctgag aatagtgtat gcggcgaccg agttgctctt gcccggcgtc aacacgggat   4560
aataccgcgc cacatagcag aactttaaaa gtgctcatca ttggaaaacg ttcttcgggg   4620
cgaaaactct caaggatctt accgctgttg agatccagtt cgatgtaacc cactcgtgca   4680
cccaactgat cttcagcatc ttttactttc accagcgttt ctgggtgagc aaaaacagga   4740
aggcaaaatg ccgcaaaaaa gggaataagg gcgacacgga aatgttgaat actcatactc   4800
```

-continued

```
ttcctttttc aatattattg aagcatttat cagggttatt gtctcatgag cggatacata   4860
tttgaatgta tttagaaaaa taaacaaata ggggttccgc gcacatttcc ccgaaaagtg   4920
ccacctgacg tctaagaaac cattattatc atgacattaa cctataaaaa taggcgtatc   4980
acgaggccct ttcgtcttca agaattccac ggactataga ctatactagt atactccgtc   5040
tactgtacga tacacttccg ctcaggtcct tgtcctttaa cgaggcctta ccactctttt   5100
gttactctat tgatccagct cagcaaaggc agtgtgatct aagattctat cttcgcgatg   5160
tagtaaaact agctagaccg agaaagagac tagaaatgca aaaggcactt ctacaatggc   5220
tgccatcatt attatccgat gtgacgctgc agaagcagaa atacacgcgg tcagtgaagc   5280
tattccgcta ttgaataacc tcagtcacct tgtgcaagaa cttaacaaga aaccaattat   5340
taaaggctta cttactgata gtagatcaac gatcagtata attaagtcta caaatgaaga   5400
gaaatttaga aacagatttt ttggcacaaa ggcaatgaga cttagagatg aagtatcagg   5460
taataattta tacgtatact acatcgagac caagaagaac attgctgatg tgatgacaaa   5520
acctcttccg ataaaaacat ttaaactatt aactaacaaa tggattcatt agatctatta   5580
cattatgggt ggtatgttgg aataaaaatc aactatcatc tactaactag tatttacgtt   5640
actagtatat tatcatatac ggtgttagaa gatgacgcaa atgatgagaa atagtcatct   5700
aaattagtgg aagctgaaac gcaaggattg ataatgtaat aggatcaatg aatattaaca   5760
tataaaatga tgataataat atttatagaa ttgtgtagaa ttgcagattc ccttttatgg   5820
attcctaaat cctcgaggag aacttctagt atatctacat acctaatatt attgccttat   5880
taaaaatgga atcccaacaa ttacatcaaa atccacattc tcttcaaaat caattgtcct   5940
gtacttcctt gttcatgtgt gttcaaaaac gttatattta taggataatt atactctatt   6000
tctcaacaag taattggttg tttggccgag cggtctaagg cgcctgattc aagaaatatc   6060
ttgaccgcag ttaactgtgg gaatactcag gtatcgtaag atgcaagagt tcgaatctct   6120
tagcaaccat tattttttc ctcaacataa cgagaacaca caggggcgct atcgcacaga   6180
atcaaattcg atgactggaa attttttgtt aatttcagag gtcgcctgac gcatatacct   6240
ttttcaactg aaaaattggg agaaaaagga aaggtgagag ccgcggaacc ggcttttcat   6300
atagaataga gaagcgttca tgactaaatg cttgcatcac aatacttgaa gttgacaata   6360
ttatttaagg acctattgtt ttttccaata ggtggttagc aatcgtctta ctttctaact   6420
tttcttacct tttacatttc agcaatatat atatatatat ttcaaggata taccattcta   6480
atgtctgccc ctaagaagat cgtcgttttg ccaggtgacc acgttggtca agaaatcaca   6540
gccgaagcca ttaaggttct taaagctatt tctgatgttc gttccaatgt caagttcgat   6600
ttcgaaaatc atttaattgg tggtgctgct atcgatgcta caggtgtccc acttccagat   6660
gaggcgctgg aagcctccaa gaaggttgat gccgttttgt taggtgctgt gggtggtcct   6720
aaatggggta ccggtagtgt tagacctgaa caaggtttac taaaaatccg taaagaactt   6780
caattgtacg ccaacttaag accatgtaac tttgcatccg actctctttt agacttatct   6840
ccaatcaagc cacaatttgc taaaggtact gacttcgttg ttgtcagaga attagtggga   6900
ggtatttact ttggtaagag aaaggaagac gatggtgatg gtgtcgcttg ggatagtgaa   6960
caatacaccg ttccagaagt gcaaagaatc acaagaatgg ccgctttcat ggccctacaa   7020
catgagccac cattgcctat ttggtccttg gataaagcta atgttttggc ctcttcaaga   7080
ttatggagaa aaactgtgga ggaaaccatc aagaacgaat tccctacatt gaaggttcaa   7140
```

-continued

```
catcaattga ttgattctgc cgccatgatc ctagttaaga acccaaccca cctaaatggt   7200
attataatca ccagcaacat gtttggtgat atcatctccg atgaagcctc cgttatccca   7260
ggttccttgg gtttgttgcc atctgcgtcc ttggcctctt tgccagacaa gaacaccgca   7320
tttggtttgt acgaaccatg ccacggttct gctccagatt tgccaaagaa taaggtcaac   7380
cctatcgcca ctatcttgtc tgctgcaatg atgttgaaat tgtcattgaa cttgcctgaa   7440
gaaggtaagg ccattgaaga tgcagttaaa aaggttttgg atgcaggtat cagaactggt   7500
gatttaggtg gttccaacag taccacggaa gtcggtgatg ctgtcgccga agaagttaag   7560
aaaatccttg cttaaaaaga ttctcttttt ttatgatatt tgtacataaa ctttataaat   7620
gaaattcata atagaaacga cacgaaatta caaaatggaa tatgttcata gggtagacga   7680
aactatatac gcaatctaca tacatttatc aagaaggaga aaaaggagga tgtaaaggaa   7740
tacaggtaag caaattgata ctaatggctc aacgtgataa ggaaaaagaa ttgcacttta   7800
acattaatat tgacaaggag gagggcacca cacaaaaagt taggtgtaac agaaaatcat   7860
gaaactatga ttcctaattt atatattgga ggattttctc taaaaaaaaa aaaatacaac   7920
aaataaaaaa cactcaatga cctgaccatt tgatggagtt taagtcaata ccttcttgaa   7980
ccatttccca taatggtgaa agttccctca agaattttac tctgtcagaa acggccttaa   8040
cgacgtagtc gacctcctct tcagtactaa atctaccaat accaaatctg atggaagaat   8100
gggctaatgc atcatcctta cccagcgcat gtaaaacata agaaggttct agggaagcag   8160
atgtacaggc tgaacccgag gataatgcga tatcccttag tgccatcaat aaagattctc   8220
cttccacgta ggcgaaagaa acgttaacac accctggata acgatgatct ggagatccgt   8280
tcaacgtggt atgttcagcg gataatagac ctttgactaa tttatcggat agtcttttga   8340
tgtgagcttg gtcgttgtca aattctttct tcatcaatct cgcagcttca ccaaatcccg   8400
ctaccaatgg gggggccaaa gtaccagatc tcaatcctct ctcttggcca ccaccggata   8460
gtaaaggttc taatctaact cttggtctcc ttcttacata gatggcacct attccctttg   8520
gaccgtaaat cttgtgagaa gaaattgata gtaaatcaat gttcatttca ttgacatcaa   8580
tgtgaatctt accataggct tgtgcggcgt cagtatgaaa gtagatctta ttctttctac   8640
aaattgcacc aatttcttta ataggttgaa tgacaccgat ttcattattg acagccatca   8700
cagagacgag acaggtatct ggtctaatgg catcttccaa ttccttcaaa tcgataagac   8760
cttgatcgtc cacatttagg aaagtgactt caaatccctc cttcatcatg gcccgtgcgg   8820
cttccaagac acacttgtgt tccgttctag tggtgatgat gtgtttctta gtcttcttat   8880
aaaatcttgg gacaccctta agaaccatat tattagattc ggtcgctccc gaagtgaata   8940
ttatttcctt ggggtcggca ttgatcatct ttgctacgta agctctagca ttttccacag   9000
cagtatttgt ttcccaaccg taagagtgag tgttggaatg aggattacca taaagtcccg   9060
tataaaactt caacatcgta tccaaaaccc tagggtctgt tggtgtagtg gcttgcatgt   9120
caagatatat gggacgagta ccaaaacctg tgttttcttg ataagcatgg ctcattgcag   9180
tgctaccaga agctactaca gcatctgggg tggtaccgga tgcactcgca cgggcactag   9240
cctgtgcctt tgcagcagcc tgaatatcgg tatgcgtttc cagagagaag ttgtcgtcta   9300
acttcacgcc tgctgcagtc tcaatgatat tcgaatacgc tttgaggaga tacagcctaa   9360
tatccgacaa actgttttac agatttacga tcgtacttgt tacccatcat tgaattttga   9420
acatccgaac ctgggagttt tccctgaaac agatagtata tttgaacctg tataataata   9480
tatagtctag cgctttacgg aagacaatgt atgtatttcg gttcctggag aaactattgc   9540
```

```
atctattgca taggtaatct tgcacgtcgc atccccggtt cattttctgc gtttccatct   9600
tgcacttcaa tagcatatct ttgttaacga agcatctgtg cttcattttg tagaacaaaa   9660
atgcaacgcg agagcgctaa tttttcaaac aaagaatctg agctgcattt ttacagaaca   9720
gaaatgcaac gcgaaagcgc tattttacca acgaagaatc tgtgcttcat tttgtaaaa    9780
caaaaatgca acgcgagagc gctaattttt caaacaaaga atctgagctg catttttaca   9840
gaacagaaat gcaacgcgag agcgctattt taccaacaaa gaatctatac ttcttttttg   9900
ttctacaaaa atgcatcccg agagcgctat ttttctaaca aagcatctta gattactttt   9960
tttctccttt gtgcgctcta taatgcagtc tcttgataac tttttgcact gtaggtccgt  10020
taaggttaga agaaggctac tttggtgtct attttctctt ccataaaaaa agcctgactc  10080
cacttcccgc gtttactgat tactagcgaa gctgcgggtg catttttca agataaaggc   10140
atccccgatt atattctata ccgatgtgga ttgcgcatac tttgtgaaca gaaagtgata  10200
gcgttgatga ttcttcattg gtcagaaaat tatgaacggt ttcttctatt ttgtctctat  10260
atactacgta taggaaatgt ttacattttc gtattgtttt cgattcactc tatgaatagt  10320
tcttactaca attttttgt ctaaagagta atactagaga taaacataaa aaatgtagag   10380
gtcgagttta gatgcaagtt caaggagcga aaggtggatg ggtaggttat atagggatat  10440
agcacagaga tatatagcaa agagatactt ttgagcaatg tttgtggaag cggtattcgc  10500
aatattttag tagctcgtta cagtccggtg cgtttttggt tttttgaaag tgcgtcttca  10560
gagcgctttt ggttttcaaa agcgctctga agttcctata ctttctagag aataggaact  10620
tcggaatagg aacttcaaag cgtttccgaa aacgagcgct tccgaaaatg caacgcgagc  10680
tgcgcacata cagctcactg ttcacgtcgc acctatatct gcgtgttgcc tgtatatata  10740
tatacatgag aagaacggca tagtgcgtgt ttatgcttaa atgcgtactt atatgcgtct  10800
atttatgtag gatgaaaggt agtctagtac ctcctgtgat attatcccat tccatgcggg  10860
gtatcgtatg cttccttcag cactaccctt tagctgttct atatgctgcc actcctcaat  10920
tggattagtc tcatccttca atgctatcat ttcctttgat attcgatcct aggcatagta  10980
ccgagaaact agtgcgaagt agtgatcagg tattgctgtt atctgatgag tatacgttgt  11040
cctggccacg gcagaagcac gcttatcgct ccaatttccc acaacattag tcaactccgt  11100
taggcccttc attgaaagaa atgaggtcat caaatgtctt ccaatgtgag attttgggcc  11160
attttttata gcaaagattg aataaggcgc atttttcttc a                      11201
```

<210> SEQ ID NO 26
<211> LENGTH: 11204
<212> TYPE: DNA
<213> ORGANISM: Saccharomyces cerevisiae

<400> SEQUENCE: 26

```
aagcttcgcg gccgcggagg tctgcttcac gagcgcggtg tgcgcctagt attgccccga     60
cggtccgggt gcctatccct agatttcgtc gtgccccgac ccaaatagtt aaacgtgtgg    120
tttatgggtg caccagggct ttatcgtgtt ttatatcgat ggcgatttgt gcctccagtg    180
tattttttgta tatccaatta aggtttctta cctaatttta tttttatcat ctttagttaa   240
tgctggtttg ctctgtttct gctgctttct gtgcggttct cctcttctct tgtttcttcg    300
tgttgtcccc catcgccgat gggcttatat ggcgtatata tatagagcga gtttttacgt    360
cgaagatcat ctcagtttgc ttgatagcct ttctacttta ttactttcgt ttttaacctc    420
```

-continued

```
attatacttt agttttcttt gatcggtttt tttctctgta tacttaaaag ttcaaatcaa    480
agaaacatac aaaactacgt ttatatcaat tacatatgcg gtccggatcc agtttaaaca    540
gtagctttgg acttcttcgc cagaggtttg gtcaagtctc caatcaaggt tgtcggcttg    600
tctaccttgc cagaaattta cgaaaagatg gaaaagggtc aaatcgttgg tagatacgtt    660
gttgacactt ctaaataagc gaatttctta tgatttatga tttttattat taaataagtt    720
ataaaaaaaa taagtgtata caaattttaa agtgactctt aggttttaaa acgaaaattc    780
ttgttcttga gtaactcttt cctgtaggtc aggttgcttt ctcaggtata gcatgaggtc    840
gctcttattg accacacctc taccggcatg ccgagcaaat gcctgcaaat cgctccccat    900
ttcacccaat tgtagatatg ctaactccag caatgagttg atgaatctcg gtgtgtattt    960
tatgtcctca gaagacaaca cctgttgtaa tcgttcttcc acacggatcg cggccgcttg   1020
atcctctacg ccggacgcat cgtggccggc atcaccggcg ccacaggtgc ggttgctggc   1080
gcctatatcg ccgacatcac cgatggggaa gatcgggctc gccacttcgg gctcatgagc   1140
gcttgtttcg gcgtgggtat ggtggcaggc cccgtggccg ggggactgtt gggcgccatc   1200
tccttgcatg caccattcct tgcggcggcg gtgctcaacg gcctcaacct actactgggc   1260
tgcttcctaa tgcaggagtc gcataaggga gagcgtcgac cgatgccctt gagagccttc   1320
aacccagtca gctccttccg gtgggcgcgg ggcatgacta tcgtcgccgc acttatgact   1380
gtcttcttta tcatgcaact cgtaggacag gtgccggcag cgctctgggt cattttcggc   1440
gaggaccgct ttcgctggag cgcgacgatg atcggcctgt cgcttgcggt attcggaatc   1500
ttgcacgccc tcgctcaagc cttcgtcact ggtcccgcca ccaaacgttt cggcgagaag   1560
caggccatta tcgccggcat ggcggccgac gcgctgggct acgtcttgct ggcgttcgcg   1620
acgcgaggct ggatggcctt ccccattatg attcttctcg cttccggcgg catcgggatg   1680
cccgcgttgc aggccatgct gtccaggcag gtagatgacg accatcaggg acagcttcaa   1740
ggatcgctcg cggctcttac cagcctaact tcgatcactg gaccgctgat cgtcacggcg   1800
atttatgccg cctcggcgag cacatggaac gggttggcat ggattgtagg cgccgcccta   1860
taccttgtct gcctccccgc gttgcgtcgc ggtgcatgga gccgggccac ctcgacctga   1920
atggaagccg gcggcacctc gctaacggat tcaccactcc aagaattgga gccaatcaat   1980
tcttgcggag aactgtgaat gcgcaaacca acccttggca gaacatatcc atcgcgtccg   2040
ccatctccag cagccgcacg cggcgcatct cgggcagcgt tgggtcctgg ccacgggtgc   2100
gcatgatcgt gctcctgtcg ttgaggaccc ggctaggctg gcggggttgc cttactggtt   2160
agcagaatga atcaccgata cgcgagcgaa cgtgaagcga ctgctgctgc aaaacgtctg   2220
cgacctgagc aacaacatga atggtcttcg gtttccgtgt ttcgtaaagt ctggaaacgc   2280
ggaagtcagc gccctgcacc attatgttcc ggatctgcat cgcaggatgc tgctggctac   2340
cctgtggaac acctacatct gtattaacga agcgctggca ttgaccctga gtgatttttc   2400
tctggtcccg ccgcatccat accgccagtt gtttaccctc acaacgttcc agtaaccggg   2460
catgttcatc atcagtaacc cgtatcgtga gcatcctctc tcgtttcatc ggtatcatta   2520
cccccatgaa cagaaattcc cccttacacg gaggcatcaa gtgaccaaac aggaaaaaac   2580
cgcccttaac atggcccgct ttatcagaag ccagacatta acgcttctgg agaaactcaa   2640
cgagctggac gcggatgaac aggcagacat ctgtgaatcg cttcacgacc acgctgatga   2700
gctttaccgc agctgcctcg cgcgtttcgg tgatgacggt gaaaacctct gacacatgca   2760
gctcccggag acggtcacag cttgtctgta agcggatgcc gggagcagac aagcccgtca   2820
```

-continued

```
gggcgcgtca gcgggtgttg gcgggtgtcg gggcgcagcc atgacccagt cacgtagcga   2880
tagcggagtg tatactggct taactatgcg gcatcagagc agattgtact gagagtgcac   2940
gatatccggt gtgaaatacc gcacagatgc gtaaggagaa aataccgcat caggcgctct   3000
tccgcttcct cgctcactga ctcgctgcgc tcggtcgttc ggctgcggcg agcggtatca   3060
gctcactcaa aggcggtaat acggttatcc acagaatcag gggataacgc aggaaagaac   3120
atgtgagcaa aaggccagca aaaggccagg aaccgtaaaa aggccgcgtt gctggcgttt   3180
ttccataggc tccgcccccc tgacgagcat cacaaaaatc gacgctcaag tcagaggtgg   3240
cgaaacccga caggactata aagataccag gcgtttcccc ctggaagctc cctcgtgcgc   3300
tctcctgttc cgaccctgcc gcttaccgga tacctgtccg cctttctccc ttcgggaagc   3360
gtggcgcttt ctcaatgctc acgctgtagg tatctcagtt cggtgtaggt cgttcgctcc   3420
aagctgggct gtgtgcacga accccccgtt cagcccgacc gctgcgcctt atccggtaac   3480
tatcgtcttg agtccaaccc ggtaagacac gacttatcgc cactggcagc agccactggt   3540
aacaggatta gcagagcgag gtatgtaggc ggtgctacag agttcttgaa gtggtggcct   3600
aactacggct acactagaag gacagtattt ggtatctgcg ctctgctgaa gccagttacc   3660
ttcggaaaaa gagttggtag ctcttgatcc ggcaaacaaa ccaccgctgg tagcggtggt   3720
tttttgttt gcaagcagca gattacgcgc agaaaaaaag gatctcaaga agatcctttg   3780
atcttttcta cggggtctga cgctcagtgg aacgaaaact cacgttaagg gattttggtc   3840
atgagattat caaaaaggat cttcacctag atccttttaa attaaaaatg aagttttaaa   3900
tcaatctaaa gtatatatga gtaaacttgg tctgacagtt accaatgctt aatcagtgag   3960
gcacctatct cagcgatctg tctatttcgt tcatccatag ttgcctgact ccccgtcgtg   4020
tagataacta cgatacggga gggcttacca tctggcccca gtgctgcaat gataccgcga   4080
gacccacgct caccggctcc agatttatca gcaataaacc agccagccgg aagggccgag   4140
cgcagaagtg gtcctgcaac tttatccgcc tccatccagt ctattaattg ttgccgggaa   4200
gctagagtaa gtagttcgcc agttaatagt ttgcgcaacg ttgttgccat tgctgcaggc   4260
atcgtggtgt cacgctcgtc gtttggtatg gcttcattca gctccggttc ccaacgatca   4320
aggcgagtta catgatcccc catgttgtgc aaaaaagcgg ttagctcctt cggtcctccg   4380
atcgttgtca gaagtaagtt ggccgcagtg ttatcactca tggttatggc agcactgcat   4440
aattctctta ctgtcatgcc atccgtaaga tgcttttctg tgactggtga gtactcaacc   4500
aagtcattct gagaatagtg tatgcggcga ccgagttgct cttgcccggc gtcaacacgg   4560
gataataccg cgccacatag cagaacttta aaagtgctca tcattggaaa acgttcttcg   4620
gggcgaaaac tctcaaggat cttaccgctg ttgagatcca gttcgatgta acccactcgt   4680
gcacccaact gatcttcagc atcttttact ttcaccagcg tttctgggtg agcaaaaaca   4740
ggaaggcaaa atgccgcaaa aaagggaata agggcgacac ggaaatgttg aatactcata   4800
ctcttccttt ttcaatatta ttgaagcatt tatcagggtt attgtctcat gagcggatac   4860
atatttgaat gtatttagaa aaataaacaa ataggggttc cgcgcacatt tccccgaaaa   4920
gtgccacctg acgtctaaga aaccattatt atcatgacat taacctataa aaataggcgt   4980
atcacgaggc cctttcgtct tcaagaattc cacggactat agactatact agtatactcc   5040
gtctactgta cgatacactt ccgctcaggt ccttgtcctt taacgaggcc ttaccactct   5100
tttgttactc tattgatcca gctcagcaaa ggcagtgtga tctaagattc tatcttcgcg   5160
```

-continued

```
atgtagtaaa actagctaga ccgagaaaga gactagaaat gcaaaaggca cttctacaat   5220
ggctgccatc attattatcc gatgtgacgc tgcagaagca gaaatacacg cggtcagtga   5280
agctattccg ctattgaata acctcagtca ccttgtgcaa gaacttaaca agaaaccaat   5340
tattaaaggc ttacttactg atagtagatc aacgatcagt ataattaagt ctacaaatga   5400
agagaaattt agaaacagat tttttggcac aaaggcaatg agacttagag atgaagtatc   5460
aggtaataat ttatacgtat actacatcga gaccaagaag aacattgctg atgtgatgac   5520
aaaacctctt ccgataaaaa catttaaact attaactaac aaatggattc attagatcta   5580
ttacattatg ggtggtatgt tggaataaaa atcaactatc atctactaac tagtatttac   5640
gttactagta tattatcata tacggtgtta gaagatgacg caaatgatga gaaatagtca   5700
tctaaattag tggaagctga aacgcaagga ttgataatgt aataggatca atgaatatta   5760
acatataaaa tgatgataat aatatttata gaattgtgta gaattgcaga ttccctttta   5820
tggattccta aatcctcgag gagaacttct agtatatcta catacctaat attattgcct   5880
tattaaaaat ggaatcccaa caattacatc aaaatccaca ttctcttcaa aatcaattgt   5940
cctgtacttc cttgttcatg tgtgttcaaa aacgttatat ttataggata attatactct   6000
atttctcaac aagtaattgg ttgtttggcc gagcggtcta aggcgcctga ttcaagaaat   6060
atcttgaccg cagttaactg tgggaatact caggtatcgt aagatgcaag agttcgaatc   6120
tcttagcaac cattattttt ttcctcaaca taacgagaac acacaggggc gctatcgcac   6180
agaatcaaat tcgatgactg gaaatttttt gttaatttca gaggtcgcct gacgcatata   6240
ccttttcaa ctgaaaaatt gggagaaaaa ggaaaggtga gagccgcgga accggctttt   6300
catatagaat agagaagcgt tcatgactaa atgcttgcat cacaatactt gaagttgaca   6360
atattattta aggacctatt gttttttcca ataggtggtt agcaatcgtc ttactttcta   6420
acttttctta ccttttacat ttcagcaata tatatatata tatttcaagg atataccatt   6480
ctaatgtctg cccctaagaa gatcgtcgtt ttgccaggtg accacgttgg tcaagaaatc   6540
acagccgaag ccattaaggt tcttaaagct atttctgatg ttcgttccaa tgtcaagttc   6600
gatttcgaaa atcatttaat tggtggtgct gctatcgatg ctacaggtgt cccacttcca   6660
gatgaggcgc tggaagcctc caagaaggtt gatgccgttt tgttaggtgc tgtgggtggt   6720
cctaaatggg gtaccggtag tgttagacct gaacaaggtt tactaaaaat ccgtaaagaa   6780
cttcaattgt acgccaactt aagaccatgt aactttgcat ccgactctct tttagactta   6840
tctccaatca agccacaatt tgctaaaggt actgacttcg ttgttgtcag agaattagtg   6900
ggaggtattt actttggtaa gagaaaggaa gacgatggtg atggtgtcgc ttgggatagt   6960
gaacaataca ccgttccaga agtgcaaaga atcacaagaa tggccgcttt catggcccta   7020
caacatgagc caccattgcc tatttggtcc ttggataaag ctaatgtttt ggcctcttca   7080
agattatgga gaaaaactgt ggaggaaacc atcaagaacg aattccctac attgaaggtt   7140
caacatcaat tgattgattc tgccgccatg atcctagtta agaacccaac ccacctaaat   7200
ggtattataa tcaccagcaa catgtttggt gatatcatct ccgatgaagc ctccgttatc   7260
ccaggttcct tgggtttgtt gccatctgcg tccttggcct ctttgccaga caagaacacc   7320
gcatttggtt tgtacgaacc atgccacggt tctgctccag atttgccaaa gaataaggtc   7380
aaccctatcg ccactatctt gtctgctgca atgatgttga aattgtcatt gaacttgcct   7440
gaagaaggta aggccattga agatgcagtt aaaaaggttt tggatgcagg tatcagaact   7500
ggtgatttag gtggttccaa cagtaccacg gaagtcggtg atgctgtcgc cgaagaagtt   7560
```

```
aagaaaatcc ttgcttaaaa agattctctt tttttatgat atttgtacat aaactttata   7620
aatgaaattc ataatagaaa cgacacgaaa ttacaaaatg gaatatgttc atagggtaga   7680
cgaaactata tacgcaatct acatacattt atcaagaagg agaaaaagga ggatgtaaag   7740
gaatacaggt aagcaaattg atactaatgg ctcaacgtga taaggaaaaa gaattgcact   7800
ttaacattaa tattgacaag gaggagggca ccacacaaaa agttaggtgt aacagaaaat   7860
catgaaacta tgattcctaa tttatatatt ggaggatttt ctctaaaaaa aaaaaaatac   7920
aacaaataaa aaacactcaa tgacctgacc atttgatgga gtttaagtca ataccttctt   7980
gaaccatttc ccataatggt gaaagttccc tcaagaattt tactctgtca gaaacggcct   8040
taacgacgta gtcgacctcc tcttcagtac taaatctacc aataccaaat ctgatggaag   8100
aatgggctaa tgcatcatcc ttacccagcg catgtaaaac ataagaaggt tctagggaag   8160
cagatgtaca ggctgaaccc gaggataatg cgatatccct tagtgccatc aataaagatt   8220
ctccttccac gtaggcgaaa gaaacgttaa cacaccctgg ataacgatga tctggagatc   8280
cgttcaacgt ggtatgttca gcggataata gacctttgac taatttatcg gatagtcttt   8340
tgatgtgagc ttggtcgttg tcaaattctt tcttcatcaa tctcgcagct tcaccaaatc   8400
ccgctaccaa tggggggcc aaagtaccag atctcaatcc tctctcttgg ccaccaccgg   8460
atagtaaagg ttctaatcta actcttggtc tccttcttac atagatggca cctattccct   8520
ttggaccgta aatcttgtga gaagaaattg atagtaaatc aatgttcatt tcattgacat   8580
caatgtgaat cttaccatag gcttgtgcgg cgtcagtatg aaagtagatc ttattctttc   8640
tacaaattgc accaatttct ttaataggtt gaatgacacc gatttcatta ttgacagcca   8700
tcacagagac gagacaggta tctggtctaa tggcatcttc caattccttc aaatcgataa   8760
gaccttgatc gtccacattt aggaaagtga cttcaaatcc ctccttcatc atggcccgtg   8820
cggcttccaa gacacacttg tgttccgttc tagtggtgat gatgtgtttc ttagtcttct   8880
tataaaatct tgggacaccc ttaagaacca tattattaga ttcggtcgct cccgaagtga   8940
atattatttc cttggggtcg gcattgatca tctttgctac gtaagctcta gcattttcca   9000
cagcagtatt tgtttcccaa ccgtaagagt gagtgttgga atgaggatta ccataaagtc   9060
ccgtataaaa cttcaacatc gtatccaaaa ccctagggtc tgttggtgta gtggcttgca   9120
tgtcaagata tatgggacga gtaccaaaac ctgtgttttc ttgataagca tggctcattg   9180
cagtgctacc agaagctact acagcatctg ggtggtaccc ggatgcactc gcacgggcac   9240
tagcctgtgc ctttgcagca gcctgaatat cggtatgcgt ttccagagag aagttgtcgt   9300
ctaacttcac gcctgctgca gtctcaatga tattcgaata cgctttgagg agatacagcc   9360
taatatccga caaactgttt tacagattta cgatcgtact tgttacccat cattgaattt   9420
tgaacatccg aacctgggag ttttccctga aacagatagt atatttgaac ctgtataata   9480
atatatagtc tagcgcttta cggaagacaa tgtatgtatt tcggttcctg gagaaactat   9540
tgcatctatt gcataggtaa tcttgcacgt cgcatccccg gttcattttc tgcgtttcca   9600
tcttgcactt caatagcata tctttgttaa cgaagcatct gtgcttcatt ttgtagaaca   9660
aaaatgcaac gcgagagcgc taatttttca aacaaagaat ctgagctgca tttttacaga   9720
acagaaatgc aacgcgaaag cgctatttta ccaacgaaga atctgtgctt catttttgta   9780
aaacaaaaat gcaacgcgag agcgctaatt tttcaaacaa agaatctgag ctgcattttt   9840
acagaacaga aatgcaacgc gagagcgcta ttttaccaac aaagaatcta tacttctttt   9900
```

-continued

```
ttgttctaca aaaatgcatc ccgagagcgc tatttttcta acaaagcatc ttagattact   9960

tttttctcc tttgtgcgct ctataatgca gtctcttgat aactttttgc actgtaggtc  10020

cgttaaggtt agaagaaggc tactttggtg tctattttct cttccataaa aaaagcctga  10080

ctccacttcc cgcgtttact gattactagc gaagctgcgg gtgcattttt tcaagataaa  10140

ggcatccccg attatattct ataccgatgt ggattgcgca tactttgtga acagaaagtg  10200

atagcgttga tgattcttca ttggtcagaa aattatgaac ggtttcttct attttgtctc  10260

tatatactac gtataggaaa tgtttacatt ttcgtattgt tttcgattca ctctatgaat  10320

agttcttact acaatttttt tgtctaaaga gtaatactag agataaacat aaaaaatgta  10380

gaggtcgagt ttagatgcaa gttcaaggag cgaaaggtgg atgggtaggt tatataggga  10440

tatagcacag agatatatag caaagagata cttttgagca atgtttgtgg aagcggtatt  10500

cgcaatattt tagtagctcg ttacagtccg gtgcgttttt ggttttttga aagtgcgtct  10560

tcagagcgct tttggttttc aaaagcgctc tgaagttcct atactttcta gagaatagga  10620

acttcggaat aggaacttca aagcgtttcc gaaaacgagc gcttccgaaa atgcaacgcg  10680

agctgcgcac atacagctca ctgttcacgt cgcacctata tctgcgtgtt gcctgtatat  10740

atatatacat gagaagaacg gcatagtgcg tgtttatgct taaatgcgta cttatatgcg  10800

tctatttatg taggatgaaa ggtagtctag tacctcctgt gatattatcc cattccatgc  10860

ggggtatcgt atgcttcctt cagcactacc ctttagctgt tctatatgct gccactcctc  10920

aattggatta gtctcatcct tcaatgctat catttccttt gatattcgat cctaggcata  10980

gtaccgagaa actagtgcga agtagtgatc aggtattgct gttatctgat gagtatacgt  11040

tgtcctggcc acggcagaag cacgcttatc gctccaattt cccacaacat tagtcaactc  11100

cgttaggccc ttcattgaaa gaaatgaggt catcaaatgt cttccaatgt gagattttgg  11160

gccatttttt atagcaaaga ttgaataagg cgcatttttc ttca                   11204
```

<210> SEQ ID NO 27
<211> LENGTH: 12008
<212> TYPE: DNA
<213> ORGANISM: Saccharomyces cerevisiae

<400> SEQUENCE: 27

```
gaattctcat gtttgacagc ttatcatcga taagctttaa tgcggtagtt tatcacagtt     60

aaattgctaa cgcagtcagg caccgtgtat gaaatctaac aatgcgctca tcgtcatcct    120

cggcaccgtc accctggatg ctgtaggcat aggcttggtt atgccggtac tgccgggcct    180

cttgcgggat atcgtccatt ccgacagcat cgccagtcac tatggcgtgc tgctagcgct    240

atatgcgttg atgcaatttc tatgcgcacc cgttctcgga gcactgtccg accgctttgg    300

ccgccgccca gtcctgctcg cttcgctact tggagccact atcgactacg cgatcatggc    360

gaccacaccc gtcctgtgga tcaagcggcc gcagtacgta atgcggtatc gtgaaagcga    420

aaaaaaaact aacagtagat aagacagata gacagataga gatggacgag aaacaggggg    480

ggagaaaagg ggaaaagaga aggaaagaaa gactcatcta tcgcagataa gacaatcaac    540

cctcatggcg cctccaacca ccatccgcac tagggaccaa gcgctcgcac cgttagcaac    600

gcttgactca caaaccaact gccggctgaa agagcttgtg caatgggagt gccaattcaa    660

aggagccgaa tacgtctgct cgccttttaa gaggcttttt gaacactgca ttgcacccga    720

caaatcagcc actaactacg aggtcacgga cacatatacc aatagttaaa aattacatat    780

actctatata gcacagtagt gtgataaata aaaaattttg ccaagacttt tttaaactgc    840
```

-continued

```
acccgacaga tcaggtctgt gcctactatg cacttatgcc cggggtcccg ggaggagaaa    900
aaacgagggc tgggaaatgt ccgtggactt taaacgctcc gggttagcag agtagcaggg    960
ctttcggctt tggaaattta ggtgacttgt tgaaaaagca aaatttgggc tcagtaatgc   1020
cactgcagtg gcttatcacg ccaggactgc gggagtggcg ggggcaaaca cacccgcgat   1080
aaagagcgcg atgaatataa aaggggggcca atgttacgtc ccgttatatt ggagttcttc   1140
ccatacaaac ttaagagtcc aattagcttc atcgccaata aaaaaacaag ctaaacctaa   1200
ttctaacaag cacatatgcg gtccggatcc agtttaaaca gtagctttgg acttcttcgc   1260
cagaggtttg gtcaagtctc caatcaaggt tgtcggcttg tctaccttgc cagaaattta   1320
cgaaaagatg gaaaagggtc aaatcgttgg tagatacgtt gttgacactt ctaaataagc   1380
gaatttctta tgatttatga tttttattat taaataagtt ataaaaaaaa taagtgtata   1440
caaattttaa agtgactctt aggttttaaa acgaaaattc ttgttcttga gtaactcttt   1500
cctgtaggtc aggttgcttt ctcaggtata gcatgaggtc gctcttattg accacacctc   1560
taccggcatg ccgagcaaat gcctgcaaat cgctccccat ttcacccaat tgtagatatg   1620
ctaactccag caatgagttg atgaatctcg gtgtgtattt tatgtcctca gaagacaaca   1680
cctgttgtaa tcgttcttcc acacggatcg cggccgcttg atcctctacg ccggacgcat   1740
cgtggccggc atcaccggcg ccacaggtgc ggttgctggc gcctatatcg ccgacatcac   1800
cgatggggaa gatcgggctc gccacttcgg gctcatgagc gcttgtttcg gcgtgggtat   1860
ggtggcaggc cccgtggccg ggggactgtt gggcgccatc tccttgcatg caccattcct   1920
tgcggcggcg gtgctcaacg gcctcaacct actactgggc tgcttcctaa tgcaggagtc   1980
gcataaggga gagcgtcgac cgatgccctt gagagccttc aacccagtca gctccttccg   2040
gtgggcgcgg ggcatgacta tcgtcgccgc acttatgact gtcttcttta tcatgcaact   2100
cgtaggacag gtgccggcag cgctctgggt cattttcggc gaggaccgct ttcgctggag   2160
cgcgacgatg atcggcctgt cgcttgcggt attcggaatc ttgcacgccc tcgctcaagc   2220
cttcgtcact ggtcccgcca ccaaacgttt cggcgagaag caggccatta tcgccggcat   2280
ggcggccgac gcgctgggct acgtcttgct ggcgttcgcg acgcgaggct ggatggcctt   2340
ccccattatg attcttctcg cttccggcgg catcgggatg cccgcgttgc aggccatgct   2400
gtccaggcag gtagatgacg accatcaggg acagcttcaa ggatcgctcg cggctcttac   2460
cagcctaact tcgatcactg gaccgctgat cgtcacggcg atttatgccg cctcggcgag   2520
cacatggaac gggttggcat ggattgtagg cgccgcccta taccttgtct gcctccccgc   2580
gttgcgtcgc ggtgcatgga gccgggccac ctcgacctga atggaagccg gcggcacctc   2640
gctaacggat tcaccactcc aagaattgga gccaatcaat tcttgcggag aactgtgaat   2700
gcgcaaacca acccttggca gaacatatcc atcgcgtccg ccatctccag cagccgcacg   2760
cggcgcatct cgggcagcgt tgggtcctgg ccacgggtgc gcatgatcgt gctcctgtcg   2820
ttgaggaccc ggctaggctg gcggggttgc cttactggtt agcagaatga atcaccgata   2880
cgcgagcgaa cgtgaagcga ctgctgctgc aaaacgtctg cgacctgagc aacaacatga   2940
atggtcttcg gtttccgtgt ttcgtaaagt ctggaaacgc ggaagtcagc gccctgcacc   3000
attatgttcc ggatctgcat cgcaggatgc tgctggctac cctgtggaac acctacatct   3060
gtattaacga agcgctggca ttgaccctga gtgatttttc tctggtcccg ccgcatccat   3120
accgccagtt gtttaccctc acaacgttcc agtaaccggg catgttcatc atcagtaacc   3180
```

-continued

```
cgtatcgtga gcatcctctc tcgtttcatc ggtatcatta cccccatgaa cagaaattcc   3240

cccttacacg gaggcatcaa gtgaccaaac aggaaaaaac cgcccttaac atggcccgct   3300

ttatcagaag ccagacatta acgcttctgg agaaactcaa cgagctggac gcggatgaac   3360

aggcagacat ctgtgaatcg cttcacgacc acgctgatga gctttaccgc agctgcctcg   3420

cgcgtttcgg tgatgacggt gaaaacctct gacacatgca gctcccggag acggtcacag   3480

cttgtctgta agcggatgcc gggagcagac aagcccgtca gggcgcgtca gcgggtgttg   3540

gcgggtgtcg gggcgcagcc atgacccagt cacgtagcga tagcggagtg tatactggct   3600

taactatgcg gcatcagagc agattgtact gagagtgcac gatatccggt gtgaaatacc   3660

gcacagatgc gtaaggagaa aataccgcat caggcgctct tccgcttcct cgctcactga   3720

ctcgctgcgc tcggtcgttc ggctgcggcg agcggtatca gctcactcaa aggcggtaat   3780

acggttatcc acagaatcag gggataacgc aggaaagaac atgtgagcaa aaggccagca   3840

aaaggccagg aaccgtaaaa aggccgcgtt gctggcgttt ttccataggc tccgcccccc   3900

tgacgagcat cacaaaaatc gacgctcaag tcagaggtgg cgaaacccga caggactata   3960

aagataccag gcgtttcccc ctggaagctc cctcgtgcgc tctcctgttc cgaccctgcc   4020

gcttaccgga tacctgtccg cctttctccc ttcgggaagc gtggcgcttt ctcaatgctc   4080

acgctgtagg tatctcagtt cggtgtaggt cgttcgctcc aagctgggct gtgtgcacga   4140

accccccgtt cagcccgacc gctgcgcctt atccggtaac tatcgtcttg agtccaaccc   4200

ggtaagacac gacttatcgc cactggcagc agccactggt aacaggatta gcagagcgag   4260

gtatgtaggc ggtgctacag agttcttgaa gtggtggcct aactacggct acactagaag   4320

gacagtattt ggtatctgcg ctctgctgaa gccagttacc ttcggaaaaa gagttggtag   4380

ctcttgatcc ggcaaacaaa ccaccgctgg tagcggtggt ttttttgttt gcaagcagca   4440

gattacgcgc agaaaaaaag gatctcaaga agatcctttg atcttttcta cggggtctga   4500

cgctcagtgg aacgaaaact cacgttaagg gattttggtc atgagattat caaaaaggat   4560

cttcacctag atccttttaa attaaaaatg aagttttaaa tcaatctaaa gtatatatga   4620

gtaaacttgg tctgacagtt accaatgctt aatcagtgag gcacctatct cagcgatctg   4680

tctatttcgt tcatccatag ttgcctgact ccccgtcgtg tagataacta cgatacggga   4740

gggcttacca tctggcccca gtgctgcaat gataccgcga gacccacgct caccggctcc   4800

agatttatca gcaataaacc agccagccgg aagggccgag cgcagaagtg gtcctgcaac   4860

tttatccgcc tccatccagt ctattaattg ttgccgggaa gctagagtaa gtagttcgcc   4920

agttaatagt ttgcgcaacg ttgttgccat tgctgcaggc atcgtggtgt cacgctcgtc   4980

gtttggtatg gcttcattca gctccggttc ccaacgatca aggcgagtta catgatcccc   5040

catgttgtgc aaaaaagcgg ttagctcctt cggtcctccg atcgttgtca gaagtaagtt   5100

ggccgcagtg ttatcactca tggttatggc agcactgcat aattctctta ctgtcatgcc   5160

atccgtaaga tgcttttctg tgactggtga gtactcaacc aagtcattct gagaatagtg   5220

tatgcggcga ccgagttgct cttgcccggc gtcaacacgg gataataccg cgccacatag   5280

cagaacttta aaagtgctca tcattggaaa acgttcttcg gggcgaaaac tctcaaggat   5340

cttaccgctg ttgagatcca gttcgatgta acccactcgt gcacccaact gatcttcagc   5400

atcttttact ttcaccagcg tttctgggtg agcaaaaaca ggaaggcaaa atgccgcaaa   5460

aaagggaata agggcgacac ggaaatgttg aatactcata ctcttccttt ttcaatatta   5520

ttgaagcatt tatcagggtt attgtctcat gagcggatac atatttgaat gtatttagaa   5580
```

-continued

```
aaataaacaa ataggggttc cgcgcacatt tccccgaaaa gtgccacctg acgtctaaga   5640
aaccattatt atcatgacat taacctataa aaataggcgt atcacgaggc cctttcgtct   5700
tcaagaattc cacggactat agactatact agtatactcc gtctactgta cgatacactt   5760
ccgctcaggt ccttgtcctt taacgaggcc ttaccactct tttgttactc tattgatcca   5820
gctcagcaaa ggcagtgtga tctaagattc tatcttcgcg atgtagtaaa actagctaga   5880
ccgagaaaga gactagaaat gcaaaaggca cttctacaat ggctgccatc attattatcc   5940
gatgtgacgc tgcagaagca gaaatacacg cggtcagtga agctattccg ctattgaata   6000
acctcagtca ccttgtgcaa gaacttaaca agaaaccaat tattaaaggc ttacttactg   6060
atagtagatc aacgatcagt ataattaagt ctacaaatga agagaaattt agaaacagat   6120
tttttggcac aaaggcaatg agacttagag atgaagtatc aggtaataat ttatacgtat   6180
actacatcga gaccaagaag aacattgctg atgtgatgac aaaacctctt ccgataaaaa   6240
catttaaact attaactaac aaatggattc attagatcta ttacattatg ggtggtatgt   6300
tggaataaaa atcaactatc atctactaac tagtatttac gttactagta tattatcata   6360
tacggtgtta gaagatgacg caaatgatga gaaatagtca tctaaattag tggaagctga   6420
aacgcaagga ttgataatgt aataggatca atgaatatta acatataaaa tgatgataat   6480
aatatttata gaattgtgta gaattgcaga ttccctttta tggattccta aatcctcgag   6540
gagaacttct agtatatcta catacctaat attattgcct tattaaaaat ggaatcccaa   6600
caattacatc aaaatccaca ttctcttcaa aatcaattgt cctgtacttc cttgttcatg   6660
tgtgttcaaa aacgttatat ttataggata attatactct atttctcaac aagtaattgg   6720
ttgtttggcc gagcggtcta aggcgcctga ttcaagaaat atcttgaccg cagttaactg   6780
tgggaatact caggtatcgt aagatgcaag agttcgaatc tcttagcaac cattattttt   6840
ttcctcaaca taacgagaac acacaggggc gctatcgcac agaatcaaat tcgatgactg   6900
gaaatttttt gttaatttca gaggtcgcct gacgcatata ccttttcaa ctgaaaaatt   6960
gggagaaaaa ggaaaggtga gagccgcgga accggctttt catatagaat agagaagcgt   7020
tcatgactaa atgcttgcat cacaatactt gaagttgaca atattattta aggacctatt   7080
gtttttcca ataggtggtt agcaatcgtc ttactttcta acttttctta cctttacat   7140
ttcagcaata tatatatata tatttcaagg atataccatt ctaatgtctg ccccctaagaa   7200
gatcgtcgtt ttgccaggtg accacgttgg tcaagaaatc acagccgaag ccattaaggt   7260
tcttaaagct atttctgatg ttcgttccaa tgtcaagttc gatttcgaaa atcatttaat   7320
tggtggtgct gctatcgatg ctacaggtgt cccacttcca gatgaggcgc tggaagcctc   7380
caagaaggtt gatgccgttt tgttaggtgc tgtgggtggt cctaaatggg gtaccggtag   7440
tgttagacct gaacaaggtt tactaaaaat ccgtaaagaa cttcaattgt acgccaactt   7500
aagaccatgt aactttgcat ccgactctct tttagactta tctccaatca agccacaatt   7560
tgctaaaggt actgacttcg ttgttgtcag agaattagtg ggaggtattt actttggtaa   7620
gagaaaggaa gacgatggtg atggtgtcgc ttgggatagt gaacaataca ccgttccaga   7680
agtgcaaaga atcacaagaa tggccgcttt catggcccta caacatgagc caccattgcc   7740
tatttggtcc ttggataaag ctaatgtttt ggcctcttca agattatgga gaaaaactgt   7800
ggaggaaacc atcaagaacg aattccctac attgaaggtt caacatcaat tgattgattc   7860
tgccgccatg atcctagtta agaacccaac ccacctaaat ggtattataa tcaccagcaa   7920
```

-continued

```
catgtttggt gatatcatct ccgatgaagc ctccgttatc ccaggttcct tgggtttgtt   7980
gccatctgcg tccttggcct ctttgccaga caagaacacc gcatttggtt tgtacgaacc   8040
atgccacggt tctgctccag atttgccaaa gaataaggtc aaccctatcg ccactatctt   8100
gtctgctgca atgatgttga aattgtcatt gaacttgcct gaagaaggta aggccattga   8160
agatgcagtt aaaaaggttt tggatgcagg tatcagaact ggtgatttag gtggttccaa   8220
cagtaccacg gaagtcggtg atgctgtcgc cgaagaagtt aagaaaatcc ttgcttaaaa   8280
agattctctt tttttatgat atttgtacat aaactttata aatgaaattc ataatagaaa   8340
cgacacgaaa ttacaaaatg gaatatgttc atagggtaga cgaaactata tacgcaatct   8400
acatacattt atcaagaagg agaaaaagga ggatgtaaag gaatacaggt aagcaaattg   8460
atactaatgg ctcaacgtga taaggaaaaa gaattgcact ttaacattaa tattgacaag   8520
gaggagggca ccacacaaaa agttaggtgt aacagaaaat catgaaacta tgattcctaa   8580
tttatatatt ggaggatttt ctctaaaaaa aaaaaaatac aacaaataaa aaacactcaa   8640
tgacctgacc atttgatgga gtttaagtca ataccttctt gaaccatttc ccataatggt   8700
gaaagttccc tcaagaattt tactctgtca gaaacggcct taacgacgta gtcgacctcc   8760
tcttcagtac taaatctacc aataccaaat ctgatggaag aatgggctaa tgcatcatcc   8820
ttacccagcg catgtaaaac ataagaaggt tctagggaag cagatgtaca ggctgaaccc   8880
gaggataatg cgatatccct tagtgccatc aataaagatt ctccttccac gtaggcgaaa   8940
gaaacgttaa cacaccctgg ataacgatga tctggagatc cgttcaacgt ggtatgttca   9000
gcggataata gacctttgac taatttatcg gatagtcttt tgatgtgagc ttggtcgttg   9060
tcaaattctt tcttcatcaa tctcgcagct tcaccaaatc ccgctaccaa tggggggcc    9120
aaagtaccag atctcaatcc tctctcttgg ccaccaccgg atagtaaagg ttctaatcta   9180
actcttggtc tccttcttac atagatggca cctattccct ttggaccgta aatcttgtga   9240
gaagaaattg atagtaaatc aatgttcatt tcattgacat caatgtgaat cttaccatag   9300
gcttgtgcgg cgtcagtatg aaagtagatc ttattctttc tacaaattgc accaatttct   9360
ttaataggtt gaatgacacc gatttcatta ttgacagcca tcacagagac gagacaggta   9420
tctggtctaa tggcatcttc caattccttc aaatcgataa gaccttgatc gtccacattt   9480
aggaaagtga cttcaaatcc ctccttcatc atggcccgtg cggcttccaa gacacacttg   9540
tgttccgttc tagtggtgat gatgtgtttc ttagtcttct tataaaatct tgggacaccc   9600
ttaagaacca tattattaga ttcggtcgct cccgaagtga atattatttc cttggggtcg   9660
gcattgatca tctttgctac gtaagctcta gcattttcca cagcagtatt tgtttcccaa   9720
ccgtaagagt gagtgttgga atgaggatta ccataaagtc ccgtataaaa cttcaacatc   9780
gtatccaaaa ccctagggtc tgttggtgta gtggcttgca tgtcaagata tatgggacga   9840
gtaccaaaac ctgtgttttc ttgataagca tggctcattg cagtgctacc agaagctact   9900
acagcatctg ggtggtaccc ggatgcactc gcacgggcac tagcctgtgc ctttgcagca   9960
gcctgaatat cggtatgcgt ttccagagag aagttgtcgt ctaacttcac gcctgctgca  10020
gtctcaatga tattcgaata cgctttgagg agatacagcc taatatccga caaactgttt  10080
tacagattta cgatcgtact tgttacccat cattgaattt tgaacatccg aacctgggag  10140
ttttccctga aacagatagt atatttgaac ctgtataata atatatagtc tagcgcttta  10200
cggaagacaa tgtatgtatt tcggttcctg gagaaactat tgcatctatt gcataggtaa  10260
tcttgcacgt cgcatccccg gttcattttc tgcgtttcca tcttgcactt caatagcata  10320
```

```
tctttgttaa cgaagcatct gtgcttcatt ttgtagaaca aaaatgcaac gcgagagcgc  10380

taatttttca aacaaagaat ctgagctgca tttttacaga acagaaatgc aacgcgaaag  10440

cgctatttta ccaacgaaga atctgtgctt catttttgta aaacaaaaat gcaacgcgag  10500

agcgctaatt tttcaaacaa agaatctgag ctgcattttt acagaacaga aatgcaacgc  10560

gagagcgcta ttttaccaac aaagaatcta tacttctttt ttgttctaca aaaatgcatc  10620

ccgagagcgc tatttttcta acaaagcatc ttagattact ttttttctcc tttgtgcgct  10680

ctataatgca gtctcttgat aactttttgc actgtaggtc cgttaaggtt agaagaaggc  10740

tactttggtg tctattttct cttccataaa aaaagcctga ctccacttcc cgcgtttact  10800

gattactagc gaagctgcgg gtgcattttt tcaagataaa ggcatccccg attatattct  10860

ataccgatgt ggattgcgca tactttgtga acagaaagtg atagcgttga tgattcttca  10920

ttggtcagaa aattatgaac ggtttcttct attttgtctc tatatactac gtataggaaa  10980

tgtttacatt ttcgtattgt tttcgattca ctctatgaat agttcttact acaatttttt  11040

tgtctaaaga gtaatactag agataaacat aaaaaatgta gaggtcgagt ttagatgcaa  11100

gttcaaggag cgaaaggtgg atgggtaggt tatataggga tatagcacag agatatatag  11160

caaagagata cttttgagca atgtttgtgg aagcggtatt cgcaatattt tagtagctcg  11220

ttacagtccg gtgcgttttt ggtttttga aagtgcgtct tcagagcgct tttggttttc  11280

aaaagcgctc tgaagttcct atactttcta gagaatagga acttcggaat aggaacttca  11340

aagcgtttcc gaaaacgagc gcttccgaaa atgcaacgcg agctgcgcac atacagctca  11400

ctgttcacgt cgcacctata tctgcgtgtt gcctgtatat atatatacat gagaagaacg  11460

gcatagtgcg tgtttatgct taaatgcgta cttatatgcg tctatttatg taggatgaaa  11520

ggtagtctag tacctcctgt gatattatcc cattccatgc ggggtatcgt atgcttcctt  11580

cagcactacc ctttagctgt tctatatgct gccactcctc aattggatta gtctcatcct  11640

tcaatgctat catttccttt gatattcgat cctaggcata gtaccgagaa actagtgcga  11700

agtagtgatc aggtattgct gttatctgat gagtatacgt tgtcctggcc acggcagaag  11760

cacgcttatc gctccaattt cccacaacat tagtcaactc cgttaggccc ttcattgaaa  11820

gaaatgaggt catcaaatgt cttccaatgt gagattttgg gccatttttt atagcaaaga  11880

ttgaataagg cgcatttttc ttcaaagctt tattgtacga tctgactaag ttatctttta  11940

ataattggta ttcctgttta ttgcttgaag aattgccggt cctatttact cgttttagga  12000

ctggttca                                                           12008
```

<210> SEQ ID NO 28
<211> LENGTH: 13654
<212> TYPE: DNA
<213> ORGANISM: Saccharomyces cerevisiae

<400> SEQUENCE: 28

```
gaattctcat gtttgacagc ttatcatcga taagctttaa tgcggtagtt tatcacagtt     60

aaattgctaa cgcagtcagg caccgtgtat gaaatctaac aatgcgctca tcgtcatcct    120

cggcaccgtc accctggatg ctgtaggcat aggcttggtt atgccggtac tgccgggcct    180

cttgcgggat atcgtccatt ccgacagcat cgccagtcac tatggcgtgc tgctagcgct    240

atatgcgttg atgcaatttc tatgcgcacc cgttctcgga gcactgtccg accgctttgg    300

ccgccgccca gtcctgctcg cttcgctact tggagccact atcgactacg cgatcatggc    360
```

-continued

```
gaccacaccc gtcctgtgga tcaagcggcc gcagtacgta atgcggtatc gtgaaagcga    420
aaaaaaaact aacagtagat aagacagata gacagataga gatggacgag aaacaggggg    480
ggagaaaagg ggaaaagaga aggaaagaaa gactcatcta tcgcagataa gacaatcaac    540
cctcatggcg cctccaacca ccatccgcac tagggaccaa gcgctcgcac cgttagcaac    600
gcttgactca caaaccaact gccggctgaa agagcttgtg caatgggagt gccaattcaa    660
aggagccgaa tacgtctgct cgccttttaa gaggcttttt gaacactgca ttgcacccga    720
caaatcagcc actaactacg aggtcacgga cacatatacc aatagttaaa aattacatat    780
actctatata gcacagtagt gtgataaata aaaaattttg ccaagacttt tttaaactgc    840
acccgacaga tcaggtctgt gcctactatg cacttatgcc cggggtcccg ggaggagaaa    900
aaacgagggc tgggaaatgt ccgtggactt taaacgctcc gggttagcag agtagcaggg    960
ctttcggctt tggaaattta ggtgacttgt tgaaaaagca aaatttgggc tcagtaatgc   1020
cactgcagtg gcttatcacg ccaggactgc gggagtggcg gggcaaaca cacccgcgat    1080
aaagagcgcg atgaatataa aaggggcca atgttacgtc ccgttatatt ggagttcttc    1140
ccatacaaac ttaagagtcc aattagcttc atcgccaata aaaaaacaag ctaaacctaa   1200
ttctaacaag cacatatgga agacgccaaa aacataaaga aaggcccggc gccattctat   1260
ccgctggaag atggaaccgc tggagagcaa ctgcataagg ctatgaagag atacgccctg   1320
gttcctggaa caattgcttt tacagatgca catatcgagg tggacatcac ttacgctgag   1380
tacttcgaaa tgtccgttcg gttggcagaa gctatgaaac gatatgggct gaatacaaat   1440
cacagaatcg tcgtatgcag tgaaaactct cttcaattct ttatgccggt gttgggcgcg   1500
ttatttatcg gagttgcagt tgcgcccgcg aacgacattt ataatgaacg tgaattgctc   1560
aacagtatgg gcatttcgca gcctaccgtg gtgttcgttt ccaaaaaggg gttgcaaaaa   1620
attttgaacg tgcaaaaaaa gctcccaatc atccaaaaaa ttattatcat ggattctaaa   1680
acggattacc agggatttca gtcgatgtac acgttcgtca catctcatct acctcccggt   1740
tttaatgaat acgattttgt gccagagtcc ttcgataggg acaagacaat tgcactgatc   1800
atgaactcct ctggatctac tggtctgcct aaaggtgtcg ctctgcctca tagaactgcc   1860
tgcgtgagat tctcgcatgc cagagatcct atttttggca atcaaatcat tccggatact   1920
gcgattttaa gtgttgttcc attccatcac ggttttggaa tgtttactac actcggatat   1980
ttgatatgtg gatttcgagt cgtcttaatg tatagatttg aagaagagct gtttctgagg   2040
agccttcagg attacaagat tcaaagtgcg ctgctggtgc caaccctatt ctccttcttc   2100
gccaaaagca ctctgattga caaatacgat ttatctaatt tacacgaaat tgcttctggt   2160
ggcgctcccc tctctaagga agtcggggaa gcggttgcca agaggttcca tctgccaggt   2220
atcaggcaag gatatgggct cactgagact acatcagcta ttctgattac acccgagggg   2280
gatgataaac cgggcgcggt cggtaaagtt gttccatttt ttgaagcgaa ggttgtggat   2340
ctggataccg ggaaaacgct gggcgttaat caaagaggcg aactgtgtgt gagaggtcct   2400
atgattatgt ccggttatgt aaacaatccg gaagcgacca acgccttgat tgacaaggat   2460
ggatggctac attctggaga catagcttac tgggacgaag acgaacactt cttcatcgtt   2520
gaccgcctga agtctctgat taagtacaaa ggctatcagg tggctcccgc tgaattggaa   2580
tccatcttgc tccaacaccc caacatcttc gacgcaggtg tcgcaggtct tcccgacgat   2640
gacgccggtg aacttcccgc cgccgttgtt gttttggagc acggaaagac gatgacggaa   2700
aaagagatcg tggattacgt cgccagtcaa gtaacaaccg cgaaaaagtt gcgcggagga   2760
```

-continued

```
gttgtgtttg tggacgaagt accgaaaggt cttaccggaa aactcgacgc aagaaaaatc   2820
agagagatcc tcataaaggc caagaagggc ggaaagatcg ccgtgtaatt ggatccagtt   2880
taaacagtag ctttggactt cttcgccaga ggtttggtca agtctccaat caaggttgtc   2940
ggcttgtcta ccttgccaga aatttacgaa aagatggaaa agggtcaaat cgttggtaga   3000
tacgttgttg acacttctaa ataagcgaat ttcttatgat ttatgatttt tattattaaa   3060
taagttataa aaaaaataag tgtatacaaa ttttaaagtg actcttaggt tttaaaacga   3120
aaattcttgt tcttgagtaa ctctttcctg taggtcaggt tgctttctca ggtatagcat   3180
gaggtcgctc ttattgacca cacctctacc ggcatgccga gcaaatgcct gcaaatcgct   3240
ccccatttca cccaattgta gatatgctaa ctccagcaat gagttgatga atctcggtgt   3300
gtattttatg tcctcagaag acaacacctg ttgtaatcgt tcttccacac ggatcgcggc   3360
cgcttgatcc tctacgccgg acgcatcgtg gccggcatca ccggcgccac aggtgcggtt   3420
gctggcgcct atatcgccga catcaccgat ggggaagatc gggctcgcca cttcgggctc   3480
atgagcgctt gtttcggcgt gggtatggtg gcaggccccg tggccggggg actgttgggc   3540
gccatctcct tgcatgcacc attccttgcg gcggcggtgc tcaacggcct caacctacta   3600
ctgggctgct tcctaatgca ggagtcgcat aagggagagc gtcgaccgat gcccttgaga   3660
gccttcaacc cagtcagctc cttccggtgg gcgcggggca tgactatcgt cgccgcactt   3720
atgactgtct tctttatcat gcaactcgta ggacaggtgc cggcagcgct ctgggtcatt   3780
ttcggcgagg accgctttcg ctggagcgcg acgatgatcg gcctgtcgct tgcggtattc   3840
ggaatcttgc acgccctcgc tcaagccttc gtcactggtc ccgccaccaa acgtttcggc   3900
gagaagcagg ccattatcgc cggcatggcg gccgacgcgc tgggctacgt cttgctggcg   3960
ttcgcgacgc gaggctggat ggccttcccc attatgattc ttctcgcttc cggcggcatc   4020
gggatgcccg cgttgcaggc catgctgtcc aggcaggtag atgacgacca tcagggacag   4080
cttcaaggat cgctcgcggc tcttaccagc ctaacttcga tcactggacc gctgatcgtc   4140
acggcgattt atgccgcctc ggcgagcaca tggaacgggt tggcatggat tgtaggcgcc   4200
gccctatacc ttgtctgcct ccccgcgttg cgtcgcggtg catggagccg ggccacctcg   4260
acctgaatgg aagccggcgg cacctcgcta acggattcac cactccaaga attggagcca   4320
atcaattctt gcggagaact gtgaatgcgc aaaccaaccc ttggcagaac atatccatcg   4380
cgtccgccat ctccagcagc cgcacgcggc gcatctcggg cagcgttggg tcctggccac   4440
gggtgcgcat gatcgtgctc ctgtcgttga ggacccggct aggctggcgg ggttgcctta   4500
ctggttagca gaatgaatca ccgatacgcg agcgaacgtg aagcgactgc tgctgcaaaa   4560
cgtctgcgac ctgagcaaca acatgaatgg tcttcggttt ccgtgtttcg taaagtctgg   4620
aaacgcggaa gtcagcgccc tgcaccatta tgttccggat ctgcatcgca ggatgctgct   4680
ggctaccctg tggaacacct acatctgtat taacgaagcg ctggcattga ccctgagtga   4740
tttttctctg gtcccgccgc atccataccg ccagttgttt accctcacaa cgttccagta   4800
accgggcatg ttcatcatca gtaacccgta tcgtgagcat cctctctcgt ttcatcggta   4860
tcattacccc catgaacaga aattccccct tacacggagg catcaagtga ccaaacagga   4920
aaaaaccgcc cttaacatgg cccgctttat cagaagccag acattaacgc ttctggagaa   4980
actcaacgag ctggacgcgg atgaacaggc agacatctgt gaatcgcttc acgaccacgc   5040
tgatgagctt taccgcagct gcctcgcgcg tttcggtgat gacggtgaaa acctctgaca   5100
```

-continued

```
catgcagctc ccggagacgg tcacagcttg tctgtaagcg gatgccggga gcagacaagc   5160
ccgtcagggc gcgtcagcgg gtgttggcgg gtgtcggggc gcagccatga cccagtcacg   5220
tagcgatagc ggagtgtata ctggcttaac tatgcggcat cagagcagat tgtactgaga   5280
gtgcacgata tccggtgtga aataccgcac agatgcgtaa ggagaaaata ccgcatcagg   5340
cgctcttccg cttcctcgct cactgactcg ctgcgctcgg tcgttcggct gcggcgagcg   5400
gtatcagctc actcaaaggc ggtaatacgg ttatccacag aatcagggga taacgcagga   5460
aagaacatgt gagcaaaagg ccagcaaaag gccaggaacc gtaaaaaggc cgcgttgctg   5520
gcgtttttcc ataggctccg cccccctgac gagcatcaca aaaatcgacg ctcaagtcag   5580
aggtggcgaa acccgacagg actataaaga taccaggcgt ttccccctgg aagctccctc   5640
gtgcgctctc ctgttccgac cctgccgctt accggatacc tgtccgcctt tctcccttcg   5700
ggaagcgtgg cgctttctca atgctcacgc tgtaggtatc tcagttcggt gtaggtcgtt   5760
cgctccaagc tgggctgtgt gcacgaaccc cccgttcagc ccgaccgctg cgccttatcc   5820
ggtaactatc gtcttgagtc caacccggta agacacgact tatcgccact ggcagcagcc   5880
actggtaaca ggattagcag agcgaggtat gtaggcggtg ctacagagtt cttgaagtgg   5940
tggcctaact acggctacac tagaaggaca gtatttggta tctgcgctct gctgaagcca   6000
gttaccttcg gaaaaagagt tggtagctct tgatccggca aacaaaccac cgctggtagc   6060
ggtggttttt ttgtttgcaa gcagcagatt acgcgcagaa aaaaaggatc tcaagaagat   6120
cctttgatct tttctacggg gtctgacgct cagtggaacg aaaactcacg ttaagggatt   6180
ttggtcatga gattatcaaa aaggatcttc acctagatcc ttttaaatta aaaatgaagt   6240
tttaaatcaa tctaaagtat atatgagtaa acttggtctg acagttacca atgcttaatc   6300
agtgaggcac ctatctcagc gatctgtcta tttcgttcat ccatagttgc ctgactcccc   6360
gtcgtgtaga taactacgat acgggagggc ttaccatctg gccccagtgc tgcaatgata   6420
ccgcgagacc cacgctcacc ggctccagat ttatcagcaa taaaccagcc agccggaagg   6480
gccgagcgca gaagtggtcc tgcaacttta tccgcctcca tccagtctat taattgttgc   6540
cgggaagcta gagtaagtag ttcgccagtt aatagtttgc gcaacgttgt tgccattgct   6600
gcaggcatcg tggtgtcacg ctcgtcgttt ggtatggctt cattcagctc cggttcccaa   6660
cgatcaaggc gagttacatg atcccccatg ttgtgcaaaa aagcggttag ctccttcggt   6720
cctccgatcg ttgtcagaag taagttggcc gcagtgttat cactcatggt tatggcagca   6780
ctgcataatt ctcttactgt catgccatcc gtaagatgct tttctgtgac tggtgagtac   6840
tcaaccaagt cattctgaga atagtgtatg cggcgaccga gttgctcttg cccggcgtca   6900
acacgggata ataccgcgcc acatagcaga actttaaaag tgctcatcat tggaaaacgt   6960
tcttcggggc gaaaactctc aaggatctta ccgctgttga gatccagttc gatgtaaccc   7020
actcgtgcac ccaactgatc ttcagcatct tttactttca ccagcgtttc tgggtgagca   7080
aaaacaggaa ggcaaaatgc cgcaaaaaag ggaataaggg cgacacggaa atgttgaata   7140
ctcatactct tcctttttca atattattga agcatttatc agggttattg tctcatgagc   7200
ggatacatat ttgaatgtat ttagaaaaat aaacaaatag gggttccgcg cacatttccc   7260
cgaaaagtgc cacctgacgt ctaagaaacc attattatca tgacattaac ctataaaaat   7320
aggcgtatca cgaggccctt tcgtcttcaa gaattccacg gactatagac tatactagta   7380
tactccgtct actgtacgat acacttccgc tcaggtcctt gtcctttaac gaggccttac   7440
cactcttttg ttactctatt gatccagctc agcaaaggca gtgtgatcta agattctatc   7500
```

-continued

```
ttcgcgatgt agtaaaacta gctagaccga gaaagagact agaaatgcaa aaggcacttc   7560
tacaatggct gccatcatta ttatccgatg tgacgctgca gaagcagaaa tacacgcggt   7620
cagtgaagct attccgctat tgaataacct cagtcacctt gtgcaagaac ttaacaagaa   7680
accaattatt aaaggcttac ttactgatag tagatcaacg atcagtataa ttaagtctac   7740
aaatgaagag aaatttagaa acagattttt tggcacaaag gcaatgagac ttagagatga   7800
agtatcaggt aataatttat acgtatacta catcgagacc aagaagaaca ttgctgatgt   7860
gatgacaaaa cctcttccga taaaaacatt taaactatta actaacaaat ggattcatta   7920
gatctattac attatgggtg gtatgttgga ataaaaatca actatcatct actaactagt   7980
atttacgtta ctagtatatt atcatatacg gtgttagaag atgacgcaaa tgatgagaaa   8040
tagtcatcta aattagtgga agctgaaacg caaggattga taatgtaata ggatcaatga   8100
atattaacat ataaaatgat gataataata tttatagaat tgtgtagaat tgcagattcc   8160
cttttatgga ttcctaaatc ctcgaggaga acttctagta tatctacata cctaatatta   8220
ttgccttatt aaaaatggaa tcccaacaat tacatcaaaa tccacattct cttcaaaatc   8280
aattgtcctg tacttccttg ttcatgtgtg ttcaaaaacg ttatatttat aggataatta   8340
tactctattt ctcaacaagt aattggttgt ttggccgagc ggtctaaggc gcctgattca   8400
agaaatatct tgaccgcagt taactgtggg aatactcagg tatcgtaaga tgcaagagtt   8460
cgaatctctt agcaaccatt atttttttcc tcaacataac gagaacacac aggggcgcta   8520
tcgcacagaa tcaaattcga tgactggaaa ttttttgtta atttcagagg tcgcctgacg   8580
catatacctt tttcaactga aaaattggga gaaaaaggaa aggtgagagc cgcggaaccg   8640
gcttttcata tagaatagag aagcgttcat gactaaatgc ttgcatcaca atacttgaag   8700
ttgacaatat tatttaagga cctattgttt tttccaatag gtggttagca atcgtcttac   8760
tttctaactt ttcttacctt ttacatttca gcaatatata tatatatatt tcaaggatat   8820
accattctaa tgtctgcccc taagaagatc gtcgttttgc caggtgacca cgttggtcaa   8880
gaaatcacag ccgaagccat taaggttctt aaagctattt ctgatgttcg ttccaatgtc   8940
aagttcgatt tcgaaaatca tttaattggt ggtgctgcta tcgatgctac aggtgtccca   9000
cttccagatg aggcgctgga agcctccaag aaggttgatg ccgttttgtt aggtgctgtg   9060
ggtggtccta aatggggtac cggtagtgtt agacctgaac aaggtttact aaaaatccgt   9120
aaagaacttc aattgtacgc caacttaaga ccatgtaact ttgcatccga ctctctttta   9180
gacttatctc caatcaagcc acaatttgct aaaggtactg acttcgttgt tgtcagagaa   9240
ttagtgggag gtatttactt tggtaagaga aaggaagacg atggtgatgg tgtcgcttgg   9300
gatagtgaac aatacaccgt tccagaagtg caaagaatca caagaatggc cgctttcatg   9360
gccctacaac atgagccacc attgcctatt tggtccttgg ataaagctaa tgttttggcc   9420
tcttcaagat tatggagaaa aactgtggag gaaaccatca agaacgaatt ccctacattg   9480
aaggttcaac atcaattgat tgattctgcc gccatgatcc tagttaagaa cccaacccac   9540
ctaaatggta ttataatcac cagcaacatg tttggtgata tcatctccga tgaagcctcc   9600
gttatcccag gttccttggg tttgttgcca tctgcgtcct tggcctcttt gccagacaag   9660
aacaccgcat ttggtttgta cgaaccatgc cacggttctg ctccagattt gccaaagaat   9720
aaggtcaacc ctatcgccac tatcttgtct gctgcaatga tgttgaaatt gtcattgaac   9780
ttgcctgaag aaggtaaggc cattgaagat gcagttaaaa aggttttgga tgcaggtatc   9840
```

-continued

```
agaactggtg atttaggtgg ttccaacagt accacggaag tcggtgatgc tgtcgccgaa    9900
gaagttaaga aaatccttgc ttaaaaagat tctctttttt tatgatattt gtacataaac    9960
tttataaatg aaattcataa tagaaacgac acgaaattac aaaatggaat atgttcatag   10020
ggtagacgaa actatatacg caatctacat acatttatca agaaggagaa aaaggaggat   10080
gtaaaggaat acaggtaagc aaattgatac taatggctca acgtgataag gaaaaagaat   10140
tgcactttaa cattaatatt gacaaggagg agggcaccac acaaaaagtt aggtgtaaca   10200
gaaaatcatg aaactatgat tcctaattta tatattggag gattttctct aaaaaaaaaa   10260
aaatacaaca aataaaaaac actcaatgac ctgaccattt gatggagttt aagtcaatac   10320
cttcttgaac catttcccat aatggtgaaa gttccctcaa gaattttact ctgtcagaaa   10380
cggccttaac gacgtagtcg acctcctctt cagtactaaa tctaccaata ccaaatctga   10440
tggaagaatg ggctaatgca tcatccttac ccagcgcatg taaaacataa gaaggttcta   10500
gggaagcaga tgtacaggct gaacccgagg ataatgcgat atcccttagt gccatcaata   10560
aagattctcc ttccacgtag gcgaaagaaa cgttaacaca ccctggataa cgatgatctg   10620
gagatccgtt caacgtggta tgttcagcgg ataatagacc tttgactaat ttatcggata   10680
gtcttttgat gtgagcttgg tcgttgtcaa attctttctt catcaatctc gcagcttcac   10740
caaatcccgc taccaatggg ggggccaaag taccagatct caatcctctc tcttggccac   10800
caccggatag taaaggttct aatctaactc ttggtctcct tcttacatag atggcaccta   10860
ttccctttgg accgtaaatc ttgtgagaag aaattgatag taaatcaatg ttcatttcat   10920
tgacatcaat gtgaatctta ccataggctt gtgcggcgtc agtatgaaag tagatcttat   10980
tctttctaca aattgcacca atttctttaa taggttgaat gacaccgatt tcattattga   11040
cagccatcac agagacgaga caggtatctg gtctaatggc atcttccaat tccttcaaat   11100
cgataagacc ttgatcgtcc acatttagga aagtgacttc aaatccctcc ttcatcatgg   11160
cccgtgcggc ttccaagaca cacttgtgtt ccgttctagt ggtgatgatg tgtttcttag   11220
tcttcttata aaatcttggg acacccttaa gaaccatatt attagattcg gtcgctcccg   11280
aagtgaatat tatttccttg ggtcggcat tgatcatctt tgctacgtaa gctctagcat   11340
tttccacagc agtatttgtt tcccaaccgt aagagtgagt gttggaatga ggattaccat   11400
aaagtcccgt ataaaacttc aacatcgtat ccaaaaccct agggtctgtt ggtgtagtgg   11460
cttgcatgtc aagatatatg ggacgagtac caaaacctgt gttttcttga taagcatggc   11520
tcattgcagt gctaccagaa gctactacag catctggggt ggtaccggat gcactcgcac   11580
gggcactagc ctgtgccttt gcagcagcct gaatatcggt atgcgtttcc agagagaagt   11640
tgtcgtctaa cttcacgcct gctgcagtct caatgatatt cgaatacgct ttgaggagat   11700
acagcctaat atccgacaaa ctgttttaca gatttacgat cgtacttgtt acccatcatt   11760
gaattttgaa catccgaacc tgggagtttt ccctgaaaca gatagtatat ttgaacctgt   11820
ataataatat atagtctagc gctttacgga agacaatgta tgtatttcgg ttcctggaga   11880
aactattgca tctattgcat aggtaatctt gcacgtcgca tccccggttc attttctgcg   11940
tttccatctt gcacttcaat agcatatctt tgttaacgaa gcatctgtgc ttcattttgt   12000
agaacaaaaa tgcaacgcga gagcgctaat ttttcaaaca aagaatctga gctgcatttt   12060
tacagaacag aaatgcaacg cgaaagcgct attttaccaa cgaagaatct gtgcttcatt   12120
tttgtaaaac aaaaatgcaa cgcgagagcg ctaatttttc aaacaaagaa tctgagctgc   12180
atttttacag aacagaaatg caacgcgaga gcgctatttt accaacaaag aatctatact   12240
```

```
tctttttgt tctacaaaaa tgcatcccga gagcgctatt tttctaacaa agcatcttag  12300
attacttttt ttctcctttg tgcgctctat aatgcagtct cttgataact ttttgcactg  12360
taggtccgtt aaggttagaa gaaggctact ttggtgtcta ttttctcttc cataaaaaaa  12420
gcctgactcc acttcccgcg tttactgatt actagcgaag ctgcgggtgc attttttcaa  12480
gataaaggca tccccgatta tattctatac cgatgtggat tgcgcatact ttgtgaacag  12540
aaagtgatag cgttgatgat tcttcattgg tcagaaaatt atgaacggtt tcttctattt  12600
tgtctctata tactacgtat aggaaatgtt tacattttcg tattgttttc gattcactct  12660
atgaatagtt cttactacaa tttttttgtc taaagagtaa tactagagat aaacataaaa  12720
aatgtagagg tcgagtttag atgcaagttc aaggagcgaa aggtggatgg gtaggttata  12780
tagggatata gcacagagat atatagcaaa gagatacttt tgagcaatgt ttgtggaagc  12840
ggtattcgca atattttagt agctcgttac agtccggtgc gtttttggtt ttttgaaagt  12900
gcgtcttcag agcgcttttg gttttcaaaa gcgctctgaa gttcctatac tttctagaga  12960
ataggaactt cggaatagga acttcaaagc gtttccgaaa acgagcgctt ccgaaaatgc  13020
aacgcgagct gcgcacatac agctcactgt tcacgtcgca cctatatctg cgtgttgcct  13080
gtatatatat atacatgaga agaacggcat agtgcgtgtt tatgcttaaa tgcgtactta  13140
tatgcgtcta tttatgtagg atgaaaggta gtctagtacc tcctgtgata ttatcccatt  13200
ccatgcgggg tatcgtatgc ttccttcagc actacccttt agctgttcta tatgctgcca  13260
ctcctcaatt ggattagtct catccttcaa tgctatcatt tcctttgata ttcgatccta  13320
ggcatagtac cgagaaacta gtgcgaagta gtgatcaggt attgctgtta tctgatgagt  13380
atacgttgtc ctggccacgg cagaagcacg cttatcgctc caatttccca caacattagt  13440
caactccgtt aggcccttca ttgaaagaaa tgaggtcatc aaatgtcttc caatgtgaga  13500
ttttgggcca tttttatag caaagattga ataaggcgca tttttcttca aagctttatt  13560
gtacgatctg actaagttat cttttaataa ttggtattcc tgtttattgc ttgaagaatt  13620
gccggtccta tttactcgtt ttaggactgg ttca                             13654
```

<210> SEQ ID NO 29
<211> LENGTH: 600
<212> TYPE: DNA
<213> ORGANISM: Saccharomyces cerevisiae

<400> SEQUENCE: 29

```
agaaccaaat gggaaaatcg gaatgggtcc agaactgctt tgagtgctgg ctattggcgt     60
ctgatttccg ttttgggaat cctttgccgc gcgcccctct caaaactccg cacaagtccc    120
agaaagcggg aaagaaataa aacgccacca aaaaaaaaaa aataaaagcc aatcctcgaa    180
gcgtgggtgg taggccctgg attatcccgt acaagtattt ctcaggagta aaaaaaccgt    240
ttgttttgga attccccatt tcgcggccac ctacgccgct atctttgcaa caactatctg    300
cgataactca gcaaattttg catattcgtg ttgcagtatt gcgataatgg gagtcttact    360
tccaacataa cggcagaaag aaatgtgaga aaattttgca tcctttgcct ccgttcaagt    420
atataaagtc ggcatgcttg ataatctttc tttccatcct acattgttct aattattctt    480
attctccttt attctttcct aacataccaa gaaattaatc ttctgtcatt cgcttaaaca    540
ctatatcaat aatgcaattt tctactgtcg cttctatcgc cgctgtcgcc gctgtcgctt    600
```

<210> SEQ ID NO 30

-continued

<211> LENGTH: 850
<212> TYPE: DNA
<213> ORGANISM: Saccharomyces cerevisiae

<400> SEQUENCE: 30

```
gccacgggtc aacccgattg ggatcacccc actggggccc aagcctgata tccgacctcc     60
atgaaatttt tttttttctt tcgattagca cgcacacaca tcacatagac tgcgtcataa    120
aaatacacta cggaaaaacc ataaagagca aagcgatacc tacttggaag gaaaaggagc    180
acgcttgtaa gggggatggg ggctaagaag tcattcactt tcttttccct tcgcggtccg    240
gacccgggac ccctcctctc cccgcacgat ttcttccttt catatcttcc ttttattcct    300
atcccgttga agcaaccgca ctatgactaa atggtgctgg acatctccat ggctgtgact    360
tgtgtgtatc tcacagtggt aacggcaccg tggctcggaa acggttcctt cgtgacaatt    420
ctagaacagg ggctacagtc tcgataatag aataataagc gcatttttgc tagcgccgcc    480
gcggcgcccg tttcccaata gggaggcgca gtttatcggc ggagctctac ttcttcctat    540
ttgggtaagc ccctttctgt tttcggccag tggttgctgc aggctgcgcc ggagaacata    600
gtgataaggg atgtaacttt cgatgagaga attagcaagc ggaaaaaaac tatggctagc    660
tgggagttgt ttttcaatca tataaaaggg agaaattgtt gctcactatg tgacagtttc    720
tgggacgtct taacttttat tgcagaggac tatcaaatca tacagatatt gtcaaaaaaa    780
aaaaagacta ataataaaaa atgaagttat ctcaagttgt tgtttccgcc gtcgccttca    840
ctggtttagt                                                           850
```

<210> SEQ ID NO 31
<211> LENGTH: 600
<212> TYPE: DNA
<213> ORGANISM: Saccharomyces cerevisiae

<400> SEQUENCE: 31

```
aaagaatcca tcactatttg aaaaaaagtc atctggcacg tttaattatc agagcagaaa     60
tgatgaaggg tgttagcgcc gtccactgat gtgcctggta gtcatgattt acgtataact    120
aacacatcat gaggacggcg gcgtcacccc aacgcaaaag agtgacttcc ctgcgctttg    180
ccaaaacccc atacatcgcc atctggctcc tggcagggcg gttgatggac atcagccgcc    240
tcccttaatt gctaaagcct ccacaaggca caattaagca atatttcggg aaagtacacc    300
agtcagtttg cgcttttatg actgggttct aaggtactag atgtgaagta gtggtgacag    360
aatcagggag ataagaggga gcagggtggg gtaatgatgt gcgataacaa tcttgcttgg    420
ctaatcaccc ccatatcttg tagtgagtat ataaatagga gcctcccttc ctattgcaac    480
tccataaaat tttttttgt agccacttct gtaacaagat aaataaaacc aactaatcga    540
gatatcaaat atgggtagtt tttgggacgc attcgcagta tacgacaaga aaaagcacgc    600
```

<210> SEQ ID NO 32
<211> LENGTH: 600
<212> TYPE: DNA
<213> ORGANISM: Saccharomyces cerevisiae

<400> SEQUENCE: 32

```
ttcaggagtc tctcgcgtta gagcagtacg tggcgcagct aaactcgccg ggaggtctgc     60
ttcacgagcg cggtgtgcgc ctagtattgc cccgacggtc cgggtgccta tccctagatt    120
tcgtcgtgcc ccgacccaaa tagttaaacg tgtggtttat gggtgcacca gggctttatc    180
gtgttttata tcgatggcga tttgtgcctc cagtgtattt ttgtatatcc aattaaggtt    240
```

-continued

```
tcttacctaa ttttattttt atcatcttta gttaatgctg gtttgctctg tttctgctgc    300

tttctgtgcg gttctcctct tctcttgttt cttcgtgttg tcccccatcg ccgatgggct    360

tatatggcgt atatatatag agcgagtttt tacgtcgaag atcatctcag tttgcttgat    420

agcctttcta ctttattact ttcgttttta acctcattat actttagttt tctttgatcg    480

gttttttttct ctgtatactt aaaagttcaa atcaaagaaa catacaaaac tacgtttata    540

tcaattaata atgtctgaaa ttcaaaacaa agctgaaact gccgcccaag atgtccaaca    600
```